US011311856B2

(12) United States Patent
Long et al.

(10) Patent No.: US 11,311,856 B2
(45) Date of Patent: Apr. 26, 2022

(54) VANADIUM METAL-ORGANIC FRAMEWORK FOR SELECTIVE ADSORPTION

(71) Applicant: The Regents of the University of California, Oakland, CA (US)

(72) Inventors: Jeffrey R. Long, Oakland, CA (US); David E. Jaramillo, Berkeley, CA (US); Douglas A. Reed, New York, NY (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 148 days.

(21) Appl. No.: 16/767,488

(22) PCT Filed: Nov. 29, 2018

(86) PCT No.: PCT/US2018/063154
§ 371 (c)(1),
(2) Date: May 27, 2020

(87) PCT Pub. No.: WO2019/108847
PCT Pub. Date: Jun. 6, 2019

(65) Prior Publication Data
US 2020/0376463 A1 Dec. 3, 2020

Related U.S. Application Data

(60) Provisional application No. 62/591,930, filed on Nov. 29, 2017.

(51) Int. Cl.
*B01J 20/22* (2006.01)
*B01J 20/28* (2006.01)
(Continued)

(52) U.S. Cl.
CPC ............ *B01J 20/226* (2013.01); *B01D 53/02* (2013.01); *B01J 20/3071* (2013.01);
(Continued)

(58) Field of Classification Search
None
See application file for complete search history.

(56) References Cited

U.S. PATENT DOCUMENTS

2014/0294709 A1  10/2014  Long et al.
2017/0341010 A1  11/2017  Dinca et al.
(Continued)

FOREIGN PATENT DOCUMENTS

WO    WO 2013/059527 A1    4/2013
WO    WO 2015/164543 A1    10/2015
(Continued)

OTHER PUBLICATIONS

International Search Report and Written Opinion for International Application No. PCT/US2018/063154 dated Feb. 25, 2019, 12 pages.
(Continued)

*Primary Examiner* — Daniel Berns
(74) *Attorney, Agent, or Firm* — Morgan, Lewis & Bockius LLP; Brett A. Lovejoy

(57) ABSTRACT

A permanently porous vanadium(II)-containing metal-organic framework (MOF) with vanadium(II) centers and methods for synthesis of such MOF frameworks are provided. Methods for using such compounds to selectively react with $N^2$ over $CH_4$ are provided. In the synthetic methods, a vanadium source, such as $VY_2(tmeda)_2$, where Y is a halogen and tmeda is N,N,N',N'-tetramethylethane-1,2-diamine and a $H_2$(ligand) are reacted in the presence of acid in a solvent at between 110° C. and 130° C. to form an intermediate product. The intermediate product is collected
(Continued)

$V_2Cl_{2.8}$(btdd)

and washed with a washing agent, such as DMF and acetonitrile, and the vanadium(II) based MOF is activated by heating the washed intermediate product to at least 160° C. under dynamic vacuum.

25 Claims, 23 Drawing Sheets

(51) Int. Cl.
    B01J 20/30      (2006.01)
    B01J 20/34      (2006.01)
    B01D 53/02      (2006.01)
    C10L 3/10       (2006.01)
    C07F 19/00      (2006.01)
    C07C 7/12       (2006.01)

(52) U.S. Cl.
    CPC ..... *B01J 20/3078* (2013.01); *B01D 2253/112* (2013.01); *B01D 2253/116* (2013.01); *B01D 2256/245* (2013.01); *B01D 2257/102* (2013.01); *B01D 2257/702* (2013.01)

(56) References Cited

U.S. PATENT DOCUMENTS

| | | |
|---|---|---|
| 2018/0024112 A1 | 1/2018 | Chang et al. |
| 2019/0039015 A1 | 2/2019 | Long et al. |
| 2019/0060867 A1 | 2/2019 | Long et al. |
| 2019/0126237 A1 | 5/2019 | Weston et al. |

FOREIGN PATENT DOCUMENTS

| | | | | |
|---|---|---|---|---|
| WO | WO 2016/088106 A1 | 6/2016 | | |
| WO | WO-2017048795 A1 * | 3/2017 | ............. | C08F 10/02 |
| WO | WO 2017/059130 A2 | 4/2017 | | |
| WO | WO 2017/173362 A1 | 10/2017 | | |
| WO | WO 2018/152438 A1 | 8/2018 | | |

OTHER PUBLICATIONS

Carson et al., "Framework Isomerism in Vandium Metal-Organic Frameworks: MIL-88B(V) and MIL-101 (V)" Crystal Growth & Design, Oct. 2, 2013, vol. 13, pp. 5036-5044.
Van Der Voort et al., Vanadium metal-organic frameworks: structures and applications, New Journal of Chemistry, Nov. 4, 2013, vol. 38, pp. 1853-1867.
Bachman et al., "M2(m-dobdc) (M = Mn, Fe, Co, Ni) metal-organic frameworks as highly selective, high-capacity adsorbents for olefin/paraffin separations," 2017, J. Am. Chem. Soc. 139, 15363-15370.
Bechlars, "High-spin ground states via electron delocalization in mixed-valence imidazoalte-bridged divanadium complexes," 2010, Nat. Chem. 2, 362-368.
Bloch et al., "Hydrocarbon separations in a metal-organic framework with open iron(II) sites," 2012, J. Am. Chem Soc. 133, 37, p. 14814.
Bloch et al., "Reversible CO binding enables tunable CO/H2 and CO/N2 separations in metal-organic frameworks with exposed divalent metal cations," 2014, J. Am. Chem. Soc. 136, 10752-10761.
Cadieu et al., "A metal-organic framework-based splitter for separating propylene from propane," 2016, Science 353, 137-140.
Cao et al., "Capture of carbon dioxide from flue gas on TEPA-grafted metal-organic framework Mg2 (dobdc)", 2013, J. Environ. Sci. 25 (10), 2081-208.
Caskey et al., "Dramatic tuning of carbon dioxide uptake via metal substitution in a coordination polymer with cylindrical pores," 2008, J. Am. Chem. Soc. 130, 10870-10871.
Caventi et al., "Separation of CH4/CO2/N2 mixtures by layered pressure swing adsorption for upgrade of natural gas," 2006, Chem. Eng. Sci. 61, 3893-3906.
Cotton et al., "Structural studies of the vanadium(II) and vanadium(III) chloride tetra hydrofuran solvates," 1983, J. Chem. Soc., Chem. Commun. 23, 1377-1378.
Cotton et al., "Four compounds containing oxo-centered trivanadium cores surrounded by six µ,η2-carboxylato groups," 1986, Inorg. Chem. 25, 3505-3512.
Denysenko et al., "Elucidating gating effects for hydrogen sorption in MFU-4-type triazolate-based metal—organic frameworks featuring different pore sizes," 2011, Chem. Eur. J. 17, 1837-1848.
Denysenko et al., "Scorpionate-type coordination in MFU-4I metal—organic frameworks: small-molecule binding and activation upon the thermally activated formation of open metal sites," 2014, Angew. Chem., Int. Ed. 53, 5832-5836.
Edema et al., "Novel vanadium (II) amine complexes: a facile entry in the chemistry of divalent vanadium, Synthesis and characterization of mononuclear L4VCl2 [L= amine, pyridine]: X-ray structures of trans-(TMEDA)2VCl2 [TMEDA= N, N, N', N'-tetramethylethylenediamine] and trans-Mz2V(py)2 [Mz= o-C6H4CH2N(CH3)2, py= pyridine]," 1990, Inorg. Chem. 29, 1302-1306.
Fonseca et al., "$^{15}$N-NMR characterization and quantitative NMR determination of nitrogen adsorbed in MX zeolites, Porous Materials in Environmentally Friendly Processes," 1999, Surface Science DB2/ 35499110.3 43 and Catalysis 125, 229.
Furukawa et al., "The chemistry and applications of metal-organic frameworks," 2013, Science 341, p. 123044.
Gonzalez et al., "Structural characterization of framework-gas interactions in the metal—organic framework Co2(dobdc) by in situ single-crystal X-ray diffraction," 2017, Chem. Sci. 8, 4387-4398.
Herm et al., "Separation of hexane isomers in a metal—organic framework with triangular channels," 2013, Science 340, 960-962.
Kim et al., "An ethylenediamine-grafted Y zeolite: a highly regenerable carbon dioxide adsorbent via temperature swind adsorption without urea formation", 2016, Energy Environ. Sci. 9, p. 1803.
Krishna and van Baten, "In silico screening of metal—organic frameworks in separation applications," 2011, Phys. Chem. Chem. Phys. 13, 10593-10616.
Kuznicki et al., "A titanosilicate molecular sieve with adjustable pores for size-selective adsorption of molecules," 2001, Nature 412, 720-724.
Lee et al., "Design of a metal-organic framework with enhanced back bonding for separation of N2 and CH4," 2014, J. Am. Chem. Soc. 136, 698-704.
Li et al., "Selective gas adsorption and separation in metal—organic frameworks," 2009, Chem. Soc. Rev. 38, 1477-1504.
Li et al., "Introduction of pi-complexation into porous aromatic framework for highly selective adsorption of ethylene over ethane," 2014, J. Am. Chem. Soc. 136, 8654-8660.
Lokhandwala et al., "Membrane separation of nitrogen from natural gas: A case study from membrane synthesis to commercial deployment," 2010, J. Membr. Sci. 346, 270-279.
Manxzer et al., "Tetrahydrofuran complexes of selected early transition metals," 1982, Inorg. Synth., 21, 135-140.
Milner et al., "A Diaminopropane-Appended Metal—Organic Framework Enabling Efficient CO2 Capture from Coal Flue Gas via a Mixed Adsorption Mechanism", 2017, J. Am. Chem. Soc. 139, p. 13541.
Park et al., "Single ion Li+, Na+, and Mg2+ solid electrolytes supported by a mesoporous anionic Cu-azolate MOF," J. Am. Chem. Soc. 2017, 139, 38, 13260-13263.
Poloni et al., "Understanding trends in CO2 adsorption in metal—organic frameworks with open-metal sites," 2014, J. Phys. Chem. Lett. 5, 861-865.
Reed et al., "Reversible CO scavenging via adsorbate-dependent spin state transitions in an iron(II)-triazolate metal—organic framework," 2016, J. Am. Chem. Soc. 138, 5594-5602.
Reed et al., "A spin transition mechanism for cooperative adsorption in metal—rganic frameworks," 2017, Nature 550, p. 96-100.
Rieth et al., "High and reversible ammonia uptake in mesoporous azolate metal—organic frameworks with open Mn, Co, and Ni sites,:" 2016, J. Am. Chem. Soc. 138, p. 9401.

(56) References Cited

OTHER PUBLICATIONS

Siegelman, R. et al., "Controlling Cooperative CO2 Adsorption in Diamine-Appended Mg 2 (dobpdc) Metal-Organic Frameworks," Journal of the American Chemical Society, vol. 139, No. 30, Jul. 19, 2017, p. 10526-10538.
Yoon et al., "Selective nitrogen capture by porous hybrid materials containing accessible transition metal ion sites," 2017, Nat. Mater. 16, 526-531.

* cited by examiner

H₂(btdd)

VANADIUM METAL-ORGANIC FRAMEWORK FOR SELECTIVE ADSORPTION

CROSS-REFERENCE TO RELATED APPLICATION

This application claims priority to U.S. Provisional Patent Application No. 62/591,930, entitled "A Vanadium Metal-Organic Framework for Selective Adsorption," filed Nov. 29, 2017, which is hereby incorporated by reference.

STATEMENT REGARDING FEDERALLY SPONSORED RESEARCH OR DEVELOPMENT

This invention was made with government support under Grant Numbers DE-SC0001015, DE-AC02-06CH11357, DE-AC02-05CH11231 and DE-SC0016961 awarded by the Department of Energy. The government has certain rights in the invention.

FIELD OF THE PRESENT DISCLOSURE

The present application relates to vanadium containing metal-organic framework (MOF) adsorbents that selectively capture $\pi$-acids, such as is $N_2$, ethylene, propylene, acetylene, CO or $H_2$, the synthesis of such adsorbents, and applications that make use of such adsorbents.

BACKGROUND

The pervasiveness of $\pi$-acidic gases in industrial processes indicates that an adsorbent capable of selectively backbonding to these gases would have several important applications in chemical separations. For instance, natural gas, composed primarily of methane, has many potential uses as a cleaner and more renewable source of energy than other fossil fuels. See, Moniz et al., 2011, "The future of natural gas.," MIT: Cambridge, Mass. In processing steps to create high-purity methane from its various sources, however, the removal of the dinitrogen remains a significant energetic cost. See, Rufford et al., 2012, "The removal of $CO_2$ and $N_2$ from natural gas: a review of conventional and emerging process technologies," J. Petrol. Sci. Eng. 94, p. 123; and Alvarado et al., 1996, "Nitrogen removal from low quality gas," SRI International. As the demand for natural gas continues to increase, so will the need for more effective natural gas upgrading. In particular, around twenty percent of the natural gas reserves of the United States contain high levels of $N_2$. Moreover, more than twenty percent of the natural gas reserves of the United States fails to satisfy pipeline processing requirements that call for less than four percent $N_2$. Using natural gas from renewable sources also encounters the problem of high levels of $N_2$ contamination.

A substantial cost and energy sink occurs with the removal of $N_2$, as the standard method is through energetically costly cryogenic distillation, and improvements in energy efficiency of this separation will be necessary to utilize the many available sources of methane. Switching to membrane or adsorbent-based technologies could potentially alleviate this concern. See, U.S. Department of Energy, 2005, "Materials for Separation Technology: Energy and Emission Reduction Opportunities. Size selective molecular sieves (Kuznicki et al., 2001, Nature 412, p. 720) and membranes (Li et al., 2015, "SAPO-34 Membranes for $N_2/CH_4$ separation: Preparation, characterization, separation performance and economic evaluation," J. Membr. Sci. 487, p. 141) have demonstrated some ability for separating $N_2$ from $CH_4$, but face problems with scalability and selectivity, and current adsorbents need significant improvements in selectivity and capacity for $N_2$ to be commercially viable.

The utilization of solid adsorbents promises to be a central strategy toward mitigating the high energy and emission costs associated with current industrial chemical separations. See, U.S. Department of Energy. Materials Separation Technology: Energy and Emission Reduction Opportunities (2005); and Sholl and Lively, 2016, "Seven chemical separations to change the world," Nature 532, 435-438 (2016). Developing new porous materials with varying functionalities to affect selective capture in gas purification processes is needed to implement this strategy. While most industrial separations exploit volatility differences to impart selectivity, requiring operation under energetically costly conditions, porous materials can separate gases based on various chemical properties, enabling operation at more relevant pressures and temperatures. See, U.S. Department of Energy. Materials Separation Technology: Energy and Emission Reduction Opportunities (2005). However, current adsorbent materials typically only utilize differences in polarizability, size, or shape, and adsorbent-based technologies for mixtures that lack these particular chemical handles remain largely ineffective. Many industrially relevant gases, such as $H_2$, $N_2$, $O_2$, olefins, acetylene, and carbon monoxide, feature accessible $\pi^*$ orbitals capable of accepting electron density, but a suitable technology that effectively leverages this property does not exist. For instance, to date, a suitable material with a high density of the proper binding sites for removal of $N_2$ has not been demonstrated. Designing adsorbents to selectively bind $N_2$ and other $\pi$-acidic gases is challenging, as such gases are typically inert and have little interaction with most materials.

Accordingly, what is needed in the art are compositions and methods for removal of $\pi$-acidic gases in industrial processes. In the case of natural gas, such compositions and methods would reduce the energetic cost of creating high-purity methane from its various natural sources, including by the removal of dinitrogen from natural gas sources.

SUMMARY

The present disclosure addresses the above-identified shortcomings by providing metal organic frameworks with five-coordinate vanadium(II) centers as the primary metal node. The attainment of five-coordinate vanadium(II) centers within a novel metal-organic framework of the present disclosure combines the proper electronic configuration and orbital energy levels to effectively back-donate electron density to weak $\pi$-acids, enabling highly selective separations. This capability is demonstrated through the selective capture of $N_2$ from $CH_4$, with capacities and selectivities for $N_2$ that are significantly higher than any previously reported adsorbent. This disclosed backbonding mechanism is applicable toward other electron-accepting gases such as olefins, and selective olefin capture for olefin/paraffin separations are achieved at elevated temperatures. Ultimately, the incorporation of a high density of $\pi$-basic metal centers is envisioned as a more general design principle for the development of next-generation adsorbents that exploit specific orbital interactions to impart selectivity.

The electronic properties of these five-coordinate V(II) centers make this class of metal organic frameworks uniquely reactive towards relatively inert and weak electron acceptors, such as nitrogen, creating a stronger $M-N_2$ interaction than any known metal-organic framework. Additionally, the high-density of V(II) centers translates to a high gas uptake capacity, qualifying this class of material as $N_2/CH_4$ selective adsorbents. Moreover, performance parameters can be tuned as the building blocks used to make this class of metal organic frameworks are synthetically modifiable.

The technology of adsorbents for separation of $N_2$ from natural gas remains nascent, yet if developed can help supplant this costly bottleneck. Based on the present disclosure, the disclosed metal organic frameworks with five-coordinate vanadium(II) centers, such as $V_2Cl_{2.8}$(btdd) are suitable for such $N_2$ separations due to their high $N_2$ adsorption capacity and ease of regeneration. Additionally, given that metal organic frameworks with five-coordinate vanadium(II) centers, such as $V_2Cl_{2.8}$(btdd) shows more than ten times greater equilibrium selectivity than what is considered to be the inherent equilibrium selectivity of cryogenic distillation, the disclosed class of metal organic frameworks are strong candidate for this challenging separation.

One commercial application for the disclosed class of metal organic frameworks is separation of a highly contaminated (>30% $N_2$) low-pressure natural gas reservoir feed at ~100 psi using one or a combination of the disclosed class of metal organic frameworks in a pressure-swing adsorption method close to room temperature.

One aspect of the present disclosure provides an adsorption material, comprising a metal-organic framework comprising a plurality of vanadium sites interconnected by a plurality of organic linkers. Each respective organic linker M in the plurality of organic linkers comprises:

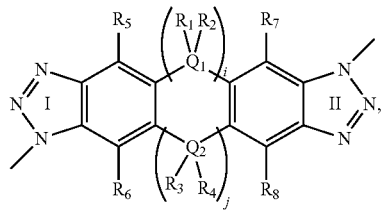

where, $Q_1$ and $Q_2$ are each independently carbon, oxygen, or nitrogen, i and j are each independently 0, 1, or 2, with the proviso that at least one $Q_1$ is carbon when i is 2 and at least one $Q_2$ is carbon when j is 2, each instance of each $R_1$, $R_2$, $R_3$, $R_4$, and $R_5$, $R_6$, $R_7$, and $R_8$ is independently H, halogen, substituted or unsubstituted alkyl, substituted or unsubstituted heteroalkyl, substituted or unsubstituted aryl, substituted or unsubstituted heteroaryl, substituted or unsubstituted heterocycloalkyl, substituted or unsubstituted alkoxy, substituted or unsubstituted arlyoxy, or substituted or unsubstituted heteroaryloxy, with the provisos that: $R_1$ and $R_2$ are not present when a $Q_1$ is oxygen, $R_3$ and $R_4$ are not present when a $Q_2$ is oxygen, one of $R_1$ and $R_2$ is not present when $Q_1$ is nitrogen, and one of $R_3$ and $R_4$ is not present when $Q_2$ is nitrogen. Furthermore, a vanadium site in the plurality of vanadium sites has a coordination of:

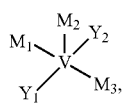

Wher $M_1$, $M_2$, $M_3$ are each a respective organic linker M in the plurality of organic linkers that binds to the vanadium site through a free nitrogen in the I or II ring of the respective organic linker, and $Y_1$ and $Y_2$ are each independently, chlo-rine, bromine, —$SCH_3$, —SCN, or —NR'R", wherein R' and R" are substituted or unsubstituted alkyl, or substituted or unsubstituted heteroalkyl.

In some embodiments, at least ten percent, at least twenty percent, at least thirty percent, at least forty percent, at least fifty percent, at least sixty percent, at least seventy percent, at least eighty percent, at least ninety percent, or at least ninety-eight percent of the vanadium sites in the plurality of vanadium sites have a coordination of:

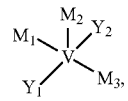

Where $M_1$, $M_2$, and $M_3$ are each a respective organic linker M in the plurality of organic linkers that binds to the vanadium site through a free nitrogen in the I or II ring of the respective organic linker M, and $Y_1$ and $Y_2$ are each independently, chlorine, bromine, —$SCH_3$, —SCN, or —NR'R", wherein R' and R" are substituted or unsubstituted alkyl, or substituted or unsubstituted heteroalkyl.

In some embodiments, $Q_1$ and $Q_2$ are each oxygen, i is one and j is one so that each respective organic linker M in the plurality of organic linkers comprises:

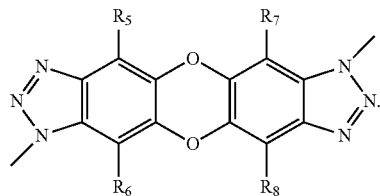

In some embodiments, i is zero and j is zero so that each respective organic linker M in the plurality of organic linkers comprises:

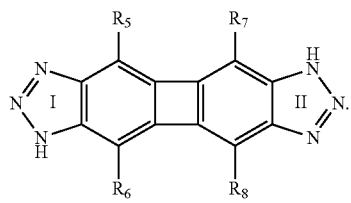

In some embodiments, $Q_1$ and $Q_2$ are each oxygen, i is 1, j is 1, and each instance of each $R_5$, $R_6$, $R_7$, and $R_8$ is independently H, halogen, substituted or unsubstituted n-alkyl or a substituted or unsubstituted branched-chain alkyl.

In some embodiments, $Q_1$ and $Q_2$ are each oxygen, i is 1, j is 1, and each instance of each $R_5$, $R_6$, $R_7$, and $R_8$ is independently H.

In some embodiments, $Y_1$ and $Y_2$ are each chlorine.

In some embodiments, the vanadium site having a coordination of:

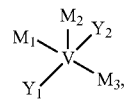

is square pyramidal, and wherein the vanadium site binds the free nitrogen in the I or II ring of each respective organic linker $M_1$, $M_2$, and $M_3$ in a meridional fashion.

Another aspect of the present disclosure provides an adsorption material, comprising a metal-organic framework comprising of vanadium sites interconnected by a plurality of organic linkers, where each respective organic linker M in the plurality of organic linkers comprises:

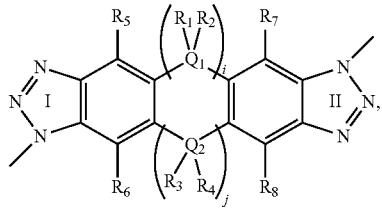

Where $Q_1$ and $Q_2$ are each independently carbon, oxygen, or nitrogen, i and j are each independently 0, 1, or 2, with the proviso that at least one $Q_1$ is carbon when i is 2 and at least one $Q_2$ is carbon when j is 2, each instance of each $R_1$, $R_2$, $R_3$, $R_4$, and $R_5$, $R_6$, $R_7$, and $R_8$ is independently H, halogen, substituted or unsubstituted alkyl, substituted or unsubstituted heteroalkyl, substituted or unsubstituted aryl, substituted or unsubstituted heteroaryl, substituted or unsubstituted heterocycloalkyl, substituted or unsubstituted alkoxy, substituted or unsubstituted arlyoxy, or substituted or unsubstituted heteroaryloxy, with the provisos that: $R_1$ and $R_2$ are not present when a $Q_1$ is oxygen $R_3$ and $R_4$ are not present when a $Q_2$ is oxygen, one of $R_1$ and $R_2$ is not present when $Q_1$ is nitrogen, and one of $R_3$ and $R_4$ is not present when $Q_2$ is nitrogen; and wherein a vanadium site in the plurality of vanadium sites has a coordination of:

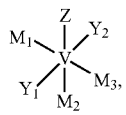

Where $M_1$, $M_2$, $M_3$ are each a respective organic linker M in the plurality of organic linkers that binds to the vanadium site through a free nitrogen in the I or II ring of the respective organic linker, $Y_1$ and $Y_2$ are each independently, chlorine, bromine, —$SCH_3$, —SCN, or —NR'R", wherein R' and R" are substituted or unsubstituted alkyl, or substituted or unsubstituted heteroalkyl, and Z is a π-acid (e.g., $N_2$, ethylene, propylene, acetylene, CO or $H_2$).

In some embodiments, at least ten percent, at least twenty percent, at least thirty percent, at least forty percent, at least fifty percent, at least sixty percent, at least seventy percent, at least eighty percent, at least ninety percent, or at least ninety-eight percent have a coordination of:

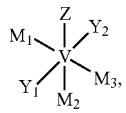

where $M_1$, $M_2$, and $M_3$ are each a respective organic linker M in the plurality of organic linkers that binds to the vanadium site through a free nitrogen in the I or II ring of the respective organic linker M, $Y_1$ and $Y_2$ are each independently, chlorine, bromine, —$SCH_3$, —SCN, or —NR'R", wherein R' and R" are substituted or unsubstituted alkyl, or substituted or unsubstituted heteroalkyl, and Z is a π-acid.

In some embodiments, $Q_1$ and $Q_2$ are each oxygen, i is one and j is one so that each respective organic linker M in the plurality of organic linkers comprises:

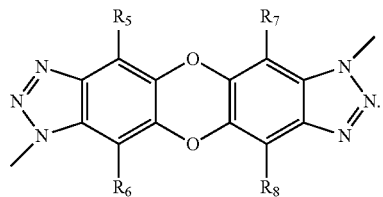

In some embodiments, i is zero and j is zero so that each respective organic linker M in the plurality of organic linkers comprises:

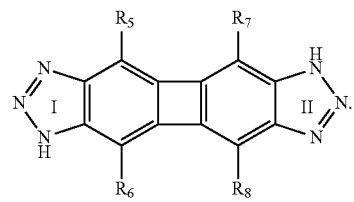

In some embodiments, $Q_1$ and $Q_2$ are each oxygen, i is 1, j is 1, and each instance of each $R_5$, $R_6$, $R_7$, and $R_8$ is independently H, halogen, substituted or unsubstituted n-alkyl or a substituted or unsubstituted branched-chain alkyl.

In some embodiments, $Q_1$ and $Q_2$ are each oxygen, i is 1, j is 1, and each instance of each $R_5$, $R_6$, $R_7$, and $R_8$ is independently H.

In some embodiments, $Y_1$ and $Y_2$ are each chlorine.

In some embodiments, the vanadium site having a coordination of:

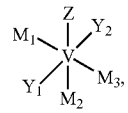

has an octahedral geometry.

Another aspect of the present disclosure provides a method of synthesizing an adsorption material. The method comprises (A) reacting a vanadium source and a ligand source in a solvent that includes an acid at a temperature of between 105° C. and 135° C. to form an intermediate product, where the vanadium source comprises $VY_2$, $VY_2$(tmeda)$_2$, $VY_2$(pyridine)$_4$, or $VY_2$($CH_3OH$)$_4$, the ligand source is $H_2$(ligand), and the ligand has the structure M:

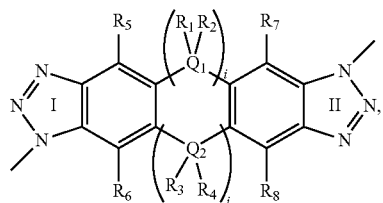

where tmeda is N,N,N',N'-tetramethylethane-1,2-diamine, Y is chlorine, bromine, —$SCH_3$, —SCN, or —NR'R", wherein R' and R" are substituted or unsubstituted alkyl, or substituted or unsubstituted heteroalkyl, $Q_1$ and $Q_2$ are each independently carbon, oxygen, or nitrogen, i and j are each independently 0, 1, or 2, with the proviso that at least one $Q_1$ is carbon when i is 2 and at least one $Q_2$ is carbon when j is 2, the free nitrogen in the I ring and the II ring each bind a hydrogen prior to the reacting, each instance of each $R_1$, $R_2$, $R_3$, $R_4$, and $R_5$, $R_6$, $R_7$, and $R_8$ is independently H, halogen, substituted or unsubstituted alkyl, substituted or unsubstituted heteroalkyl, substituted or unsubstituted aryl, substituted or unsubstituted heteroaryl, substituted or unsubstituted heterocycloalkyl, substituted or unsubstituted alkoxy, substituted or unsubstituted arlyoxy, or substituted or unsubstituted heteroaryloxy, with the provisos that: $R_1$ and $R_2$ are not present when a $Q_1$ is oxygen, $R_3$ and $R_4$ are not present when a $Q_2$ is oxygen, one of $R_1$ and $R_2$ is not present when $Q_1$ is nitrogen, and one of $R_3$ and $R_4$ is not present when $Q_2$ is nitrogen. The method further comprises (B) collecting the intermediate product and washing the intermediate product with a washing agent, and (C) activating the intermediate product to thereby form the adsorption material by heating the washed intermediate product to at least 160° C. under a vacuum; wherein the adsorption material includes a vanadium site having a coordination of:

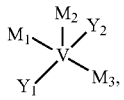

Where $M_1$, $M_2$, and $M_3$ are each a respective organic linker M in the plurality of organic linkers that binds to the vanadium site through the free nitrogen in the I or II ring of the respective organic linker M, and $Y_1$ and $Y_2$ are each independently Y.

In some embodiments, the temperature in the activating (C) is at least 170° C. In some embodiments, the temperature in the activating (C) is between 175° C. and 185° C.

In some embodiments, the reacting (A) occurs for six days or more. In some embodiments the reacting (A) occurs for seven days. In some embodiments, the reacting (A) occurs for between six days and twelve days.

In some embodiments, the activating (C) occurs for between 40 hours and 70 hours. In some embodiments, the activating (C) occurs for between 45 hours and 60 hours.

In some embodiments, the reacting (A) is done at between 115° C. and 125° C. to form the intermediate product.

In some embodiments, $Q_1$ and $Q_2$ are each oxygen, i is one and j is one such that the ligand has the structure:

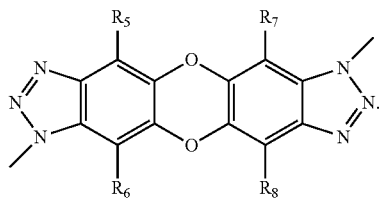

In some embodiments, $Q_1$ and $Q_2$ are each oxygen, i is 1, j is 1, and each instance of each $R_5$, $R_6$, $R_7$, and $R_8$ is independently H, halogen, substituted or unsubstituted n-alkyl or a substituted or unsubstituted branched-chain alkyl.

In some embodiments, $Q_1$ and $Q_2$ are each oxygen, i is 1, j is 1, and each instance of each $R_5$, $R_6$, $R_7$, and $R_8$ is independently H.

In some embodiments, each Y is chlorine.

In some embodiments, the acid is triflic (trifluoromethanesulfonic) acid, tosylic (p-Toluenesulfonic) acid, mesylic (methanesulfonic) acid, besylic (benzenesulfonic) acid, polystyrene sulfonic acid, ethanesulfonic acid, hydrochloric acid (HCl), hydrobromic acid (HBr), or chromic acid ($H_2CrO_4$), or a combination thereof.

In some embodiments, the solvent comprises dimethylformamide (DMF), N,N'-dimethylactamide (DMA), N,N'-diethylformamide (DEF), N,N-dimethylmethoxyacetamide, dimethylsulfoxide, hexamethylphosphoramide, N-methyl-2-pyrrolidone, dimethyl sulfone, tetramethylsulfone, or a combination thereof.

In some embodiments, the vanadium site having a coordination of:

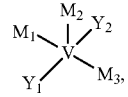

is square pyramidal, and the vanadium site binds the free nitrogen in the I or II ring of each respective organic linker $M_1$, $M_2$, and $M_3$ in a meridional fashion.

Another aspect of the present disclosure provides a metal-organic framework comprising a plurality of vanadium sites interconnected by a plurality of organic linkers, where each respective organic linker M in the plurality of organic linkers comprises:

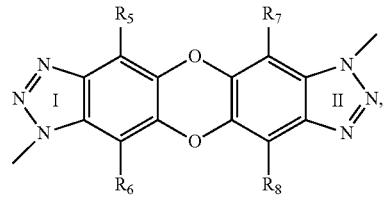

Where each instance of each $R_1$, $R_2$, $R_3$, and $R_4$, is independently H, halogen, substituted or unsubstituted alkyl, substituted or unsubstituted heteroalkyl, substituted or unsubstituted aryl, substituted or unsubstituted heteroaryl, substituted or unsubstituted heterocycloalkyl, substituted or unsubstituted alkoxy, substituted or unsubstituted arlyoxy, or substituted or unsubstituted heteroaryloxy, and where a vanadium site in the plurality of vanadium sites has a coordination of

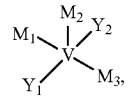

where, $M_1$, $M_2$, and $M_3$ are each a respective organic linker M in the plurality of organic linkers that binds to the vanadium site through a free nitrogen in the I or II ring of the respective organic linker M, and $Y_1$ and $Y_2$ are each independently, chlorine, bromine, —$SCH_3$, —SCN, or —NR'R", wherein R' and R" are substituted or unsubstituted alkyl, or substituted or unsubstituted heteroalkyl. In some such embodiments, at least ten percent, at least twenty percent, at least thirty percent, at least forty percent, at least fifty percent, at least sixty percent, at least seventy percent, at least eighty percent, at least ninety percent, or at least ninety-eight percent of the vanadium sites in the plurality of vanadium sites have a coordination of:

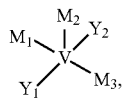

where $M_1$, $M_2$, and $M_3$ are each a respective organic linker M in the plurality of organic linkers that binds to the vanadium site through a free nitrogen in the I or II ring of the respective organic linker M, and $Y_1$ and $Y_2$ are each independently are each independently, chlorine, bromine, —$SCH_3$, —SCN, or —NR'R", wherein R' and R" are substituted or unsubstituted alkyl, or substituted or unsubstituted heteroalkyl. In some such embodiments, $Y_1$ and $Y_2$ are each chlorine.

In some such embodiments, the vanadium site having a coordination of:

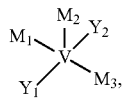

is square pyramidal, and the vanadium site binds the free nitrogen in the I or II ring of each respective organic linker $M_1$, $M_2$, and $M_3$ in a meridional fashion.

Another aspect of the present disclosure provides an adsorption material, comprising a metal-organic framework comprising a plurality of vanadium sites interconnected by a plurality of organic linkers, where each respective organic linker M in the plurality of organic linkers comprises:

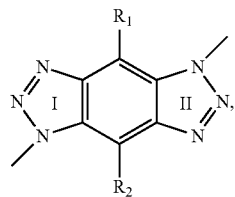

where each instance of each $R_1$, and $R_2$ is independently H, halogen, substituted or unsubstituted alkyl, substituted or unsubstituted heteroalkyl, substituted or unsubstituted aryl, substituted or unsubstituted heteroaryl, substituted or unsubstituted heterocycloalkyl, substituted or unsubstituted alkoxy, substituted or unsubstituted arlyoxy, or substituted or unsubstituted heteroaryloxy, and a vanadium site in the plurality of vanadium sites has a coordination of:

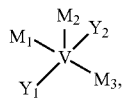

where, $M_1$, $M_2$, and $M_3$ are each a respective organic linker M in the plurality of organic linkers that binds to the vanadium site through a free nitrogen in the I or II ring of the respective organic linker M, and $Y_1$ and $Y_2$ are each independently, chlorine, bromine, —$SCH_3$, —SCN, or —NR'R", wherein R' and R" are substituted or unsubstituted alkyl, or substituted or unsubstituted heteroalkyl. In some such embodiments, at least ten percent, at least twenty percent, at least thirty percent, at least forty percent, at least fifty percent, at least sixty percent, at least seventy percent, at least eighty percent, at least ninety percent, or at least ninety-eight percent of the vanadium sites in the plurality of vanadium sites have a coordination of:

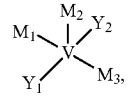

Where $M_1$, $M_2$, and $M_3$ are each a respective organic linker M in the plurality of organic linkers that binds to the vanadium site through a free nitrogen in the I or II ring of the respective organic linker M, and $Y_1$ and $Y_2$ are each independently, chlorine, bromine, —$SCH_3$, —SCN, or —NR'R", wherein R' and R" are substituted or unsubstituted alkyl, or substituted or unsubstituted heteroalkyl. In some such embodiments, $Y_1$ and $Y_2$ are each chlorine. In some such embodiments, the vanadium site having a coordination of:

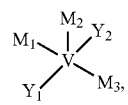

is square pyramidal, and the vanadium site binds the free nitrogen in the I or II ring of each respective organic linker $M_1$, $M_2$, and $M_3$ in a meridional fashion.

Another aspect of the present disclosure provides a method for removing $N_2$ from a biogas, natural gas, or landfill gas, the method comprising contacting the biogas, natural gas, or landfill gas with any of the adsorption materials disclosed herein to reversibly adsorb $N_2$ from the biogas thereby generating an adsorption material enriched for $N_2$ and a residual gas that is greater than ninety-eight percent pure methane. In some such embodiments, the method further comprising stripping at least fifty percent of the $N_2$ from the adsorption material enriched for $N_2$ using a regeneration method (e.g., a temperature swing adsorption method, a vacuum swing adsorption method, a pressure swing adsorption method, a concentration swing adsorption method, or a combination thereof).

Another aspect of the present disclosure provides a method of separating a n-acid from a gas produced by a source, comprising exposing the π-acid within the gas to any of the adsorption materials disclosed herein, whereby the π-acid is reversibly separated into the adsorption material. In some such embodiments, the π-acid is reversibly separated from the adsorption material by a regeneration process. In some such embodiments, the regeneration process is a temperature swing adsorption method, vacuum swing adsorption method, a pressure swing adsorption method, a concentration swing adsorption method, or a combination thereof. In some such embodiments, the π-acid is $N_2$, ethylene, propylene, acetylene, CO or $H_2$.

Another aspect of the present disclosure provides a method of separating an olefin (alkene) from a paraffin (alkane) counterpart of the olfefin in a gas, comprising exposing the olefin within the gas to any of the adsorption materials disclosed herein, whereby the olefin is reversibly separated into the adsorption material. In some such embodiments, the olefin is reversibly separated from the adsorption material by a regeneration process. In some such embodiments, the regeneration process is a temperature swing adsorption method, vacuum swing adsorption method, a pressure swing adsorption method, a concentration swing adsorption method, or a combination thereof. In some such embodiments, the olefin is ethylene and the paraffin is ethane. In some such embodiments, the olefin is propylene and the paraffin is propane.

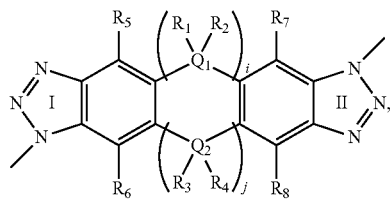

where, in the figure, only the I and II rings of each respective organic linker is shown, and where $Q_1$ and $Q_2$ are each independently carbon, oxygen, or nitrogen, i and j are each independently 0, 1, or 2, with the proviso that at least one $Q_1$ is carbon when i is 2 and at least one $Q_2$ is carbon when j is 2, each instance of each $R_1$, $R_2$, $R_3$, $R_4$, and $R_5$, $R_6$, $R_7$, and $R_8$ is independently H, halogen, substituted or unsubstituted alkyl, substituted or unsubstituted heteroalkyl, substituted or unsubstituted aryl, substituted or unsubstituted heteroaryl, substituted or unsubstituted heterocycloalkyl, substituted or unsubstituted alkoxy, substituted or unsubstituted arlyoxy, or substituted or unsubstituted heteroaryloxy, with the provisos that $R_1$ and $R_2$ are not present when a $Q_1$ is oxygen, $R_3$ and $R_4$ are not present when a $Q_2$ is oxygen, one of $R_1$ and $R_2$ is not present when $Q_1$ is nitrogen, and one of $R_3$ and $R_4$ is not present when $Q_2$ is nitrogen, and where each vanadium site (labeled "V" in the Figure) in the plurality of vanadium sites has a coordination of

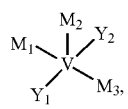

where, $M_1$, $M_2$, $M_3$ are each a respective organic linker M in the plurality of organic linkers that binds to the vanadium site through a free nitrogen (labeled "N" in the Figure) in the I or II ring of the respective organic linker, and $Y_1$ and $Y_2$ are each independently chlorine, bromine, —$SCH_3$, —SCN, or —NR'R", wherein R' and R" are substituted or unsubstituted alkyl, or substituted or unsubstituted heteroalkyl, and where the Figure further illustrates how each vanadium site is unsaturated and is square pyramidal, bound by three nitrogens in a meridional fashion, and by two halogens ($Y_1$ and $Y_2$) in accordance with an embodiment of the present disclosure.

Figure 2:
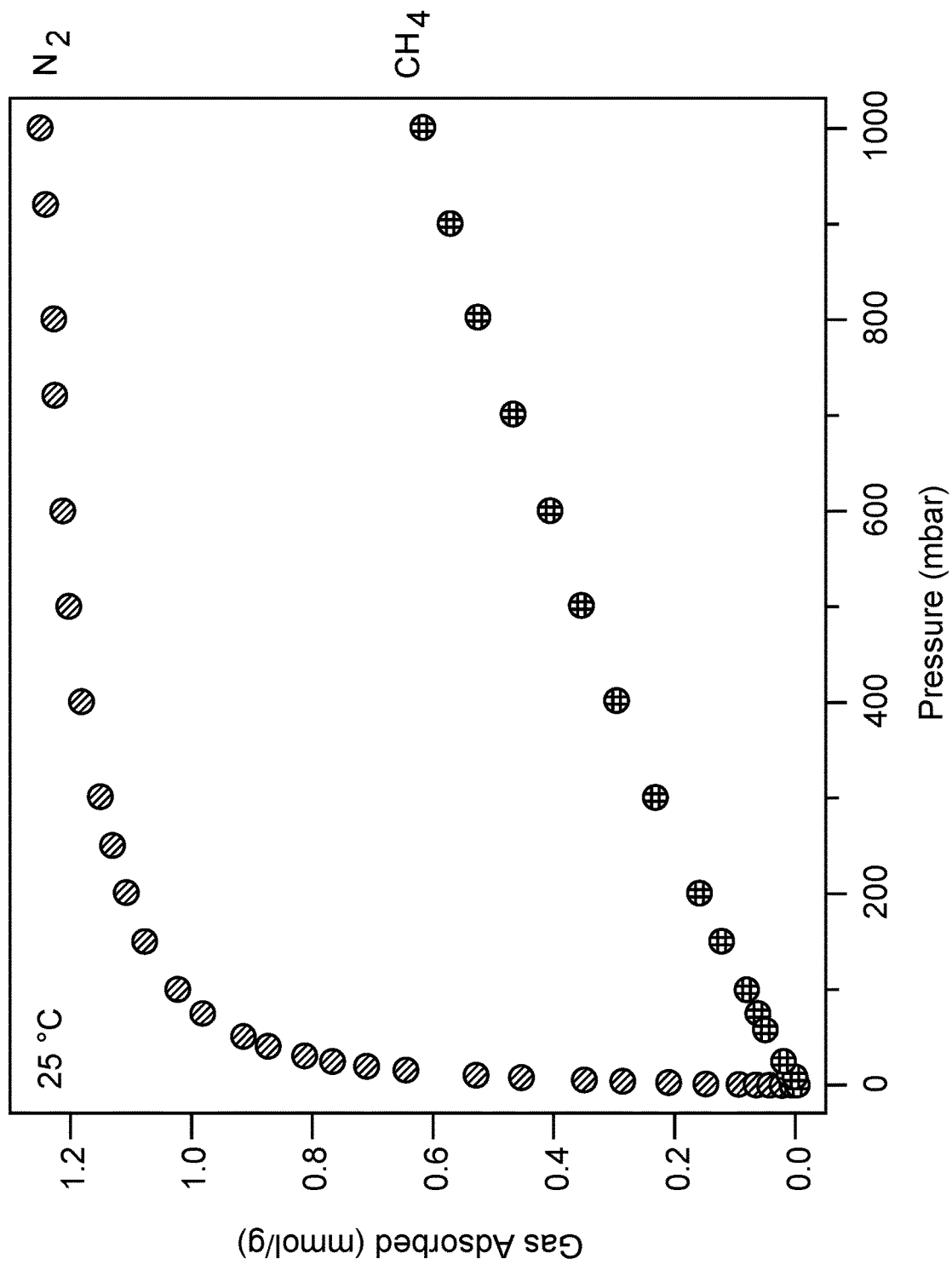

FIG. 2 illustrates gas adsorption isotherms of $N_2$ and $CH_4$ collected for $V_2Cl_{2.8}$(btdd) at 25° C., in accordance with an embodiment of the present disclosure.

Figure 3:
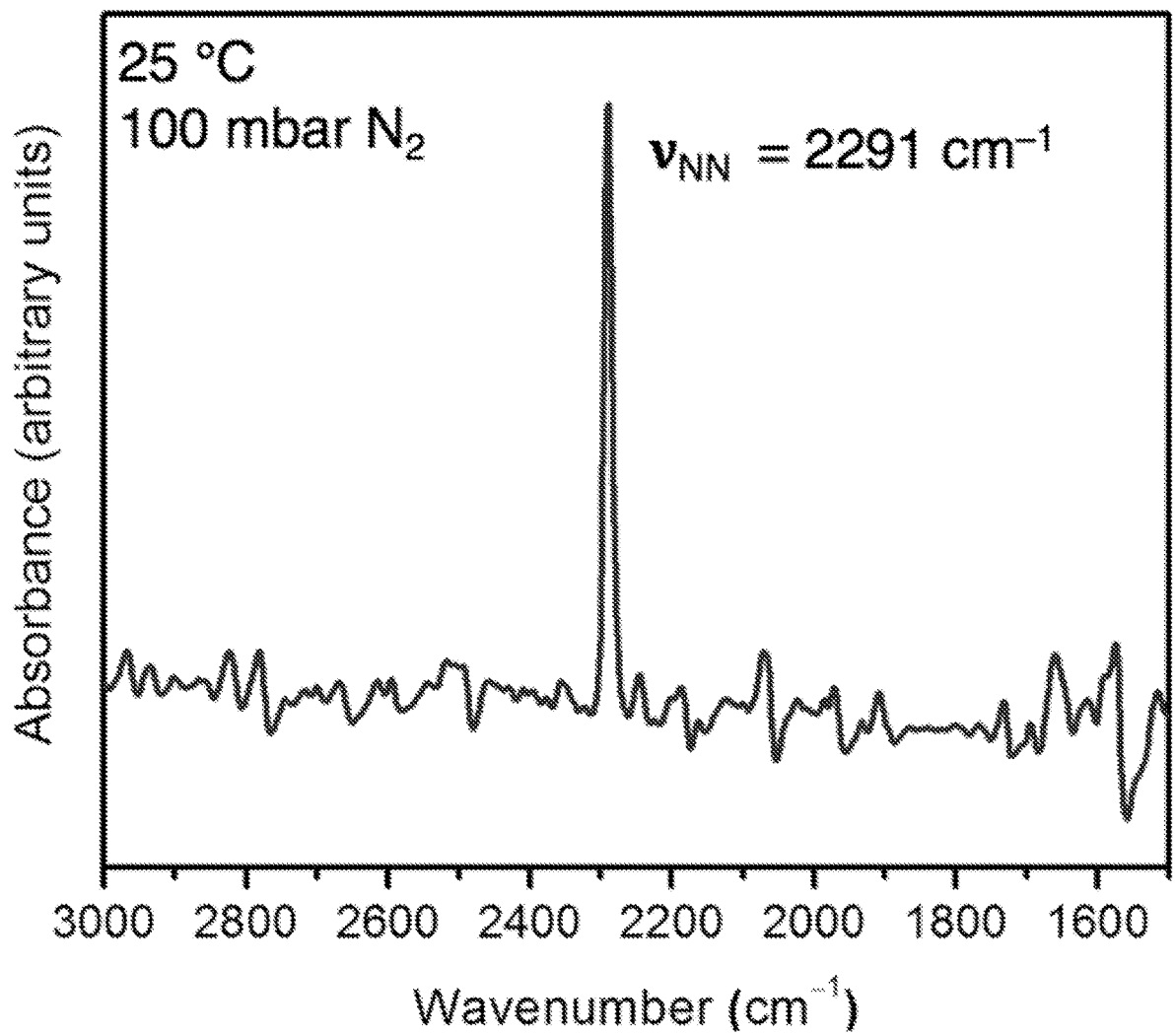

FIG. 3 illustrates an infrared spectrum collected for $V_2Cl_{2.8}$(btdd) under an atmosphere of 100 mbar of $N_2$ at 25° C., showing a red-shifted N—N stretch compared to free $N_2$, in accordance with an embodiment of the present disclosure.

Figure 4:
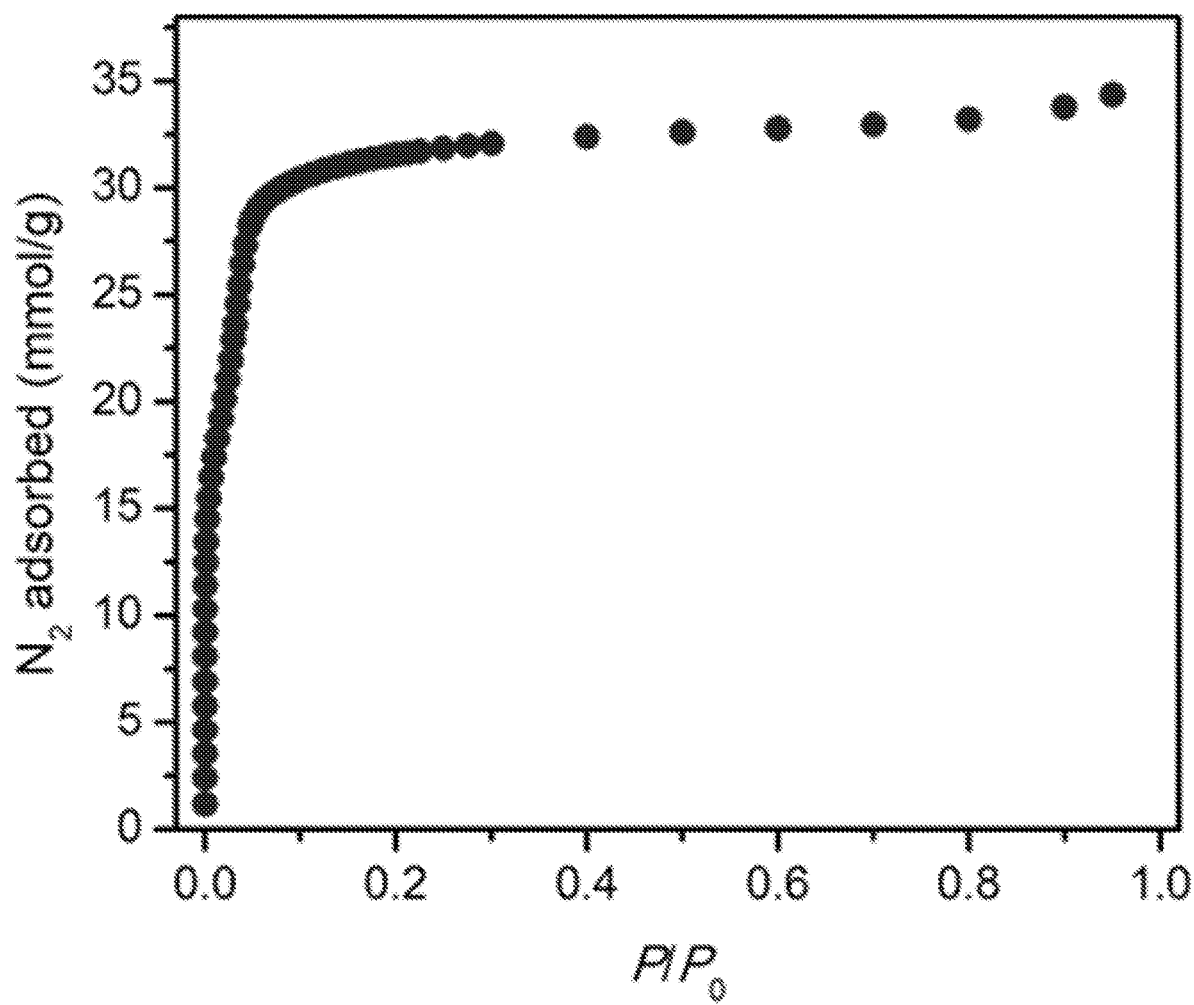

FIG. 4 illustrates an adsorption isotherm of $N_2$ collected at 77 K for $V_2Cl_{2.8}$(btdd), where $H_2$btdd=bis(1H-1,2,3-triazolo[4,5-b],[4',5'-i])dibenzo[1,4]dioxin, in accordance with an embodiment of the present disclosure.

Figure 5:
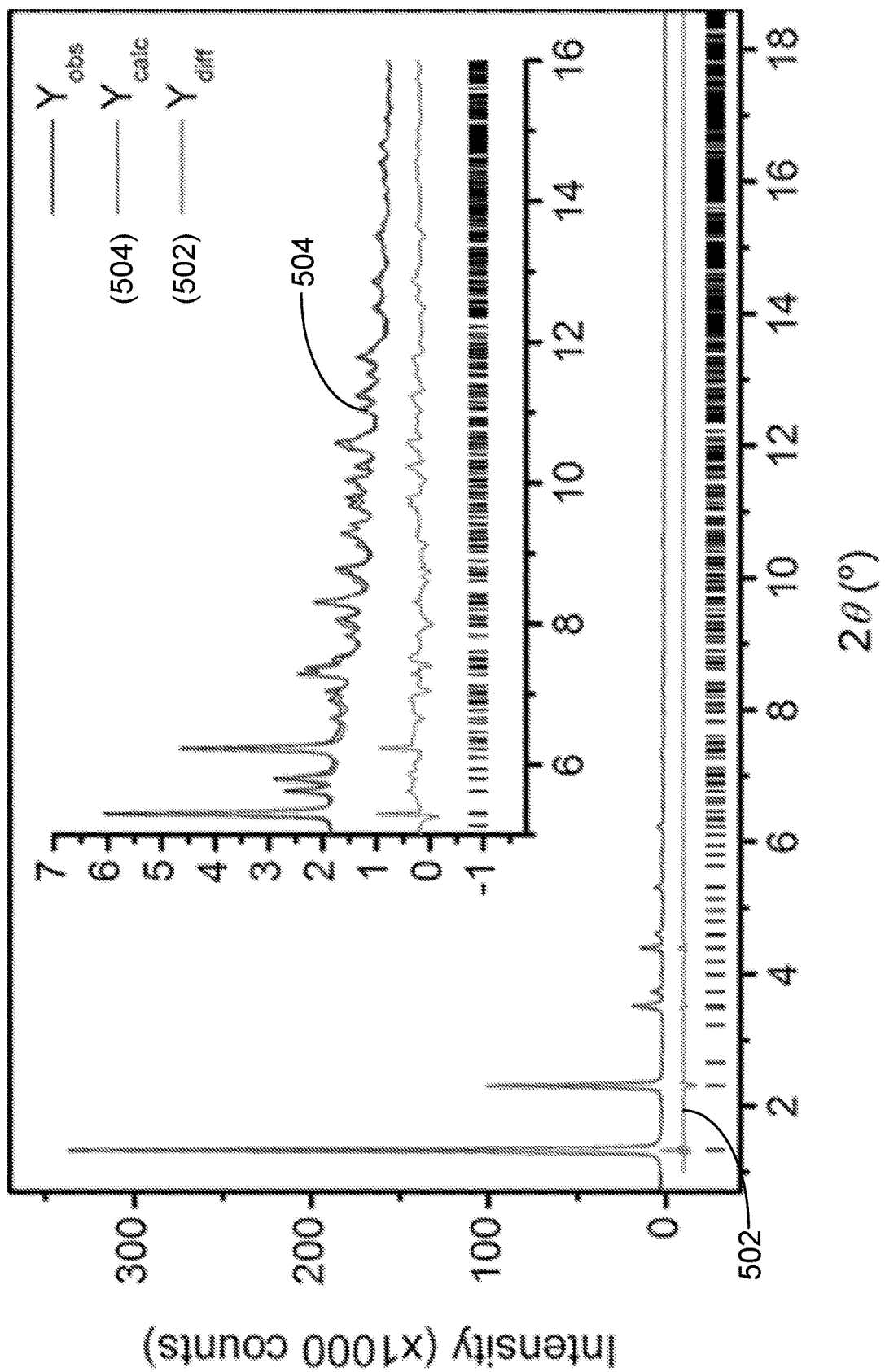

FIG. 5 illustrates Rietveld refinement of evacuated $V_2Cl_{2.8}$(btdd) measured at 298 K from 1° to 18.6°. Blue and red lines (504) represent the observed and calculated diffraction patterns, respectively. The gray line (502) represents the difference between observed and calculated patterns, and the black tick marks indicate calculated Bragg peak positions. The inset shows the high-angle region at a magnified scale. Figures-of-merit (as defined by TOPAS): $R_{wp}$=5.68%, $R_p$=3.81%, $R_{exp}$=1.87%, $R_{Bragg}$=2.17%, GoF=3.04. The wavelength of measurement was 0.45236 Å, in accordance with an embodiment of the present disclosure.

Figure 6:
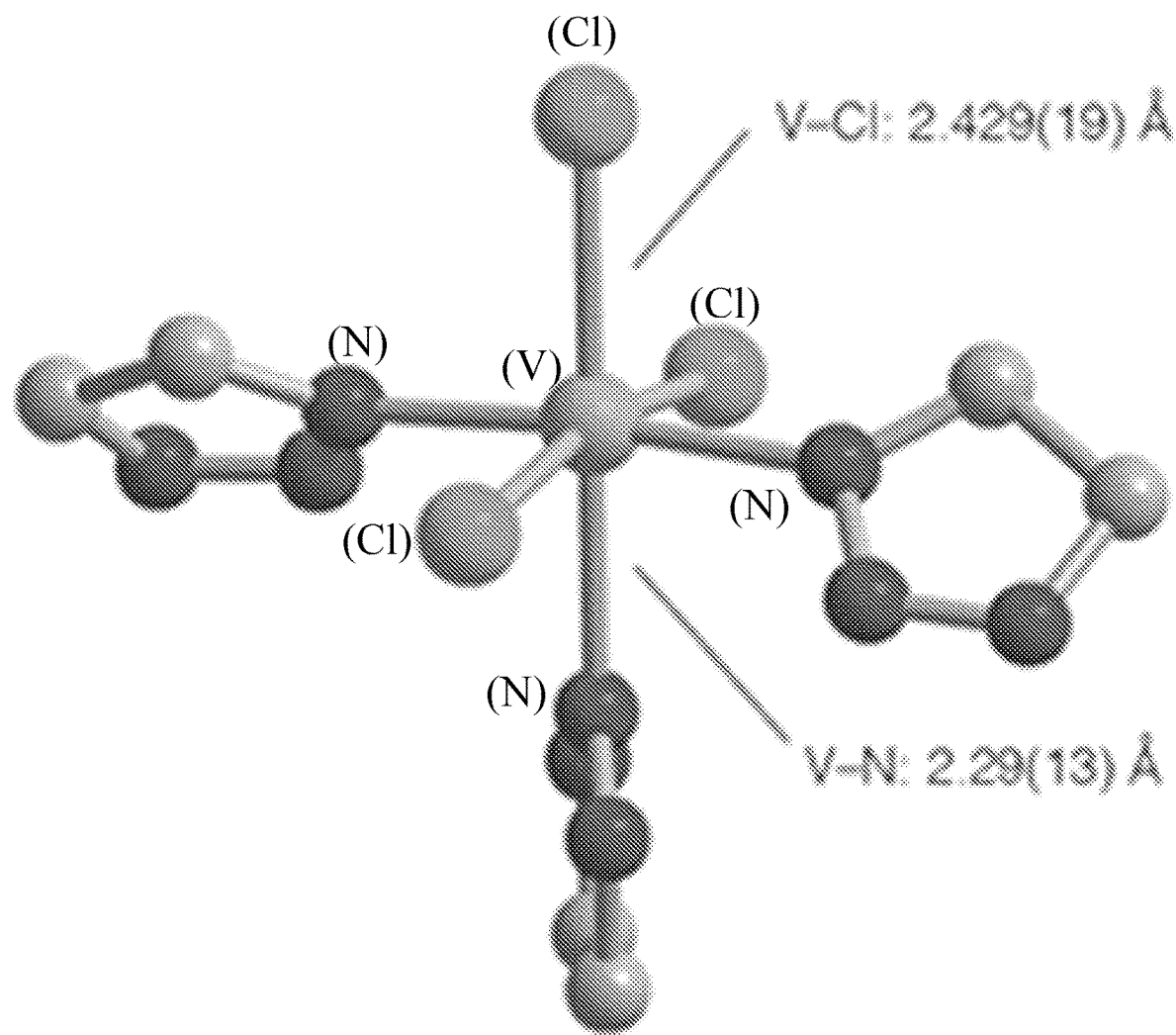

FIG. 6 illustrates the first coordination sphere of a six-coordinate vanadium(III) center with relevant bond length highlighted in which forty percent of the vanadium centers exhibit this coordination while the remaining vanadium centers are five coordinate, as described by the molecular formula $V_2Cl_{2.8}$(btdd), in accordance with an embodiment of the present disclosure.

Figure 7:
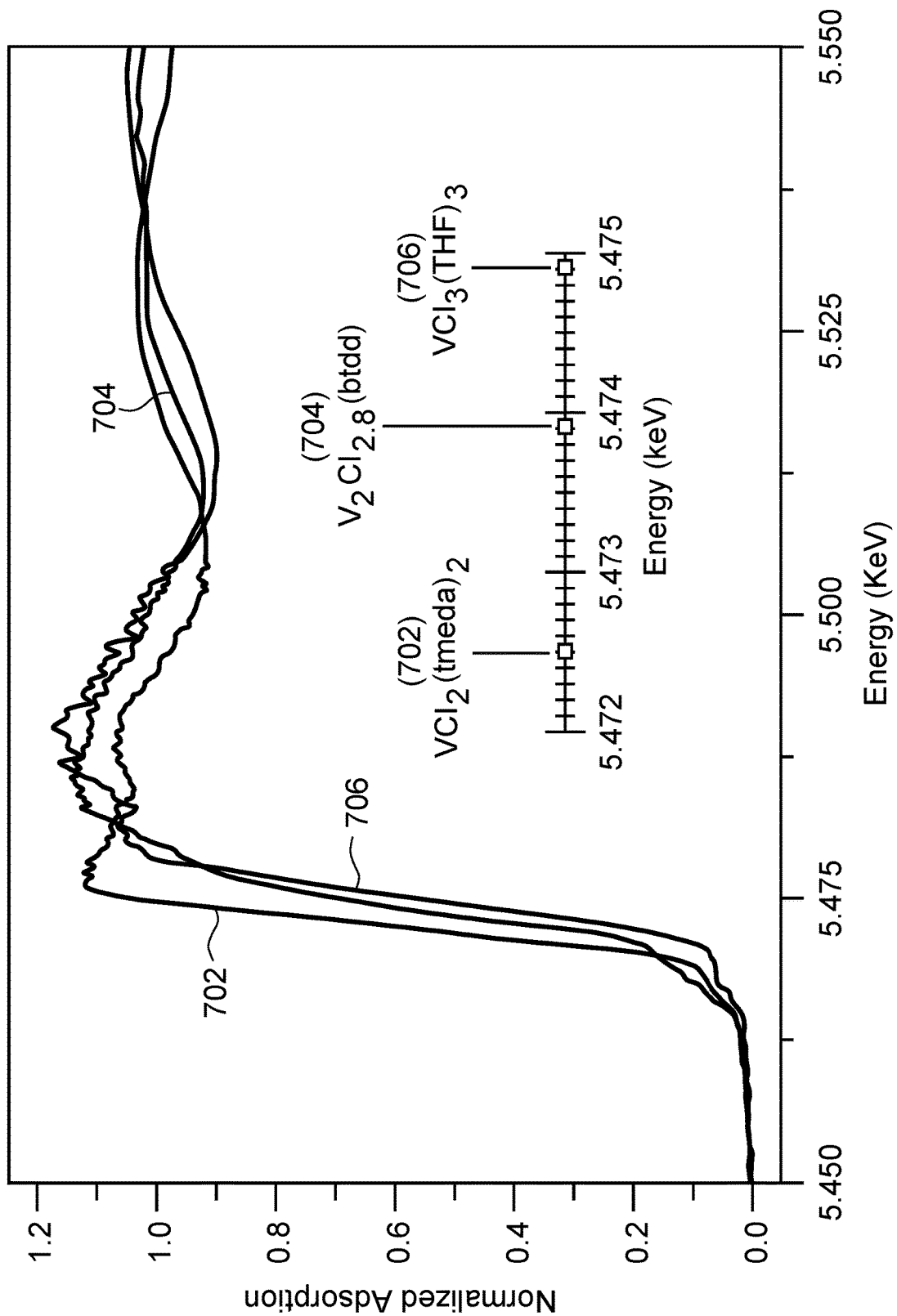

FIG. 7 illustrates vanadium K-edge X-ray absorption spectra collected for $V_2Cl_{2.8}$(btdd) (704), a vanadium(II) reference $V_2Cl_2$(tmeda)$_2$ (702), and a vanadium(III) reference $VCl_3$(tetrahydrofuran)$_3$ (706). Inset depicts edge energies determined at half-max of the rising edge.

Figure 8:
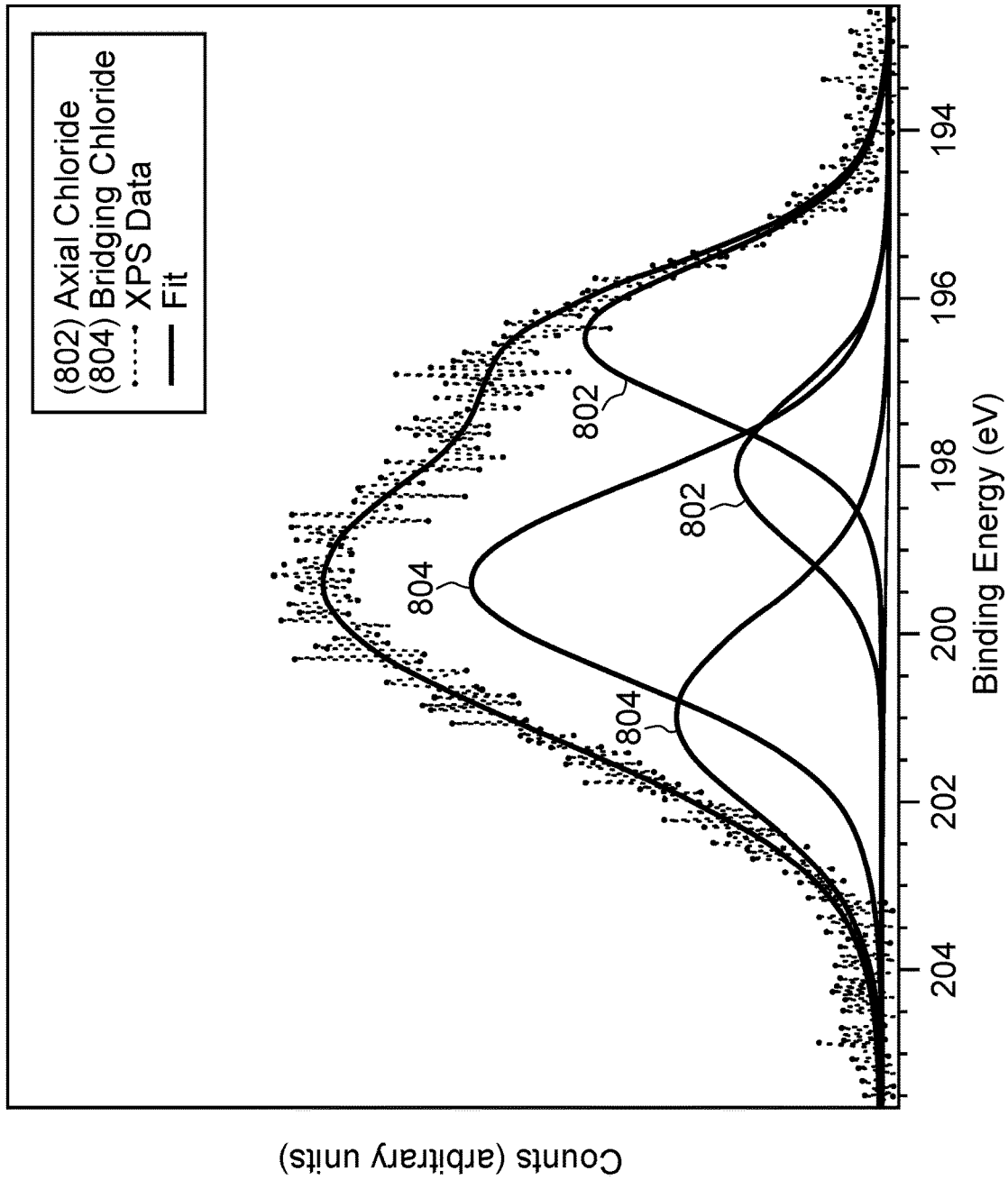

FIG. 8 illustrates chlorine X-ray photoelectron spectrum of $V_2Cl_{2.8}$(btdd). The chloride peak shape is indicative of the presence of multiple chloride species in the sample. The peak shape bears a similarity to metal halide clusters, where terminal and bridging chloride species can be resolved. See Hamer and Walton, 1974, "X-ray photoelectron spectra of inorganic molecules, IX. Distinction between bridging and terminal metal-chlorine bonds in metal halide clusters of rhenium (III) and molybdenum (II)," Inorg. Chem. 13, 1446-1451. The chloride region is fit to two distinct chloride types, which ae assigned as axial (blue) and bridging (red). For each chloride type, the contributions from the Cl $2p_{1/2}$ and Cl $2p_{3/2}$ core levels are shown.

Figure 9:
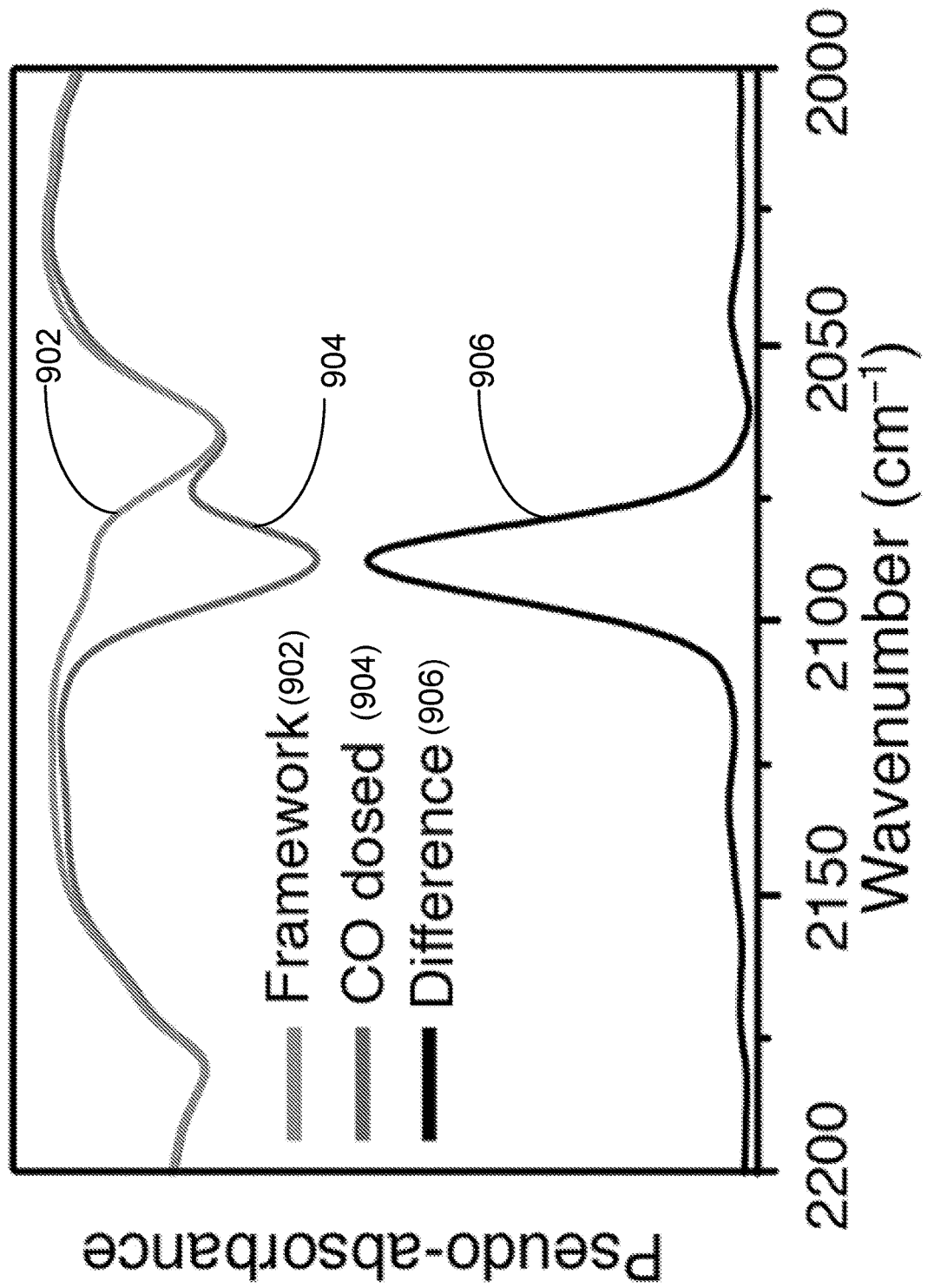

FIG. 9 illustrates 300 K infrared spectra for activated $V_2Cl_{2.8}$(btdd) (grey, 902) and $V_2Cl_{2.8}$(btdd) dosed with 33 mbar of CO (red, 904), with the difference between these two spectra shown in black (906), in accordance with an embodiment of the present disclosure.

Figure 10:
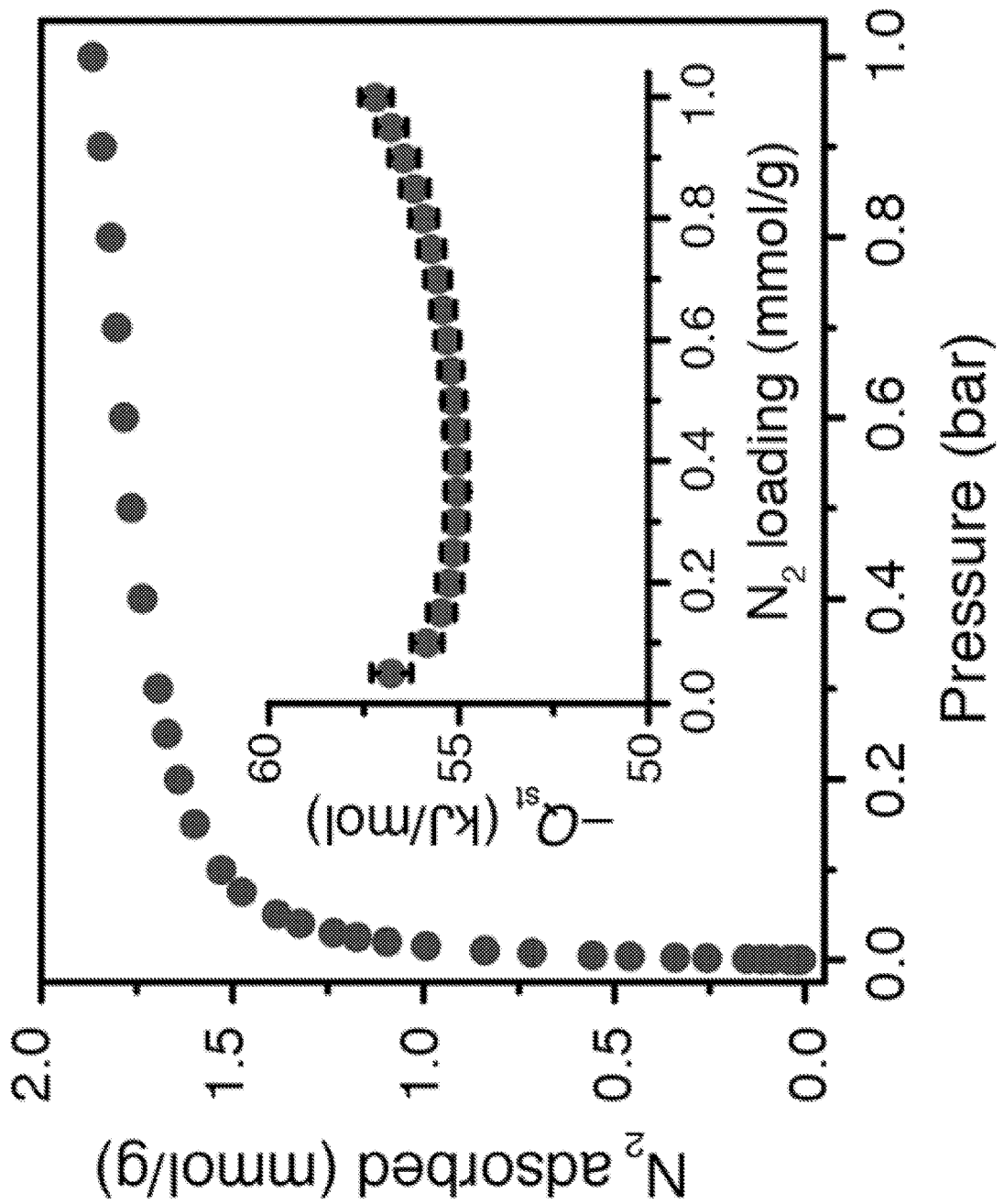

FIG. 10 illustrates adsorption isotherm of $N_2$ collected at 25° C., with the inset displaying the isosteric heat of $N_2$ adsorption (error bars are shown in black), in accordance with an embodiment of the present disclosure.

Figure 11:
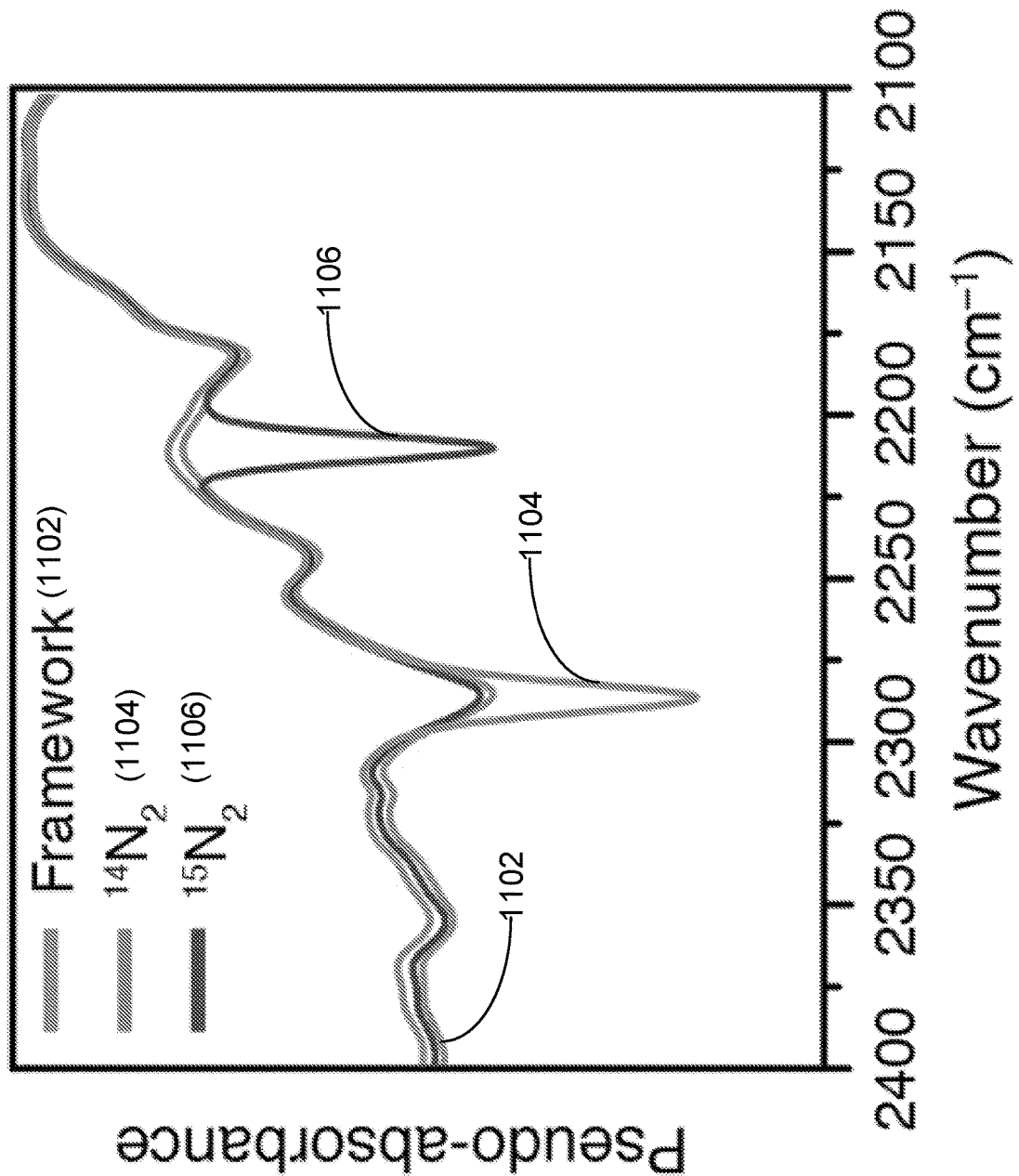

FIG. 11 illustrates the infrared spectra for $V_2Cl_{2.8}$(btdd) collected at 25° C. under vacuum (grey, 1102), dosed with 80 mbar of $^{14}N_2$ (blue, 1104), and dosed with 85 mbar of $^{15}N_2$ (cyan, 1106).

Figure 12:
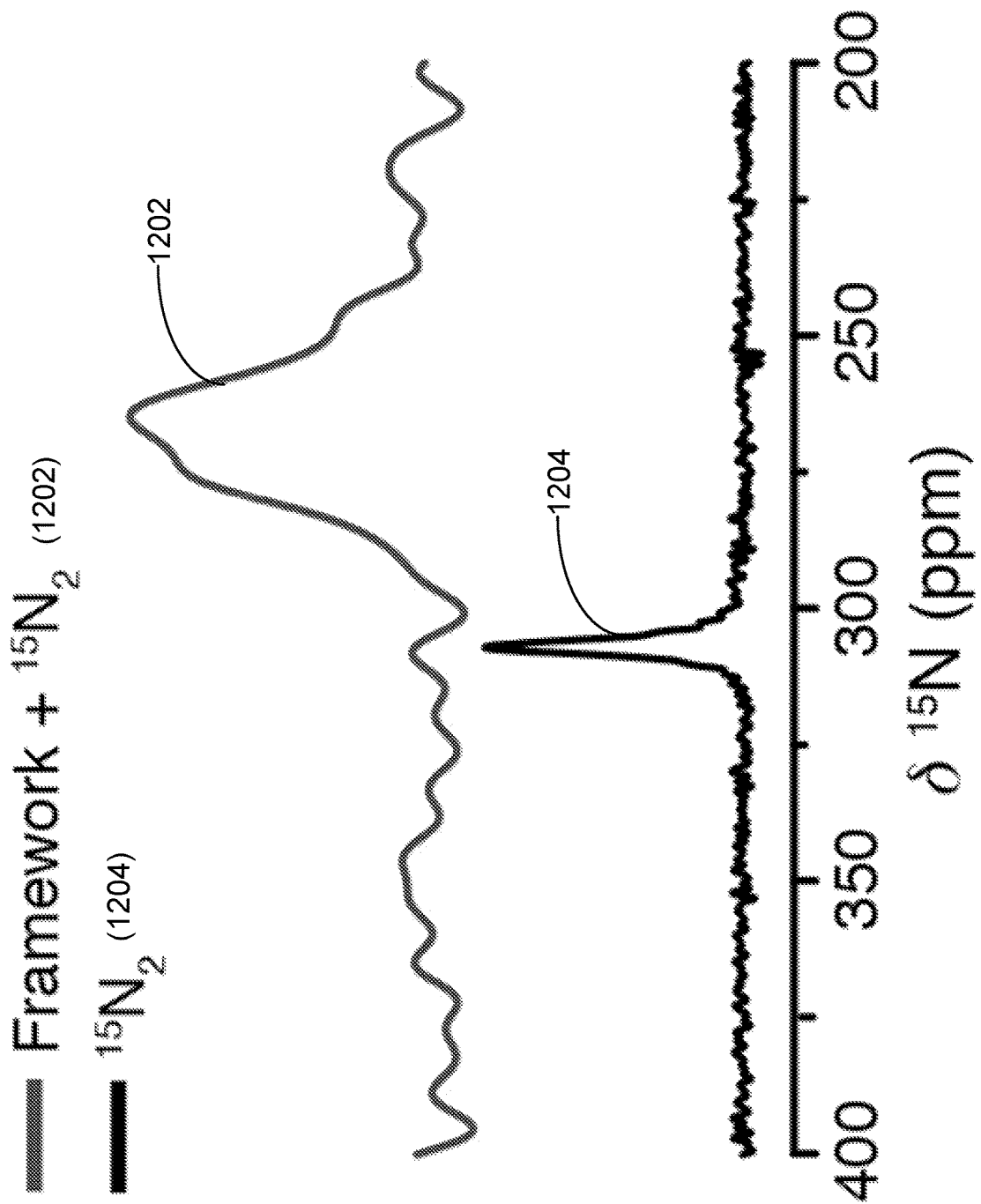

FIG. 12 illustrates $^{15}N$ nuclear magnetic resonance spectra collected for free gas-phase $^{15}N_2$ at 700 mbar (black, 1204) and $^{15}N_2$-dosed (770 mbar) $V_2Cl_{2.8}$(btdd) (blue, 1202) at room temperature, with the latter collected under magic angle spinning at 15 kHz.

Figure 13:
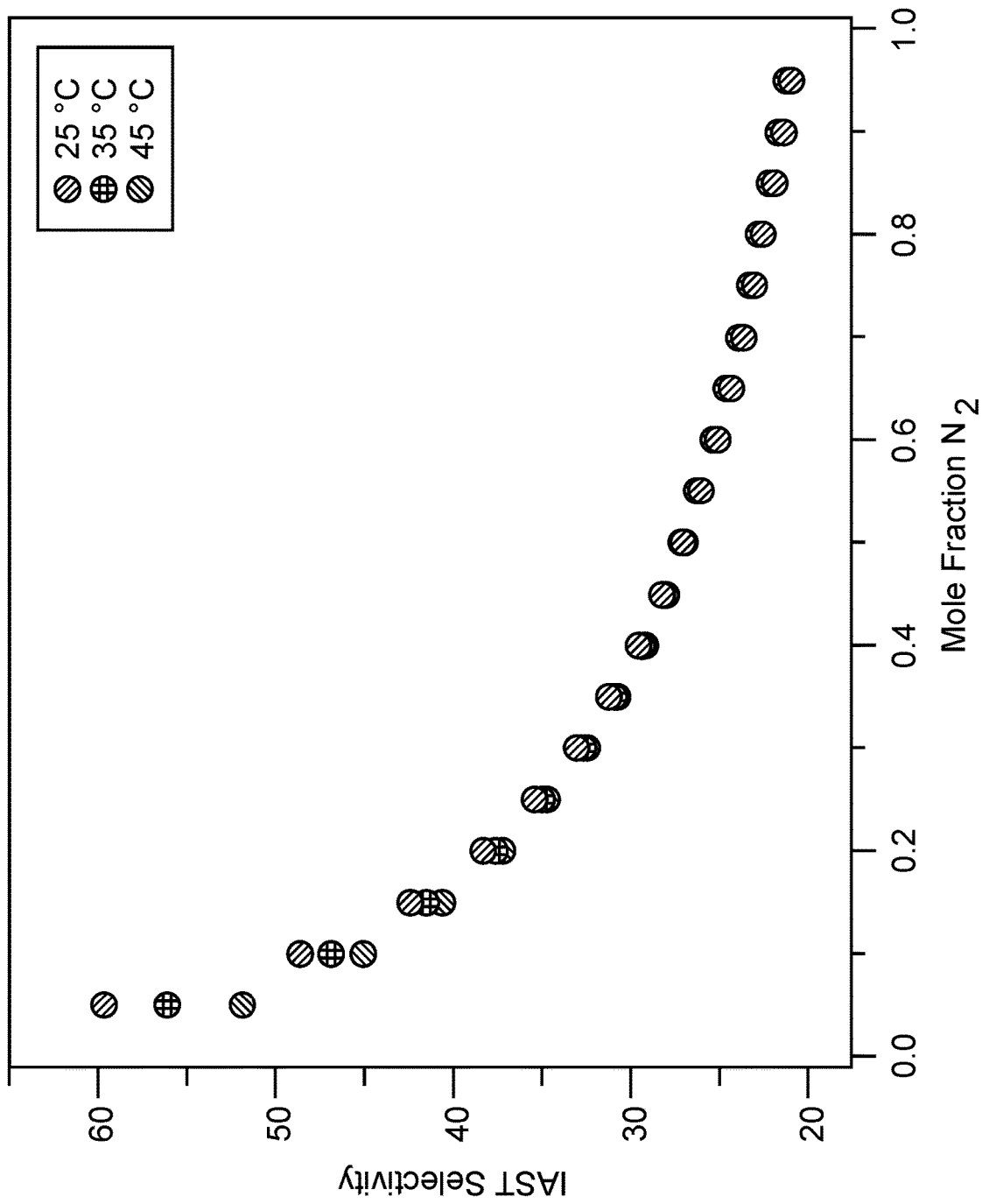

FIG. 13 illustrates IAST selectivity values collected at multiple temperatures for varying $N_2$:$CH_4$ ratios at a total pressure of 1 bar, in accordance with an embodiment of the present disclosure.

Figure 14:
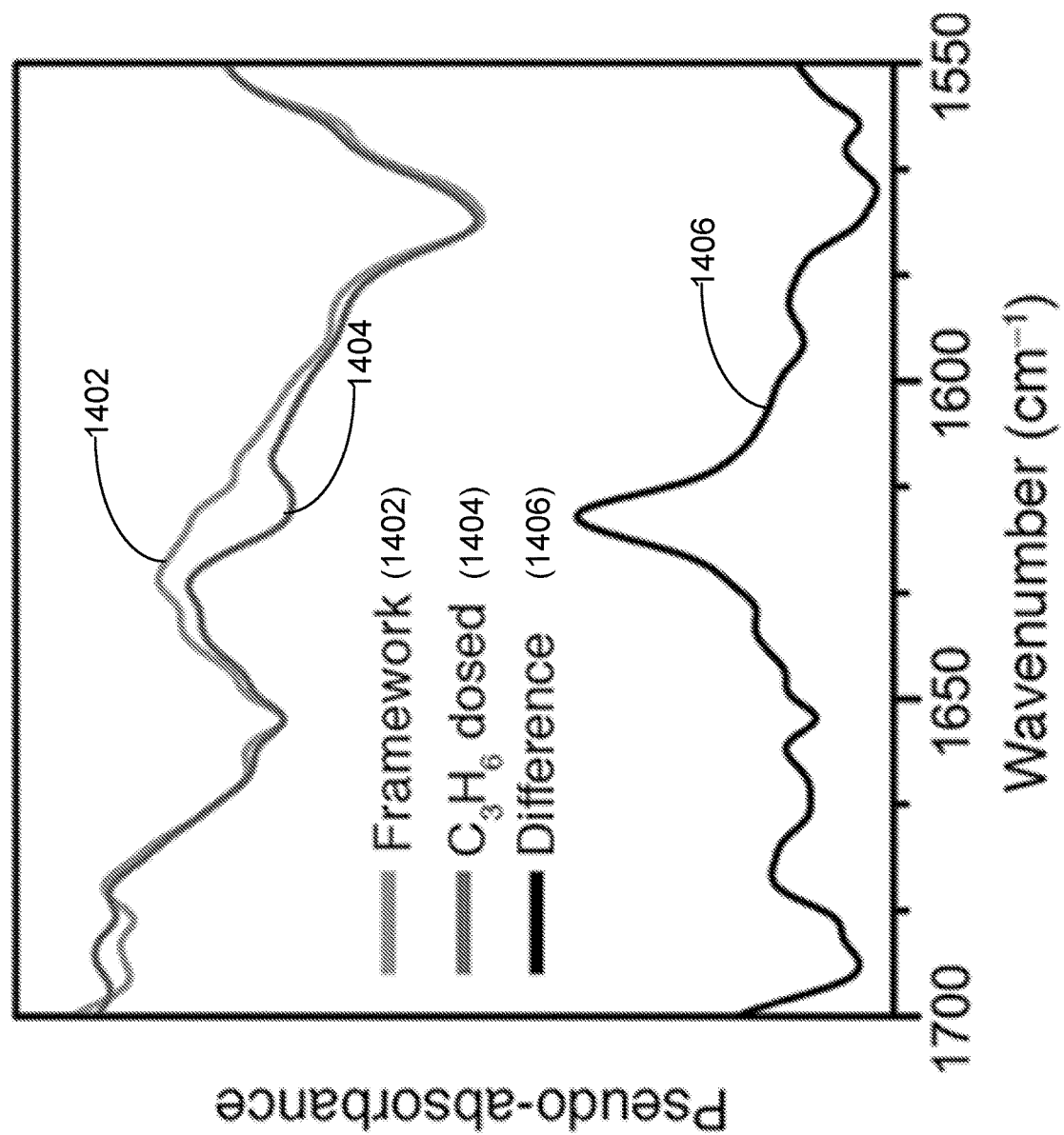

FIG. 14 illustrates 298 K infrared spectrum of $V_2Cl_{2.8}$(btdd) under vacuum (grey, 1402), dosed with 7.5 mbar of propylene (red, 1404) (not corrected for background), and the difference spectrum thereof (black, pseudo-absorbance units, 1406), with the C—C stretch of gaseous propylene occurring at 1651 $cm^{-1}$ (Lord and Venkateswarlu, 1953, "The infrared spectra of propylene and propylene-$d_6$," J. Opt. Soc. Chem., 11 1079-1085) in accordance with an embodiment of the present disclosure.

Figure 15:
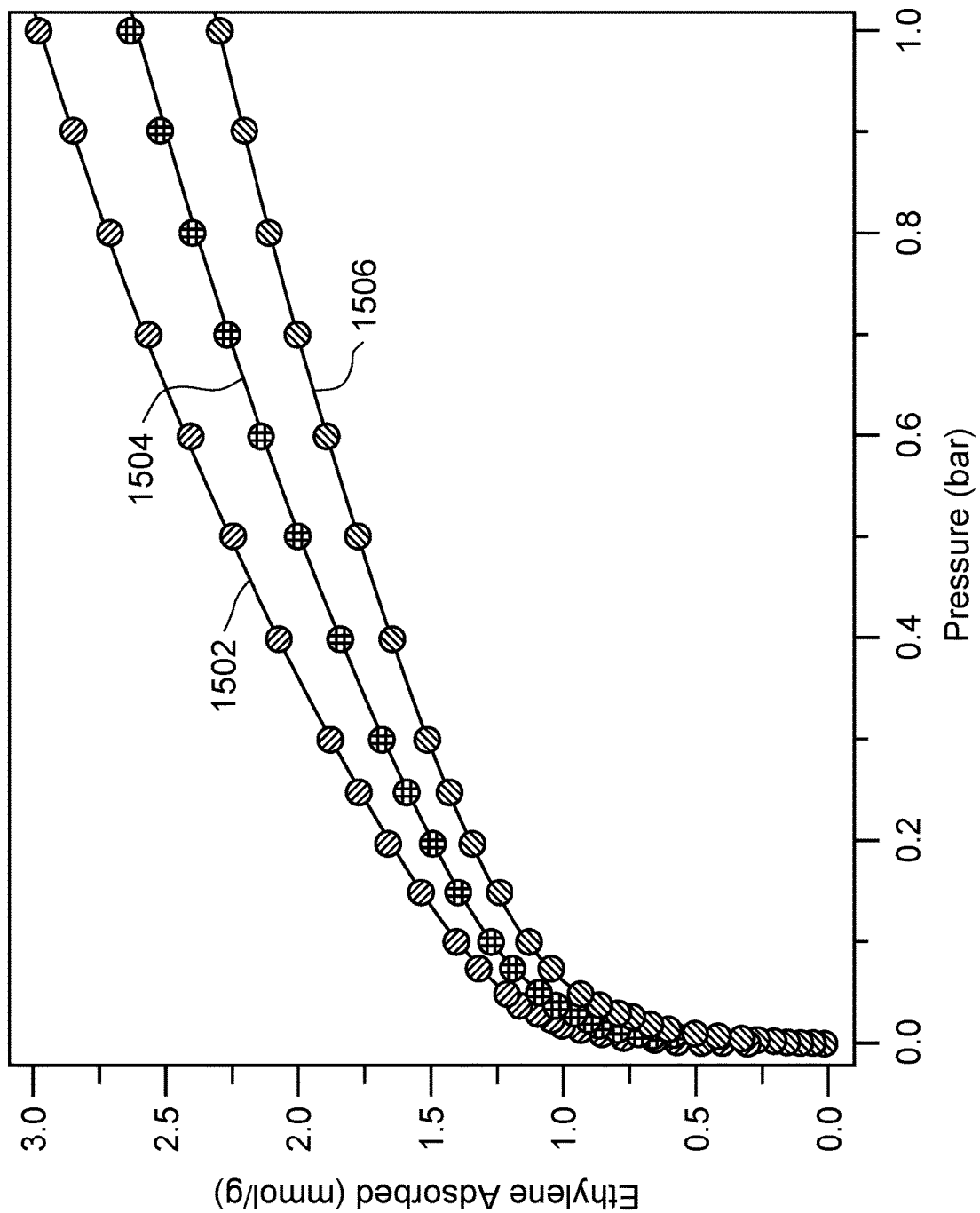

FIG. 15 illustrates adsorption isotherms of ethylene collected at 60 (blue, 1502), 70 (green, 1504), and 80° C. (red, 1506) with fits to the dual-site Langmuir-Freundlich equation shown in black lines, in accordance with an embodiment of the present disclosure.

Figure 16:
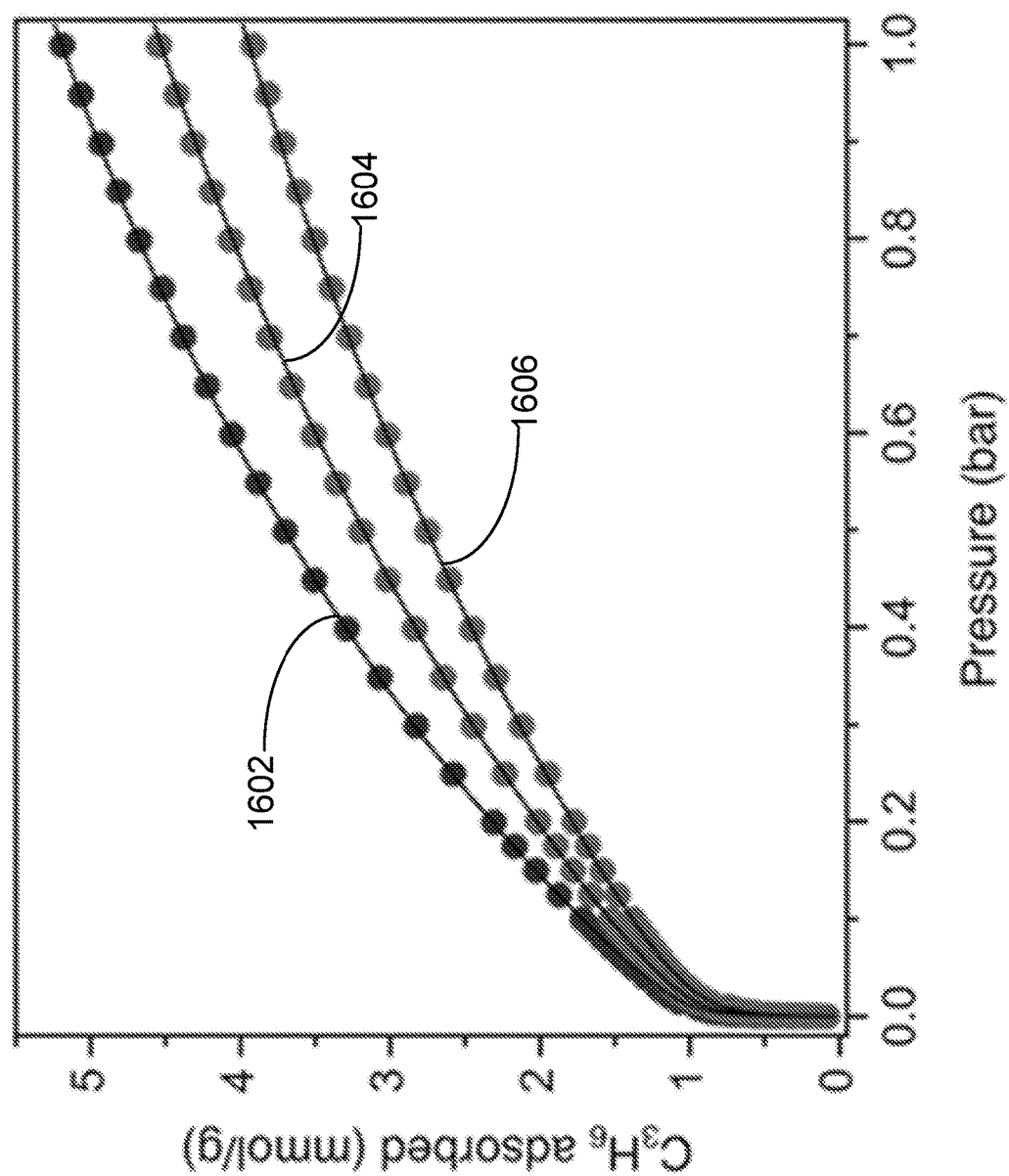

FIG. 16 illustrates adsorption isotherms of propylene collected at 60 (blue, 1602), 70 (green, 1604), and 80° C. (red, 1606) with fits to the dual-site Langmuir-Freundlich equation shown in black lines, in accordance with an embodiment of the present disclosure.

Figure 17:
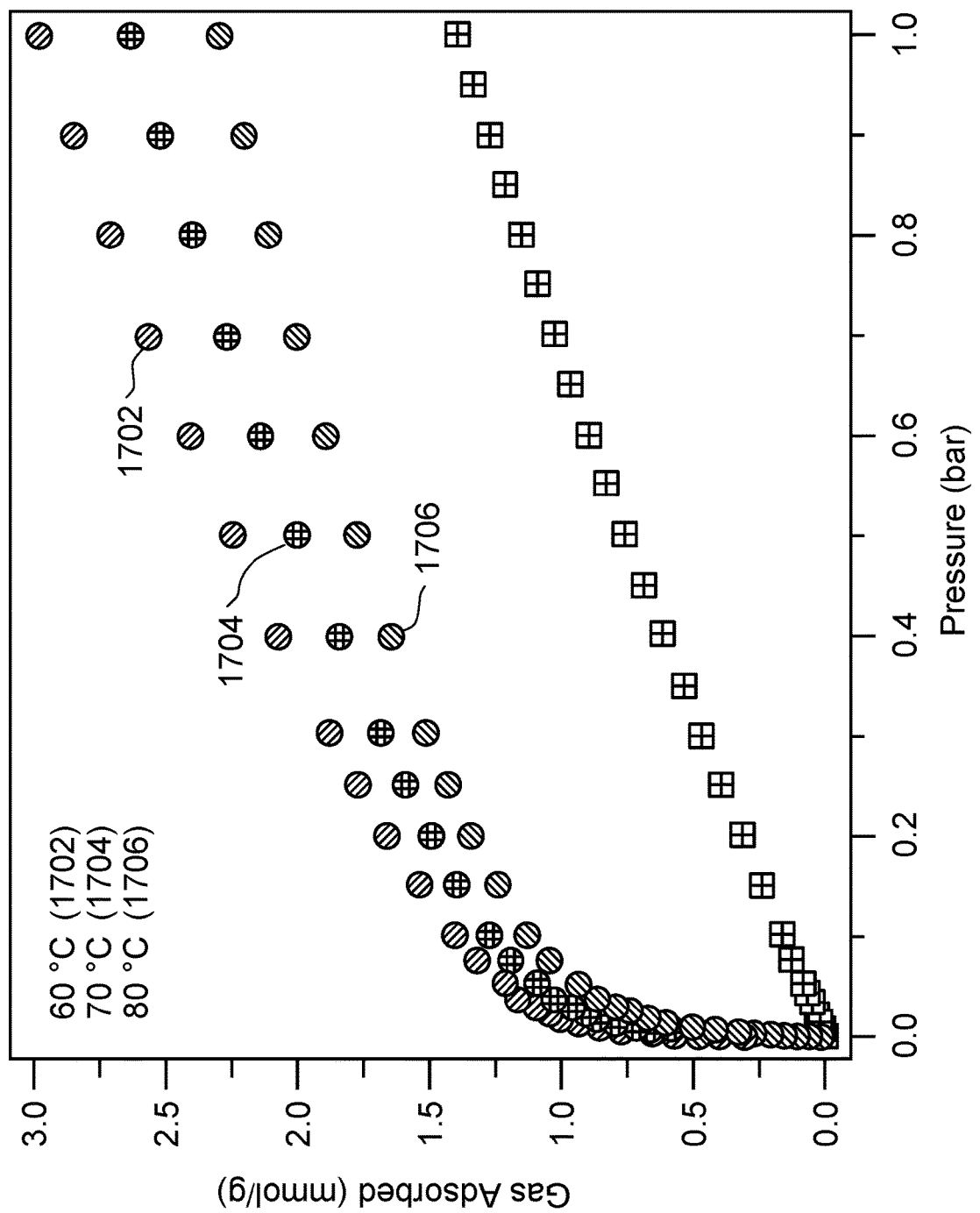

FIG. 17 illustrates high-temperature ethylene and ethane adsorption isotherms of $V_2Cl_{2.8}$(btdd), in which circles and squares represent ethylene and ethane isotherms, respectively, in accordance with an embodiment of the present disclosure.

Figure 18:
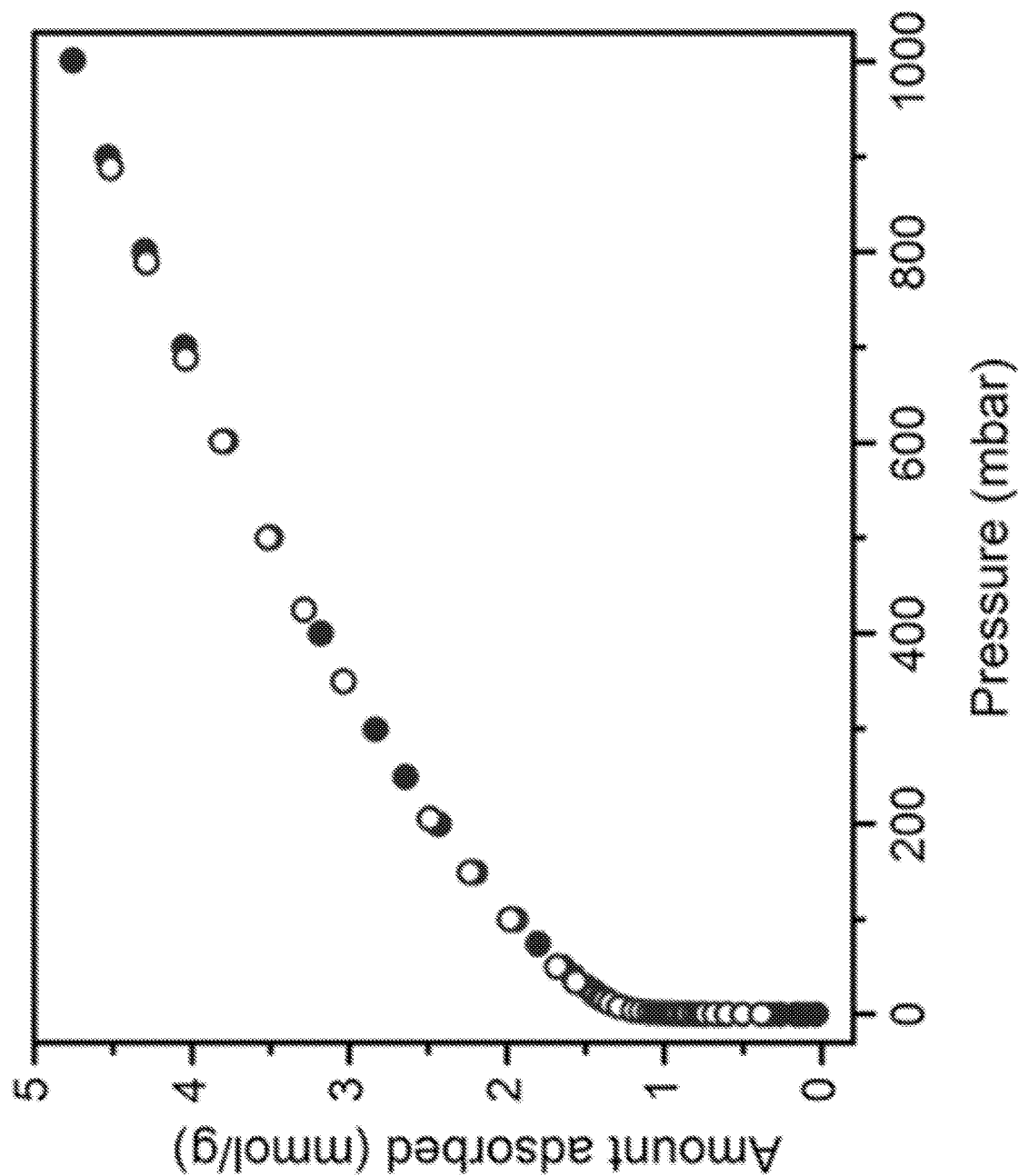

FIG. 18 illustrates ethylene adsorption (solid circles) and desorption (open circles) isotherms collected in $V_2Cl_{2.8}$(btdd) at 25° C., showing the reversible nature of the ethylene adsorption, in accordance with an embodiment of the present disclosure.

Figure 19:
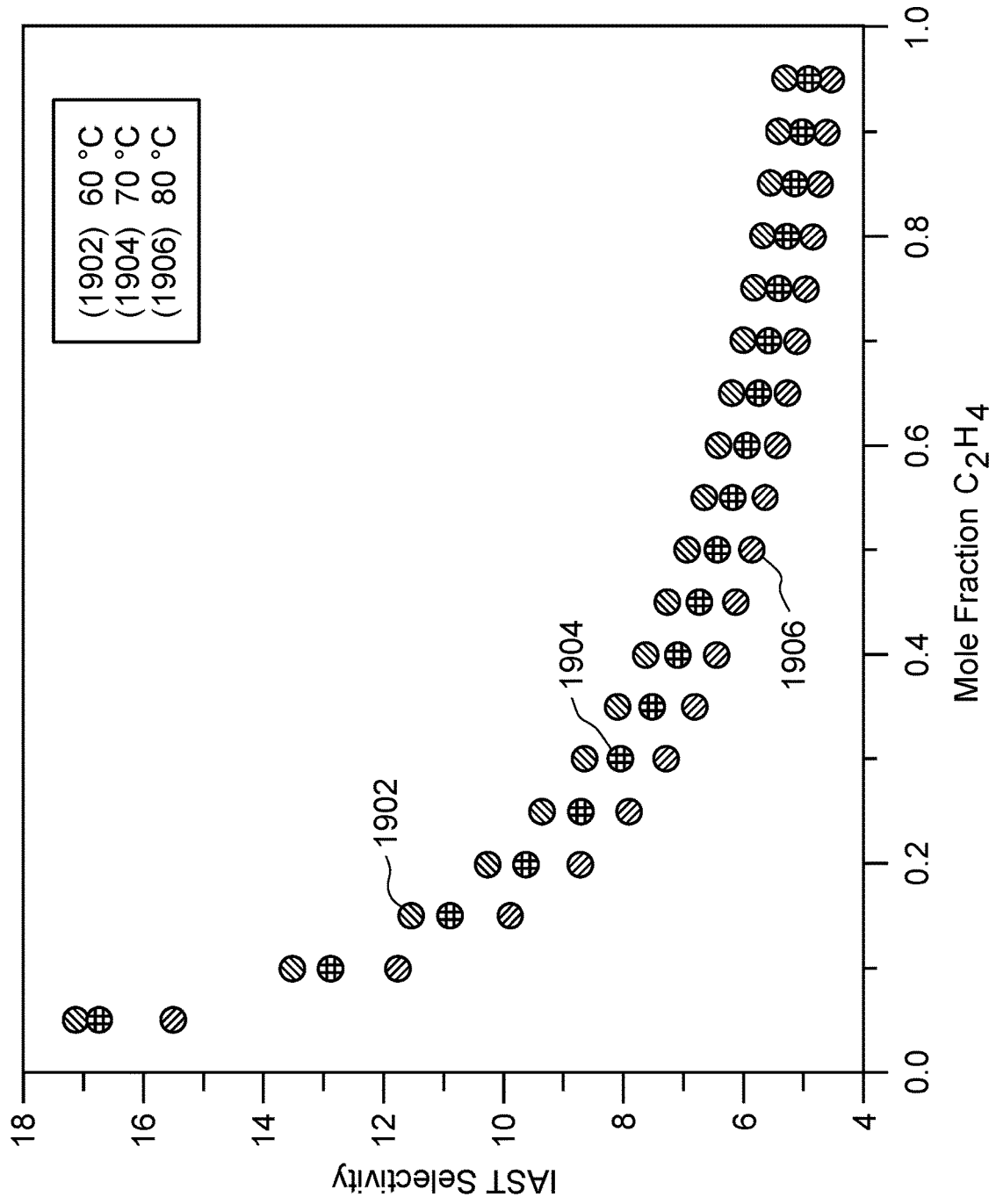

FIG. 19 illustrates IAST selectivity values collected at multiple temperatures for a 50:50 ethylene:ethane mixture at a total pressure of 1 bar, in accordance with an embodiment of the present disclosure.

DETAILED DESCRIPTION

I. Introduction

Designing adsorbents to selectively bind $N_2$ is challenging, as $N_2$ is typically an inert gas that has little interactions with most materials. With the proper design, however, a material can take advantage of specific interactions with $N_2$. In particular, $N_2$ is slightly w acidic, and designing an adsorbent that features a metal center capable of backdonation to the $N_2$ site is expected to create a selective adsorbent, as $CH_4$ lacks this chemical handle.

Metal-organic frameworks (MOFs) are a class of crystalline and porous materials constructed from modifiable metal nodes and organic linkers, and due to their modular nature can in theory be designed to create this type of metal center. See, Furukawa et al., 2013, "The chemistry and applications of metal-organic frameworks," Science 341, 1230444; Li et al., 2009, "Selective gas adsorption and separation in metal-organic frameworks," Chem. Soc. Rev. 38, 1477-1504; Bloch et al., 2011, Hydrocarbon separations in a metal-organic framework with open iron(II) sites," J. Am. Chem Soc. 133, 37, p. 14814; Cadieu et al., 2016, "A metal-organic framework-based splitter for separating propylene from propane," Science 353, 137-140; and Herm et al., 2013, "Separation of hexane isomers in a metal-organic framework with triangular channels," Science 340, 960-962, each of which is hereby incorporated by reference. These frameworks consist of inorganic nodes connected by organic linkers, and the surface functionalities can be precisely tuned to control adsorption properties. A well-established strategy to realize high-performing adsorbents is the attainment of coordinatively unsaturated metal centers. Due to the typical metal ions and weak ligand field linkers used, this approach results in exposed Lewis acidic metal sites that are capable of polarizing and accepting electron density from various adsorbates, enabling effective polarizability-based separations. See Caskey et al., 2008, "Dramatic tuning of carbon dioxide uptake via metal substitution in a coordination polymer with cylindrical pores," J. Am. Chem. Soc. 130, 10870-10871; Bloch et al., 2014, "Reversible CO binding enables tunable $CO/H_2$ and $CO/N_2$ separations in metal-organic frameworks with exposed divalent metal cations," J. Am. Chem. Soc. 136, 10752-10761; and Poloni et al., 2014, "Understanding trends in $CO_2$ adsorption in metal-organic frameworks with open-metal sites," J. Phys. Chem. Lett. 5, 861-865. However, these materials are unable to efficiently separate gases on the basis of backbonding, and separation of mixtures where π-acidity serves as a more suitable handle requires a different approach.

A strategy to realize a selective π-acid adsorbent requires exposed, electron-rich metal centers with the proper electron configuration that can donate electron density into the adsorbate π* orbitals. Specifically, a framework containing square pyramidal vanadium(II) centers is predicted to be an excellent material for backbonding-based separations, as the $d^3$ configuration minimizes electron repulsion while allowing for electron donation onto the adsorbate π* lowest unoccupied molecular orbital. See, Lee et al., 2014, "Design of a metal-organic framework with enhanced back bonding for separation of $N_2$ and $CH_4$," J. Am. Chem. Soc. 136, 698-704, which is hereby incorporated by reference. Furthermore, the electropositive and diffuse vanadium d-orbitals result in an effective energetic and spatial overlap with the adsorbate frontier orbitals, creating a selective and reversible interaction over non T-acids. However, numerous properties of vanadium(II), such as its kinetic inertness, large thermodynamic driving force toward oxidation, and reactivity with carboxylate-containing ligands, have prohibited the crystallization of a vanadium(II) framework. See Jordan, 2007, "Ligand Substitution Reactions" in Reaction Mechanisms of Inorganic and Organometallic Systems, Oxford, N.Y., ed. 3p. 84; Comito et al., 2018, "Stabilized vanadium catalyst for olefin polymerization by site isolation in a metal-organic framework," Angew. Chem., Int. Ed. 57, 8135-8139; and Cotton et al., 1986, "Four compounds containing oxo-centered trivanadium cores surrounded by six $\mu,\eta^2$-carboxylato groups," Inorg. Chem. 25, 3505-3512, each of which is hereby incorporated by reference. While some frameworks contain metal centers that possess the appropriate electronic configuration, failure to combine this with diffuse orbitals or proper energy levels of the relevant molecular orbitals has prevented realization of an effective adsorbent for π-acidic gases. See, Denysenko et al., 2014, "Scorpionate-type coordination in MFU-4l metal-organic frameworks: small-molecule binding and activation upon the thermally activated formation of open metal sites," Angew. Chem., Int. Ed. 53, 5832-5836; and Yoon et al., 2017, "Selective nitrogen capture by porous hybrid materials containing accessible transition metal ion sites," Nat. Mater. 16, 526-531, each of which is hereby incorporated by reference. The need to overcome this synthetic challenge and access a π-acid selective adsorbent is highlighted by one of the most industrially expensive separations: $N_2/CH_4$ for natural gas utilization. See, Caventi et al., 2006, "Separation of $CH_4/CO_2/N_2$ mixtures by layered pressure swing adsorption for upgrade of natural gas," Chem. Eng. Sci. 61, 3893-3906; and Lokhandwala et al., 2010, "Membrane separation of nitrogen from natural gas: A case study form membrane synthesis to commercial deployment," J. Membr. Sci. 346, 270-279, each of which is hereby incorporated by reference. These two gases have similar polarizabilities and kinetic diameters, rendering this separation remarkably difficult. Currently, capital and energy-intensive cryogenic distillation is performed. As the global energy market share of natural gas continues to increase, and as more contaminated alternative sources of methane become more accessible, the development of an energy-efficient separation process is increasingly important. See, Saha et al., 2016, "Postextraction, separation, on-board storage, and catalytic conversion of methane in natural gas: a review," Chem. Rev. 116, 11436-11499, which is hereby incorporated by reference. While a few $N_2$-selective adsorbents exist, these either suffer from low equilibrium selectivity or low $N_2$ capacity. See, Yoon et al., 2017, "Selective nitrogen capture by porous hybrid materials containing accessible transition metal ion sites," Nat. Mater. 16, 526-531; and Kuznicki et al., 2004, "A titanosilicate molecular sieve with adjustable pores for size-selective adsorption of molecules," Nature 412, 720-724, which is hereby incorporated by reference.

The adsorbents of the present disclosure, which have high density of square pyramidal vanadium(II) sites, overcome the above-identified limitations. For instance, they exploit the π-acidity difference between $N_2$ and $CH_4$. Furthermore, this backbonding functionality is leveraged in the present disclosure to separate olefins from paraffins, another energy demanding industrial separation. See, 2016, Sholl, "Seven chemical separations to change the world," Nature 532, 435-438. As such, the disclosed adsorbents expand the molecular properties that can be targeted by solid adsorbents to impart selectivity for gas separations.

In one aspect, the present disclosure provides for the synthesis of a new class of metal-organic frameworks, which includes $V_2Cl_{2.8}$(btdd) ($H_2$btdd=bis(1H-1,2,3-triazolo[4,5-b],[4',5'-i])dibenzo[1,4]dioxin), featuring a high density of square pyramidal vanadium(II) centers. The disclosed adsorbants have unique backbonding capabilities, expanding the functionality available to rigid frameworks for gas separations beyond Lewis acidic behavior. The disclosed adsorbants selectively capture π-acids, such as $N_2$, ethylene, and propylene. This disclosed adsorbants are remarkably suitable for selective $N_2$ adsorption in the presence of $CH_4$. As such, $V_2Cl_{2.8}$(btdd) is a novel metal-organic framework with vanadium(II) sites featuring open coordination sites capable of binding gases. Isostructural to previously reported $M_2Cl_2$ (btdd) materials (M=Mn, Fe, Co, Ni, Cu), (Rieth et al., 2016, "High and reversible ammonia uptake in mesoporous azolate metal-organic frameworks with open Mn, Co, and Ni sites:" J. Am. Chem. Soc. 138, p. 9401; Reed et al., 2017, "A spin transition mechanism for cooperative adsorption in metal-organic frameworks," Nature 550, p. 96; and Park et al., 2017, "Single ion Li+, Na+, and Mg2+ solid electrolytes supported by a mesoporous anionic Cu-azolate MOF," J. Am. Chem. Soc. 139, p. 13260) these materials contain a high density of open vanadium sites as well as good chemical stability. As such, these materials are uniquely suitable for use in $N_2$ separation applications, or in π-acid separations.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In describing the present invention, the following terms will be employed, and are defined as indicated below.

II. Definitions

Where substituent groups are specified by their conventional chemical formulae, written from left to right, the structures optionally also encompass the chemically identical substituents, which would result from writing the structure from right to left, e.g., —CH$_2$O— is intended to also optionally recite —OCH$_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di-, tri- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to optionally include those derivatives of alkyl defined in more detail below, such as "heteroalkyl." Alkyl groups that are limited to hydrocarbon groups are termed "homoalkyl". Exemplary alkyl groups include the monounsaturated C$_{9-10}$, oleoyl chain or the diunsaturated C$_{9-10, 12-13}$ linoeyl chain.

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The terms "aryloxy" and "heteroaryloxy" are used in their conventional sense, and refer to those aryl or heteroaryl groups attached to the remainder of the molecule via an oxygen atom.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —CO$_2$R'— represents both —C(O)OR' and —OC(O)R'.

The terms "cycloalkyl" and "heterocycloalkyl," by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Further exemplary cycloalkyl groups include steroids, e.g., cholesterol and its derivatives. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl substituent groups (or rings) that contain from one to four heteroatoms selected from N, O, S, Si and B, wherein the nitrogen and sulfur atoms are optionally oxidized, and the nitrogen atom(s) are optionally quaternized. An exemplary heteroaryl group is a six-membered azine, e.g., pyridinyl, diazinyl and triazinyl. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl)

includes aryl, heteroaryl and heteroarene rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl, and "heteroaryl") are meant to optionally include both substituted and unsubstituted forms of the indicated species. Exemplary substituents for these species are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: H, substituted or unsubstituted aryl, substituted or unsubstituted heteroaryl, substituted or unsubstituted heterocycloalkyl, —OR', =O, =NR', =N—OR', —NR'R"—SR', halogen, —SiR'R"R'", OC(O)R', —C(O)R', —CO$_2$R', —CONR'R", —OC(O)NR'R", —NR"C(O)R', NR'C(O)NR"R'", —NR"C(O)$_2$R', —NR—C(NR'R"R'")=NR"", —NRC(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). These terms encompass groups considered exemplary "alkyl group substituents," which are components of exemplary "substituted alkyl" and "substituted heteroalkyl" moieties.

Similar to the substituents described for the alkyl radical, substituents for the aryl heteroaryl and heteroarene groups are generically referred to as "aryl group substituents." The substituents are selected from, for example: groups attached to the heteroaryl or heteroarene nucleus through carbon or a heteroatom (e.g., P, N, O, S, Si, or B) including, without limitation, substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$) alkoxy, and fluoro(C$_1$-C$_4$)alkyl, in a number ranging from zero to the total number of open valences on the aromatic ring system. Each of the above-named groups is attached to the heteroarene or heteroaryl nucleus directly or through a heteroatom (e.g., P, N, O, S, Si, or B); and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl, heteroarene or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$-B-, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl, heteroarene or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$) alkyl. These terms encompass groups considered exemplary "aryl group substituents", which are components of exemplary "substituted aryl" "substituted heteroarene" and "substituted heteroaryl" moieties.

As used herein, the term "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non-aromatic rings. Examples of "fused ring systems" are naphthalenes, indoles, quinolines, chromenes and the like.

As used herein, the term "heteroatom" includes oxygen (O), nitrogen (N), sulfur (S) and silicon (Si), boron (B) and phosphorous (P).

The symbol "R" is a general abbreviation that represents a substituent group that is selected from H, substituted or unsubstituted alkyl, substituted or unsubstituted heteroalkyl, substituted or unsubstituted aryl, substituted or unsubstituted heteroaryl, and substituted or unsubstituted heterocycloalkyl groups.

The compounds disclosed herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The term "salt(s)" includes salts of the compounds prepared by the neutralization of acids or bases, depending on the particular ligands or substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium calcium, ammonium, organic amino, or magnesium salt, or a similar salt. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Certain specific compounds of the present invention contain both basic and acidic functionalities that allow the compounds to be converted into either base or acid addition salts. Hydrates of the salts are also included.

The term "—COOH" is meant to optionally include —C(O)O⁻ and —C(O)O⁻X⁺, wherein X⁺ is a cationic counter-ion. Likewise, a substituent having the formula —N(R)(R) is meant to optionally include —N⁺H(R)(R) and —N⁺H(R)(R)Y⁻, where Y⁻ represents an anionic counter-ion. Exemplary polymers of the invention include a protonated carboxylic moiety (COOH). Exemplary polymers of the invention include a deprotonated carboxylic moiety (COO⁻). Various polymers of the invention include both a protonated carboxylic moiety and a deprotonated carboxylic moiety.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. In addition it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

Below are examples of specific embodiments of the present disclosure. The examples are offered for illustrative purposes only, and are not intended to limit the scope of the present invention in any way.

III. Compositions

One aspect of the present disclosure provides an adsorption material comprising a metal-organic framework. The metal-organic framework comprises a plurality of vanadium sites interconnected by a plurality of organic linkers. Each respective organic linker M in the plurality of organic linkers comprises:

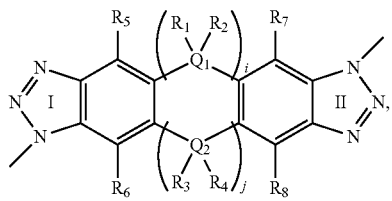

where $Q_1$ and $Q_2$ are each independently carbon, oxygen, or nitrogen while i and j are each independently 0, 1, or 2, with the proviso that at least one $Q_1$ is carbon when i is 2 and at least one $Q_2$ is carbon when j is 2.

Each instance of each $R_1$, $R_2$, $R_3$, $R_4$, and $R_5$, $R_6$, $R_7$, and $R_8$ is independently H, halogen, substituted or unsubstituted alkyl, substituted or unsubstituted heteroalkyl, substituted or unsubstituted aryl, substituted or unsubstituted heteroaryl, substituted or unsubstituted heterocycloalkyl, substituted or unsubstituted alkoxy, substituted or unsubstituted arlyoxy, or substituted or unsubstituted heteroaryloxy, with the provisos that (i) $R_1$ and $R_2$ are not present when a $Q_1$ is oxygen, $R_3$ and $R_4$ are not present when a $Q_2$ is oxygen, one of $R_1$ and $R_2$ is not present when $Q_1$ is nitrogen, and one of $R_3$ and $R_4$ is not present when $Q_2$ is nitrogen.

Figure 1A:
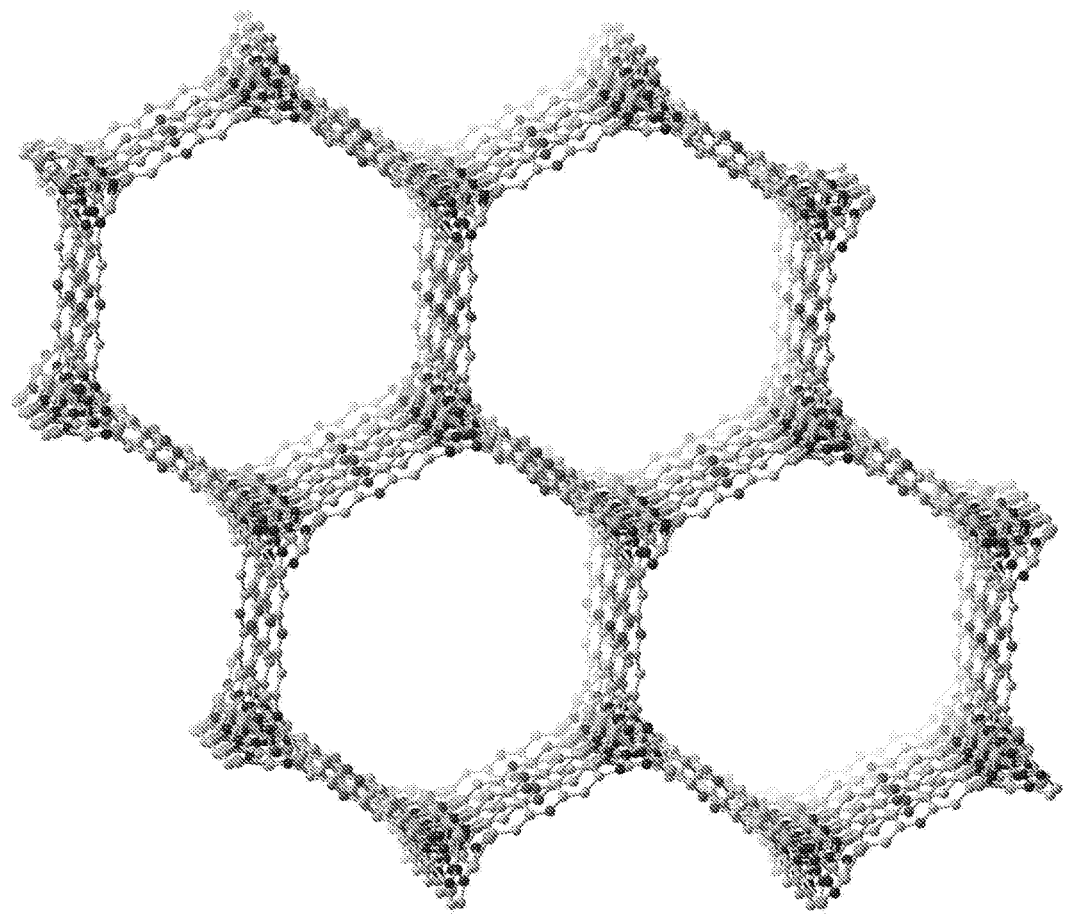
FIG. 1A illustrates a portion of the structure of the metal-organic framework $V_2Cl_{2.8}$(btdd) ($H_2$btdd=bis(1H-1,2,3-triazolo[4,5-b],[4',5'-i])dibenzo[1,4]dioxin), solved through analysis of powder X-ray diffraction data, that is suitable for selective $N_2$ adsorption in the presence of $CH_4$, in accordance with an embodiment of the present disclosure.
Figure 1B:
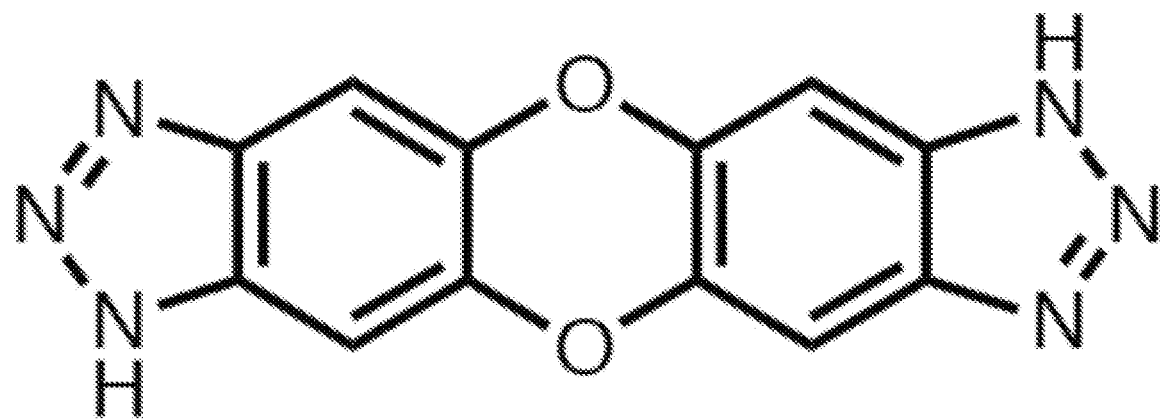
FIG. 1B illustrates the structure of the ligand bis(1H-1,2,3-triazolo[4,5-b],[4',5'-i])dibenzo[1,4]dioxin.
Figure 1C:
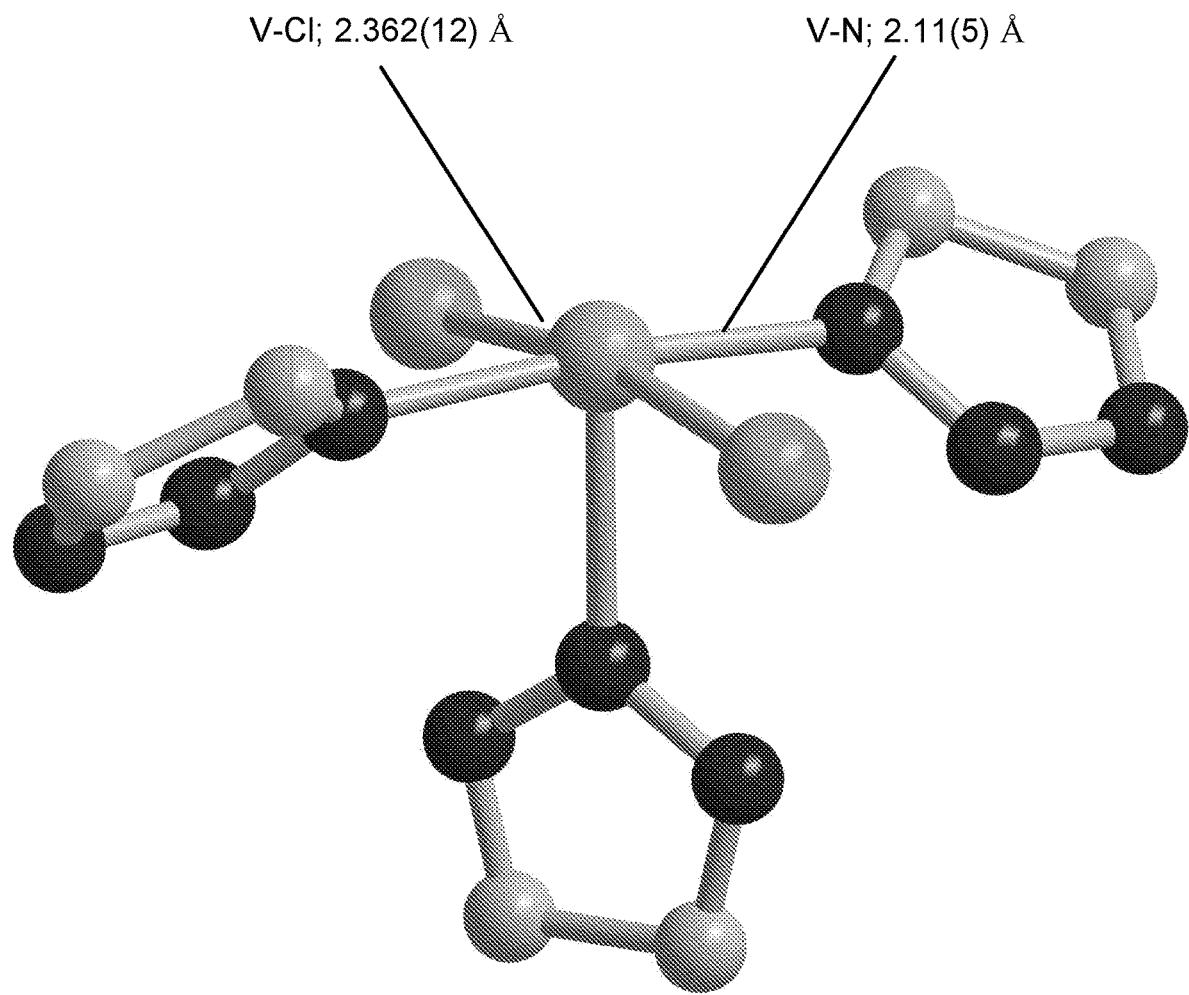
FIG. 1C provides details of a single vanadium(II) center, with an open coordination center available for gas binding, in accordance with an embodiment of the present disclosure.
Figure 1D:
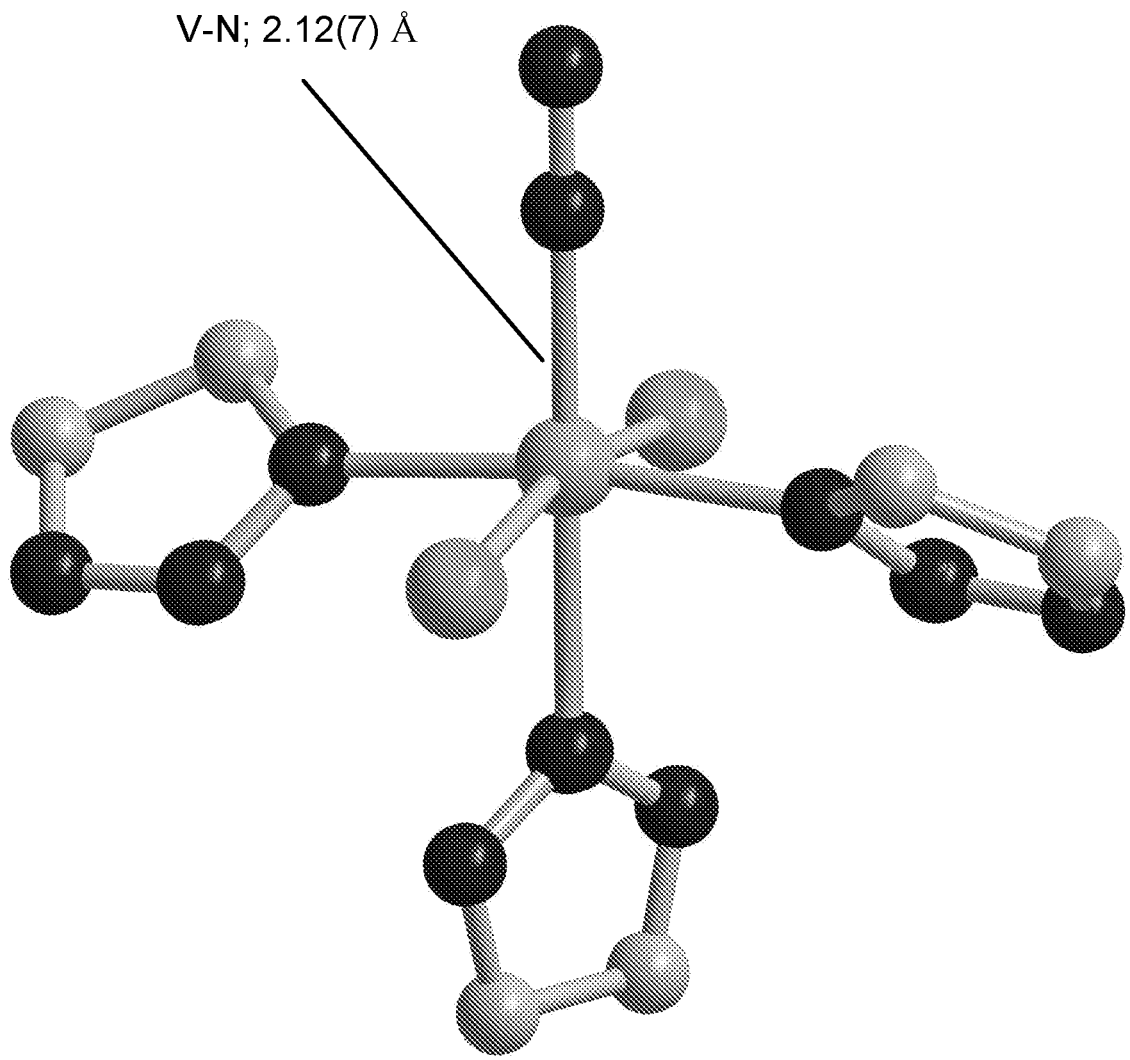
FIG. 1D illustrates the structure of $N_2$-dosed material, $V_2(N_2)_2Cl_2$(btdd), in accordance with an embodiment of the present disclosure.
Figure 1E:
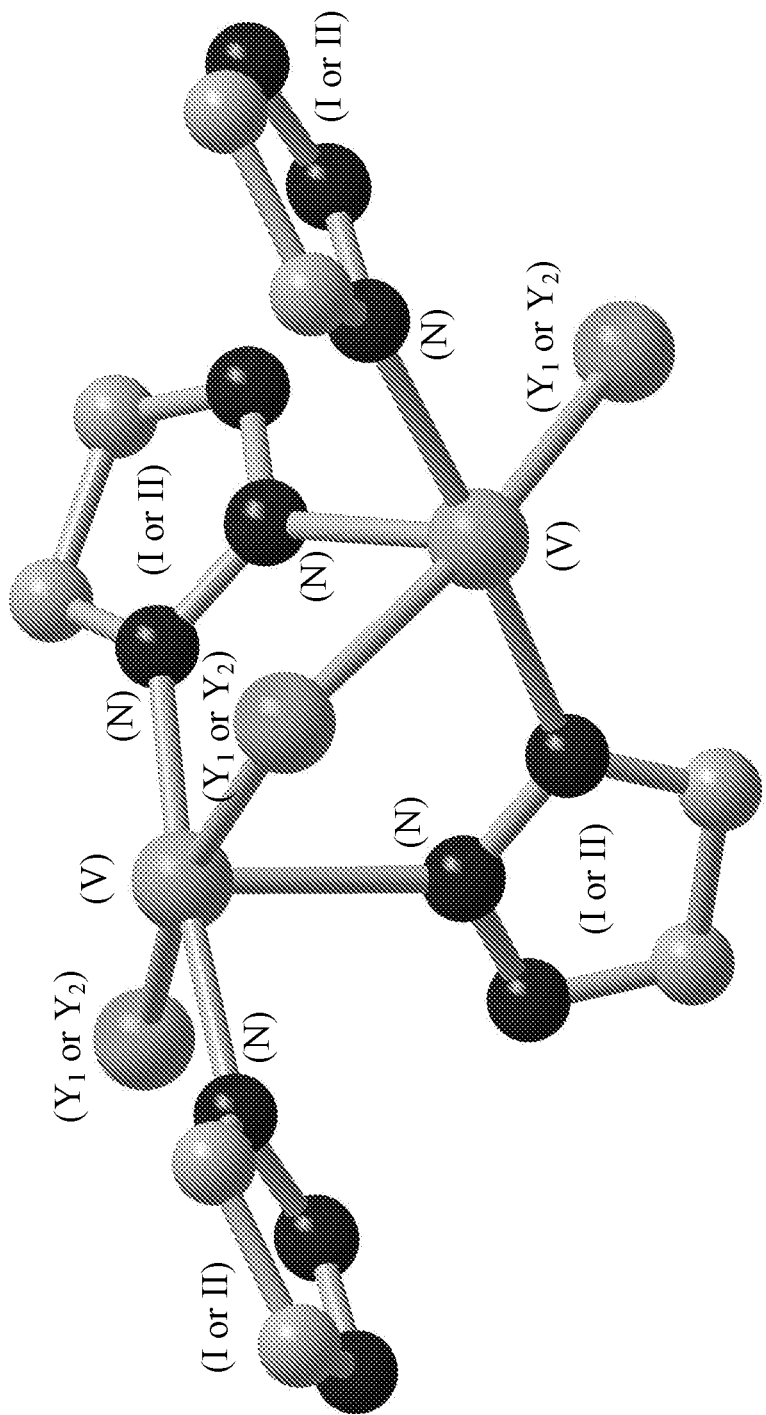
FIG. 1E illustrates the structure of an adsorption material comprising a metal-organic framework comprising a plurality of vanadium sites interconnected by a plurality of organic linkers, where each respective organic linker M in the plurality of organic linkers comprises.

As illustrated in FIGS. 1C and 1E, a vanadium site in the plurality of vanadium sites has a coordination of

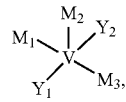

where $M_1$, $M_2$, and $M_3$ are each a respective organic linker M in the plurality of organic linkers that binds to the vanadium site through a free nitrogen in the I or II ring of the respective organic linker M, and $Y_1$ and $Y_2$ are each independently, chlorine, bromine, —SCH₃, —SCN, or —NR'R", where R' and R" are substituted or unsubstituted alkyl, or substituted or unsubstituted heteroalkyl. In some embodiments, $Y_1$ and $Y_2$ are both the same (e.g., both chlorine, both bromine, both —SCH₃, both —SCN, or both —NR'R"). In some $Y_1$ and $Y_2$ are different. While the structure of M includes a designation of the free nitrogen, it will be appreciated that the structure of M includes all tautomeric equivalents and thus the actual free nitrogen that binds the vanadium may different than the one depicted in the structural formula of M. Thus, in some embodiments, advantageously a sixth unoccupied coordination site of the vanadium is free to selectively bond with undesirable $N_2$ present in a natural gas. In alternative embodiments, advantageously, a sixth unoccupied coordination site of the vanadium is free to selectively bond with an undesirable π-acid.

In some embodiments, at least ten percent, twenty percent, thirty percent, forty percent, fifty percent, sixty percent, seventy percent, eighty percent or ninety percent, ninety-eight percent, or ninety-nine percent of the vanadium sites in the plurality of vanadium sites have a coordination of

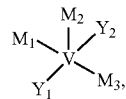

where $M_1$, $M_2$, and $M_3$ are each a respective organic linker M in the plurality of organic linkers that binds to the vanadium site through a free nitrogen in the I or II ring of the respective organic linker M, and $Y_1$ and $Y_2$ are each independently, chlorine, bromine, —SCH₃, —SCN, or —NR'R", where R' and R" are substituted or unsubstituted alkyl, or substituted or unsubstituted heteroalkyl.

In some embodiments, $Q_1$ and $Q_2$ are each oxygen, i is one and j is one so that each respective organic linker M in the plurality of organic linkers comprises:

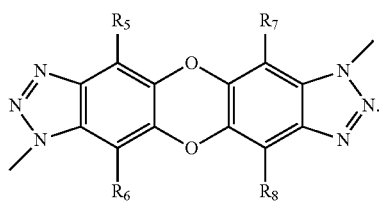

In some embodiments i is zero and j is zero so that each respective organic linker M in the plurality of organic linkers comprises:

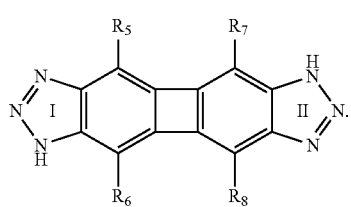

In some embodiments, $Q_1$ and $Q_2$ are each oxygen, i is 1, j is 1, and each instance of each $R_5$, $R_6$, $R_7$, and $R_8$ is independently H, halogen, substituted or unsubstituted n-alkyl or a substituted or unsubstituted branched-chain alkyl.

In some embodiments, $Q_1$ and $Q_2$ are each oxygen, i is 1, j is 1, and each instance of each $R_5$, $R_6$, $R_7$, and $R_8$ is independently H.

In some embodiments $Y_1$ and $Y_2$ are each chlorine. In some embodiments, $Y_1$ and $Y_2$ are each bromine. In some embodiments, $Y_1$ and $Y_2$ are each —$SCH_3$. In some embodiments, $Y_1$ and $Y_2$ are each —SCN. In some embodiments, $Y_1$ and $Y_2$ are each —NR'R", where R' and R" are each independently substituted or unsubstituted alkyl, or substituted or unsubstituted heteroalkyl.

Another aspect of the present disclosure provides an adsorption material comprising a metal-organic framework comprising a plurality of vanadium sites interconnected by a plurality of organic linkers. Each respective organic linker M in the plurality of organic linkers comprises:

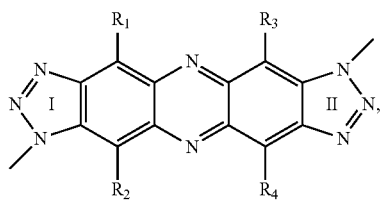

where each instance of each $R_1$, $R_2$, $R_3$, and $R_4$, is independently H, halogen, substituted or unsubstituted alkyl, substituted or unsubstituted heteroalkyl, substituted or unsubstituted aryl, substituted or unsubstituted heteroaryl, substituted or unsubstituted heterocycloalkyl, substituted or unsubstituted alkoxy, substituted or unsubstituted arlyoxy, or substituted or unsubstituted heteroaryloxy. A vanadium site in the plurality of vanadium sites has a coordination of:

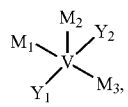

where $M_1$, $M_2$, and $M_3$ are each a respective organic linker M in the plurality of organic linkers that binds to the vanadium site through a free nitrogen in the I or II ring of the respective organic linker M, and $Y_1$ and $Y_2$ are each halogen. In some such embodiments, at least ten percent, twenty percent, thirty percent, forty percent, fifty percent, sixty percent, seventy percent, eighty percent or ninety percent, ninety-eight percent, or ninety-nine percent of the vanadium sites in the plurality of vanadium sites have a coordination of:

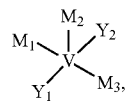

where $M_1$, $M_2$, and $M_3$ are each a respective organic linker M in the plurality of organic linkers that binds to the vanadium site through a free nitrogen in the I or II ring of the respective organic linker M, and $Y_1$ and $Y_2$ are each halogen. In some embodiments $Y_1$ and $Y_2$ are each chlorine.

Another aspect of the present disclosure is an adsorption material comprising a metal-organic framework comprising a plurality of vanadium sites interconnected by a plurality of organic linkers. Each respective organic linker M in the plurality of organic linkers comprises:

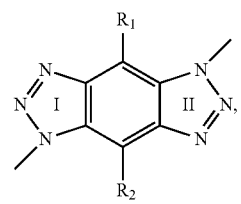

where each instance of each $R_1$, and $R_2$ is independently H, halogen, substituted or unsubstituted alkyl, substituted or unsubstituted heteroalkyl, substituted or unsubstituted aryl, substituted or unsubstituted heteroaryl, substituted or unsubstituted heterocycloalkyl, substituted or unsubstituted alkoxy, substituted or unsubstituted arlyoxy, or substituted or unsubstituted heteroaryloxy. A vanadium site in the plurality of vanadium sites has a coordination of:

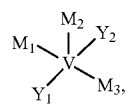

where $M_1$, $M_2$, and $M_3$ are each a respective organic linker M in the plurality of organic linkers that binds to the vanadium site through a free nitrogen in the I or II ring of the respective organic linker M, and $Y_1$ and $Y_2$ are each independently, chlorine, bromine, —$SCH_3$, —SCN, or —NR'R", wherein R' and R" are substituted or unsubstituted alkyl, or substituted or unsubstituted heteroalkyl. In some embodiments at least ten percent, twenty percent, thirty percent, forty percent, fifty percent, sixty percent, seventy percent, eighty percent or ninety percent, ninety-eight percent, or ninety-nine percent of the vanadium sites in the plurality of vanadium sites have a coordination of

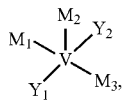

where $M_1$, $M_2$, and $M_3$ are each a respective organic linker M in the plurality of organic linkers that binds to the vanadium site through a free nitrogen in the I or II ring of the respective organic linker M, and $Y_1$ and $Y_2$ are each independently, chlorine, bromine, —SCH$_3$, —SCN, or —NR'R", where R' and R" are substituted or unsubstituted alkyl, or substituted or unsubstituted heteroalkyl. In some embodiments, $Y_1$ and $Y_2$ are each chlorine.

V. Technical Applications

In one aspect of the present disclosure, there is provided a number of technical applications for the disclosed adsorption materials.

One such application is $N_2$ capture from a biogas such as crude biogas, natural gas, or landfill gas. Biogas, for instance the $N_2/CH_4$ mixtures produced by the breakdown of organic matter, is a renewable fuel source with the potential to replace traditional fossil fuel sources. Removal of $N_2$ from crude biogas mixtures is one of the most challenging aspects of upgrading this promising fuel source to pipeline quality methane. Therefore, for example, the use of adsorbents to selectively remove $N_2$ from $N_2/CH_4$ mixtures with a high working capacity and minimal regeneration energy has the potential to greatly reduce the cost of using biogas in place of natural gas for applications in the energy sector. Some embodiments of the present disclosure provide a method that comprises contacting a biogas, natural gas, landfill gas, or non-renewable gas comprising $N_2$ and $CH_4$ with any adsorption material of the present disclosure to reversibly adsorb $N_2$ from the gas thereby generating an adsorption material enriched for $N_2$ and a residual gas that is greater than 80 percent pure methane, 90 percent pure methane, or 98 percent pure methane. In some such embodiments, the method further comprises stripping a major portion (e.g., fifty percent or more, sixty percent or more, seventy percent or more, eighty percent or more, ninety percent or more, or 98 percent or more) of the $N_2$ from the adsorption material enriched for $N_2$ using a temperature swing adsorption method, vacuum swing adsorption method, a pressure swing adsorption method, a concentration swing adsorption method, or a combination thereof.

In some embodiments, the disclosed compositions (adsorption materials) are used to strip a major portion of the $N_2$ (e.g., at least fifty percent, at least sixty percent, at least seventy percent, at least eighty percent, at least ninety percent, or at least 98 percent) from the adsorption material enriched for $N_2$ using a temperature swing adsorption method or a vacuum swing adsorption method. Example temperature swing adsorption methods and vacuum swing adsorption methods are disclosed in International Publication Number WO2013/059527 A1, which is hereby incorporated by reference.

Another aspect of the present disclosure provides methods for removing $N_2$ from a biogas, natural gas, or landfill gas. In such methods, the biogas, natural gas, or landfill gas is contacted with any of the adsorption materials of the present disclosure, or any combination thereof, to reversibly adsorb $N_2$ from the biogas thereby generating an adsorption material enriched for $N_2$ and a residual gas that is greater than 92 percent, 93 percent, 94 percent, 95 percent, 96 percent, 97 percent, or 98 percent pure methane. In some such embodiments, the method further comprises stripping a major portion of the $N_2$ from the adsorption material enriched for $N_2$ using a regeneration method (e.g., a temperature swing adsorption method, vacuum swing adsorption method, a pressure swing adsorption method, a concentration swing adsorption method, or a combination thereof).

Another aspect of the present disclosure provides methods for separating a π-acid (e.g., $N_2$, ethylene, propylene, acetylene, CO or $H_2$) from a gas produced by a source, comprising exposing the π-acid within the gas to any of the adsorption materials of the present disclosure, or any combination thereof, whereby the π-acid is reversibly separated into the adsorption material. In some such embodiments, the π-acid is reversibly separated from the adsorption material by a regeneration process (e.g., a temperature swing adsorption method, vacuum swing adsorption method, a pressure swing adsorption method, a concentration swing adsorption method, or a combination thereof).

Another aspect of the present disclosure provides methods for storage of a π-acid (e.g., $N_2$, ethylene, propylene, acetylene, CO or $H_2$) gas in an adsorption material of the present disclosure. In such methods, a gas comprising the π-acid is contacted with any of the adsorption materials of the present disclosure, or any combination thereof, to reversibly adsorb the π-acid.

Still another aspect of the present disclosure provides methods for separating an olefin (alkene) from a paraffin (alkane) counterpart of the olfefin in a gas. In the methods the olefin within the gas is exposed to any of the adsorption materials of the present disclosure, or any combination thereof, whereby the olefin is reversibly separated into the adsorption material. In some such embodiments, the olefin is reversibly separated from the adsorption material by a regeneration process (e.g., a temperature swing adsorption method, vacuum swing adsorption method, a pressure swing adsorption method, a concentration swing adsorption method, or a combination thereof). In some embodiments, the olefin is ethylene and the paraffin is ethane. In some embodiments, the olefin is propylene and the paraffin is propane.

VI. Synthesis

Another aspect of the present disclosure provides methods for synthesizing an adsorption material in which a vanadium source is reacted with a ligand source in a solvent that includes an acid, at a temperature between 105° C. and 135° C., or between 115° C. and 125° C., to form an intermediate product. In some embodiments this reaction occurs for six days or more (e.g., for seven days), or between six days and eight days. In some embodiments, the vanadium source comprises $VY_2$, $VY_2(tmeda)_2$, $VY_2(pyridine)_4$, or $VY_2(CH_3OH)_4$, or combinations thereof, where each Y is independently a halogen, such as chorine, and where tmeda is N,N,N',N'-tetramethylethylenediamine.

In some embodiments, the ligand source has the structure of any of the ligand sources of the present disclosure. In some embodiments, the ligand source is $H_2$(ligand), where the ligand has the structure M:

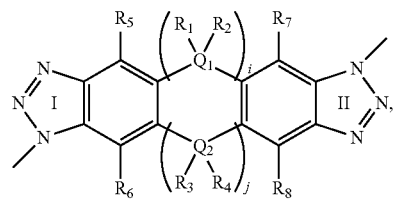

in which $Q_1$ and $Q_2$ are each independently carbon, oxygen, or nitrogen, i and j are each independently 0, 1, or 2, with the proviso that at least one $Q_1$ is carbon when i is 2 and at least one $Q_2$ is carbon when j is 2, and the free nitrogen in the I ring and the II ring each bind a hydrogen prior to the reacting. Each instance of each $R_1$, $R_2$, $R_3$, $R_4$, and $R_5$, $R_6$, $R_7$, and $R_8$ is independently H, halogen, substituted or unsubstituted alkyl, substituted or unsubstituted heteroalkyl, substituted or unsubstituted aryl, substituted or unsubstituted heteroaryl, substituted or unsubstituted heterocycloalkyl, substituted or unsubstituted alkoxy, substituted or unsubstituted arlyoxy, or substituted or unsubstituted heteroaryloxy, with the provisos that: $R_1$ and $R_2$ are not present when a $Q_1$ is oxygen, $R_3$ and $R_4$ are not present when a $Q_2$ is oxygen, one of $R_1$ and $R_2$ is not present when $Q_1$ is nitrogen, and one of $R_3$ and $R_4$ is not present when $Q_2$ is nitrogen. While the structure of M includes a designation of the free nitrogen, it will be appreciated that the structure of M includes all tautomeric equivalents and thus the actual free nitrogen that binds the vanadium may different than the one depicted in the structural formula of M.

The intermediate product is collected and washed with a washing agent such as N,N-dimethylformamide (DMF) and acetonitrile or the like. The collected and washed intermediate product is then activated to thereby form the adsorption material by heating the washed intermediate product to at least 160° C., at 170° C., or between 175° C. and 185° C. under dynamic vacuum (e.g., a pressure of 20 μbar or less, 10 μbar or less, or 5 μbar or less). In some embodiments, this activation by heating the intermediate product under dynamic vacuum occurs for between 40 hours and 70 hours, or between 45 hours and 60 hours. In the present disclosure, activation is the process of removing solvent (e.g. methanol) from the sixth coordination site of each vanadium. This sixth site is then capable of selectively capturing $N_2$ or other π-acids such as ethylene, propylene, acetylene, CO, and $H_2$. The adsorption material includes a vanadium site having a square pyramidal coordination of:

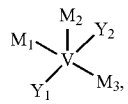

where $M_1$, $M_2$, and $M_3$ are each a respective organic linker M in the plurality of organic linkers that binds to the vanadium site through the free nitrogen in the I or II ring of the respective organic linker M, and $Y_1$ and $Y_2$ are each independently, chlorine, bromine, —$SCH_3$, —SCN, or —NR'R", where R' and R" are substituted or unsubstituted alkyl, or substituted or unsubstituted heteroalkyl. In some such embodiments, $Y_1$ and $Y_2$ are each chlorine, bromine, —$SCH_3$, —SCN, or —NR'R", where R' and R" are substituted or unsubstituted alkyl, or substituted or unsubstituted heteroalkyl. Upon activation, a sixth coordination site of the vanadium become available for selectively capturing $N_2$ or other π-acids such as ethylene, propylene, acetylene, CO, and $H_2$.

In some embodiments $Q_1$ and $Q_2$ are each oxygen, i is one and j is one such that the ligand has the structure:

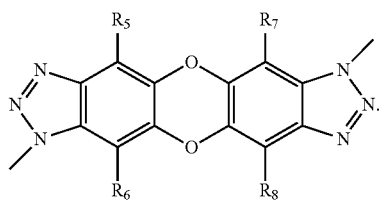

In some alternative embodiments $Q_1$ and $Q_2$ are each oxygen, i is 1, j is 1, and each instance of each $R_5$, $R_6$, $R_7$, and $R_8$ is independently H, halogen, substituted or unsubstituted n-alkyl or a substituted or unsubstituted branched-chain alkyl.

In some alternative embodiments, $Q_1$ and $Q_2$ are each oxygen, i is 1, j is 1, and each instance of each $R_5$, $R_6$, $R_7$, and $R_8$ is independently H.

In some embodiments, Y, $Y_1$ and $Y_2$ are each chlorine. In some embodiments, Y, $Y_1$ and $Y_2$ are each bromine.

In some embodiments, the acid is triflic (trifluoromethanesulfonic) acid, tosylic (p-Toluenesulfonic) acid, mesylic (methanesulfonic) acid, besylic (benzenesulfonic) acid, polystyrene sulfonic acid, ethanesulfonic acid, hydrochloric acid (HCl), hydrobromic acid (HBr), or chromic acid ($H_2CrO_4$), or a combination thereof.

In some embodiments, the solvent comprises N,N-dimethylformamide (DMF), N,N'-dimethylactamide (DMA), N,N'-diethylformamide (DEF), N,N-dimethylmethoxyacetamide, dimethylsulfoxide, hexamethylphosphoramide, N-methyl-2-pyrrolidone, dimethyl sulfone, tetramethylsulfone, or a combination thereof.

An Example of Reaction Using $VCl_2(Tmeda)_2$.

In a specific synthetic example, in which the vanadium source is $VCl_2(tmeda)_2$ and the $H_2$(ligand) source is bis(1H-1,2,3-triazolo[4,5-b],[4',5'-i])dibenzo[1,4]dioxin), two equivalents (180 μmol, 53 mg) $VCl_2(tmeda)_2$, 1 equivalent (20 mg) $H_2$(ligand), 4 equivalents (70 mg) of triflic acid, in 10 ml N,N-dimethylformamide is reacted to form the intermediate product. In some alternative embodiments, 1-4 equivalents $VCl_2(tmeda)_2$, 1 equivalent $H_2$(ligand), and 1-10 equivalents of triflic acid are added to the solvent. In some embodiments the triflic acid is replaced with HCl or tosylic acid, or the like. Furthermore, in some embodiments the N,N-dimethylformamide solvent is replaced with other solvents such as N,N'-dimethylactamide (DMA), or N,N'-diethylformamide (DEF), or the like, or mixtures thereof.

An Example of Reaction Using $VCl_2$.

In another specific synthetic example, in which the vanadium source is $VCl_2$ and the $H_2$(ligand) source is bis(1H-1,2,3-triazolo[4,5-b],[4',5'-i])dibenzo[1,4]dioxin), 2 equivalents (180 μmol, 22 mg) $VCl_2$, 1 equivalent (20 mg) $H_2$(ligand), 0.25 equivalents (4.3 mg) of triflic acid, in 10 ml N,N-dimethylformamide is reacted to form the intermediate product. In some alternative embodiments, 1-4 equivalents $VCl_2(tmeda)_2$, 1 equivalent $H_2$(ligand), and 1-10 equivalents of triflic acid are added to the solvent. In some embodiments, the triflic acid is replaced with HCl or tosylic acid, or the like. Furthermore, in some embodiments the N,N-dimethylformamide solvent is replaced with other solvents such as N,N'-dimethylactamide (DMA), or N,N'-diethylformamide (DEF), or the like, or mixtures thereof.

A similar procedure using the ranges given above is used during the preparation when the vanadium source is $VCl_2$ $(X)_4$.

VI. Examples

The framework $V_2Cl_{2.8}$(btdd) (Figure A) was synthesized using solvothermal conditions by reacting $VCl_2(tmeda)_2$ (tmeda=N,N,N',N'-tetramethylethane-1,2-diamine) and the ligand $H_2$btdd (FIG. 1B) in a mixture of d N,N-dimethylformamide and triflic acid at 120° C. The resulting dark purple microcrystalline product was collected, washed with dimethulformamide and acetonitrile, and activated by heating to 180° C. under dynamic vacuum to afford the final product $V_2Cl_2$(btdd).

The structure of this material was confirmed through powder X-ray diffraction, which shows a material that is isostructural to previously reported $M_2Cl_2(btdd)$ materials. The material has a high Langmuir surface area of 2900 $m^2/g$ showing the porosity and structure is maintained upon activation. Vanadium sites are 5-coordinate and ligated by three triazolate ligands and two chloride ligands, with an open coordination site upon activation that should allow for $N_2$ binding (FIGS. 1C and 1D). This material can be desolvated, affording a Brunauer-Emmett-Teller surface area of 1930 $m^2/g$ (FIG. 4). Rietveld refinement of the powder X-ray diffraction data (FIG. 5) yields a structural model for a framework with one-dimensional hexagonal channels containing 23 Å windows, decorated by vanadium sites at the vertices, confirming the anticipated structure type described by the formula $V_2Cl_{2.8}(btdd)$ (FIG. 1). Due to its highly reducing nature, some of the vanadium sites undergo oxidation during synthesis, resulting in a framework containing approximately 60% coordinatively unsaturated vanadium (II) sites and 40% vanadium(III) sites charge-balanced by apical chlorides (FIG. 6). This is further confirmed by vanadium K-edge X-ray absorption spectroscopy, which exhibits an edge energy consistent with the presence of vanadium(II) and vanadium(III) sites (FIG. 7), and X-ray photoelectron spectroscopy, which is consistent with two types of chlorides (FIG. 8). All vanadium centers are ligated by bridging triazolates and chlorides, with equatorial V—N and V—Cl bond distances of 2.11(5) Å and 2.362(12) Å, respectively, and an axial V—N bond distance of 2.29 Å consistent with mixed vanadium(II) and vanadium(III) character. See Bechlars, 2010, "High-spin ground states via electron delocalization in mixed-valence imidazoalte-bridged divanadium complexes," Nat. Chem. 2, 362-368; and Cotton et al., 1983, "Structural studies of the vanadium (II) and vanadium(III) chloride tetrahydrofuran solvates," J. Chem. Soc., Chem. Commun. 23, 1377-1378.

To further confirm the accessibility and electron-donating ability of the square-pyramidal vanadium(11) centers, we monitored in situ CO dosing by infrared spectroscopy. A single band at 2084 $cm^{-1}$ is observed, suggestive of one type of vanadium binding site (FIG. 9). This is redshifted from free CO, in contrast to the blueshift observed for traditional MOF adsorbents where Lewis acidic behavior dominates. Se, Bloch et al., 2014, "Reversible CO binding enables tunable $CO/H_2$ and $CO/N_2$ separations in metal-organic frameworks with exposed divalent metal cations," J. Am. Chem. Soc. 136, 10752-10761; and Yoon et al., 2017, "Selective nitrogen capture by porous hybrid materials containing accessible transition metal ion sites," Nat. Mater. 16, 526-531. The observed redshift demonstrates that a backbonding interaction is operative. Therefore, this material should perform selective and reversible adsorption of other target π-acidic substrates like $N_2$. Start here The material was investigated for $N_2$ separation properties through isothermal gas adsorption measurements. Adsorption isotherms of $N_2$ collected at 25° C. show a unique $N_2$ adsorption profile, with steep uptake observed at low pressures (FIG. 2). The material adsorbs approximately 3 wt % at just 50 mbar, showing the high degree of interaction of $N_2$ with the vanadium(II) sites. This value then gradually increases to 4.5 wt %. In comparison to other frameworks investigated for $N_2/CH_4$ separations, the uptake at 50 mbar of $N_2$ represents an order of magnitude increase in adsorption capacity, while the overall capacity at these temperatures is higher than that of any previously reported frameworks. Using adsorption isotherms collected at multiple temperatures, the isosteric heat of adsorption is calculated to be −51 kJ/mol. This is a relatively strong interaction that is expected based on the steep isotherm, and is significantly higher in magnitude than previously reported enthalpies in other metal-organic frameworks. See, Yoon et al., "Selective nitrogen capture by porous hybrid materials containing accessible transition metal sites," 2016, Nat. Mater. 16, p. 526, which is hereby incorporated by reference.

Indeed, gas adsorption isotherms reveal $V_2Cl_{2.8}(btdd)$ adsorbs significant amounts of $N_2$ at ambient temperatures. In contrast to typical $N_2$ adsorption isotherms, $V_2Cl_{2.8}(btdd)$ shows an unprecedented steepness at 25° C., rising initially to 1.5 mmol/g at just 50 mbar before gradually rising to 1.9 mmol/g, or >5 wt % (FIG. 10). Analysis of adsorption isotherms collected at multiple temperatures shows an isosteric heat of adsorption of −55.7 kJ/mol, a high value amongst reported metal-organic frameworks and consistent with theoretical data for square pyramidal vanadium(II). See, Lee et al., 2014, "Design of a metal-organic framework with enhanced back bonding for separation of $N_2$ and $CH_4$," J. Am. Chem. Soc. 136, 698-704, which is hereby incorporated by reference.

The $N_2$ adsorption mechanism was probed in a variety of ways. Structural analysis of powder X-ray diffraction (FIG. 5) of the $N_2$-dosed sample $V_2Cl_{2.8}(btdd)$ shows a linear V—$N_2$ interaction with a bond length of 2.12(7) Å (FIG. 7). A structural model can be solved using the powder X-ray diffraction data of the $N_2$-dosed framework $V_2(N_2)_2Cl_2$(btdd) (FIG. 1D). As expected, the $N_2$ binds in an end-on fashion to the exposed vanadium site. The V—N bond distance is 1.93 Å, indicative of a relatively strong M-$N_2$ bond for known adsorbents. The short bond distance suggests that the proposed π backbonding mechanism is observed in this material, and is further supported by infrared spectroscopy. Notably, this bond distance is the shortest M-$N_2$ reported amongst metal-organic frameworks, and represents the first example of a structurally characterized mononuclear vanadium(II)—$N_2$ interaction. See, Lee et al., 2014, "Design of a metal-organic framework with enhanced back bonding for separation of $N_2$ and $CH_4$," J. Am. Chem. Soc. 136, 698-704, which is hereby incorporated by reference.; and Gonzalez et al., 2017, "Structural characterization of framework-gas interactions in the metal-organic framework $Co_2(dobdc)$ by in situ single-crystal X-ray diffraction," Chem. Sci. 8, 4387-4398. Additionally, the $N_2$ adsorption was monitored through in situ infrared spectroscopy (FIG. 11). Dosing $N_2$ in situ at 25° C. shows a distinct growth of one peak at 2291 $cm^{-1}$ (FIG. 3). This value is redshifted with respect to gas-phase $N_2$, which is consistent with theoretical work for a weak field vanadium(II)—$N_2$ interaction, free of solvent and cation effects. See, Lee et al., 2014, "Design of a metal-organic framework with enhanced back bonding for separation of $N_2$ and $CH_4$," J. Am. Chem. Soc. 136, 698-704. The red-shifted $N_2$ stretch is indicative of a strong V—$N_2$ interaction, and provides direct evidence of π back-donation from the vanadium center to the $N_2$ molecule that establishes this favorable V—$N_2$ bond. Further, solid-state magic-angle spinning (MAS) $^{15}N$ NMR spectroscopy was collected for a sample dosed with $^{15}N_2$ (FIG. 12). In contrast to typical diamagnetic adsorbents, Fonseca et al., 1999, "$^{15}$N-NMR characterization and quantitative NMR determination of nitrogen adsorbed in MX zeolites, Porous Materials in Environmentally Friendly Processes," in Surface Science and Catalysis 125, 229, the signal at 267 ppm is significantly broadened and shifted by −40 ppm from free gas-phase $N_2$, consistent with a paramagnetic shift and suggesting the transfer of unpaired electron spin density from vanadium centers. Taken together, the spectroscopic data confirm that the nitrogen is bound directly to the vanadium centers through the proposed backbonding mechanism.

Due to this mechanism for $N_2$ adsorption, the exposed vanadium sites allow for excellent performance in the adsorption of $N_2$ for industrial applications. For separations involving $N_2$, natural gas processing is the largest industrial process, with all inert gases required to be below a total of 4% and $N_2$ levels typically required to be lower than 2%. See, Caventi et al., 2006, "Separation of $CH_4/CO_2/N_2$ mixtures by layered pressure swing adsorption for upgrade of natural gas," Chem. Eng. Sci. 61, 3893-3906; Lokhandwala et al., 2010, "Membrane separation of nitrogen from natural gas: A case study form membrane synthesis to commercial deployment," J. Membr. Sci. 346, 270-279; and Rufford et al., 2012, "The removal of $CO_2$ and $N_2$ from natural gas: A review of conventional and emerging process technologies," J. Pet. Sci. Eng. 94, 123-154. Therefore, both capacity and selectivity over $CH_4$ should be maximized at these low pressures. Comparing $V_2Cl_{2.8}$(btdd) to previously reported materials for $N_2$ capture, Yoon et al., 2017, "Selective nitrogen capture by porous hybrid materials containing accessible transition metal ion sites," Nat. Mater. 16, 526-531; and Kuznicki et al., 2004, "A titanosilicate molecular sieve with adjustable pores for size-selective adsorption of molecules," Nature 412, 720-724, this new mechanism allows for the highest uptake at all pressures. Adsorption isotherms of $N_2$ collected at 25° C. show a very large uptake at low pressures, with 1.09 mmol/g adsorbed at 20 mbar and 1.32 mmol/g adsorbed at 40 mbar. This is substantially higher than all reported materials, as previously high-performing materials only adsorb ~0.25 mmol/g at 20 mbar at a much lower temperature of 10° C. See, Yoon et al., 2017, "Selective nitrogen capture by porous hybrid materials containing accessible transition metal ion sites," Nat. Mater. 16, 526-531. Even more impressive, at 40 mbar the $N_2$ uptake in $V_2Cl_{2.8}$(btdd) is higher than that of all other materials by 1 bar at the same temperature, highlighting its impressive performance for this separation.

In assessing the selectivity for $N_2$ adsorption, a comparison to the $CH_4$ adsorption isotherm collected at 25° C. shows that $V_2Cl_{2.8}$(btdd) adsorbs substantially more $N_2$ than $CH_4$ at all pressures (FIG. 2). While $V_2Cl_{2.8}$(btdd) adsorbs $CH_4$ with a considerable binding enthalpy of −35 kJ/mol, similar to that predicted in theoretical vanadium(II) frameworks, Lee et al., 2014, "Design of a metal-organic framework with enhanced back bonding for separation of $N_2$ and $CH_4$," J. Am. Chem. Soc. 136, 698-704, its adsorption profile relative to that of $N_2$ indicates a considerable selectivity for $N_2$ adsorption. Using Ideal Adsorbed Solution Theory (IAST), selectivity values at low $N_2$ concentrations and 1 bar total pressure are exceptional (FIG. 13). Comparing to other materials, whose values are reported at a ratio of 20:80 $N_2:CH_4$, $V_2Cl_{2.8}$(btdd) shows a selectivity of 38. This is substantially higher than the previous best-performing material, a chromium(III)-based metal-organic framework which exhibits a selectivity of ~8 at a lower temperature of 10° C., and decreases even further upon warming. See, Yoon et al., 2017, "Selective nitrogen capture by porous hybrid materials containing accessible transition metal ion sites," Nat. Mater. 16, 526-531. Furthermore, because of the steepness of the $N_2$ adsorption isotherm, the IAST selectivity shows a considerable rise at lower concentrations of $N_2$. In particular, it reaches selectivity values of 63 and 72 at 4% and 2% $N_2$ in $CH_4$, respectively, indicative of highly selective adsorption with prospect of use in real process separations.

Importantly, $N_2$ adsorption isotherms at higher temperatures for $V_2Cl_{2.8}$(btdd) retain steep initial $N_2$ uptakes. Performing similar analyses at temperatures as high as 45° C., the IAST selectivity values are similar to the values at 25° C. Due to the strong orbital-mediated V—$N_2$ interaction relative to that with $CH_4$, the backbonding mechanism allows for this selectivity to remain temperature invariant within this range (FIG. 13). This is similar to other materials that perform separations through more specific orbital interactions to form strong, chemisorptive interactions with target substrates, and in some cases these materials show greater selectivities at higher temperatures. See, Reed et al., 2016, "Reversible CO scavenging via adsorbate-dependent spin state transitions in an iron(II)-triazolate metal-organic framework," J. Am. Chem. Soc. 138, 5594-5602. In contrast, polarizability-driven mechanisms show negative dramatic temperature effects, where raising the temperature from 10 to 20° C. lowers the IAST selectivity under standard conditions by over 20%. See, Yoon et al., 2017, "Selective nitrogen capture by porous hybrid materials containing accessible transition metal ion sites," Nat. Mater. 16, 526-531.

The disclosed findings indicate the potential for $V_2Cl_{2.8}$(btdd) to be exceptional for $N_2$ separation from $CH_4$. This material contains the first vanadium(II) open metal site in an extended material, a synthetically challenging problem. Due to the favorable interaction of the vanadium site with $N_2$, very high adsorption capacities and high selectivities for $N_2$ are observed. These are significantly higher than any current adsorbent-based technology, and as such this material represents a significant step forward in creating suitable adsorbents for industrial $N_2/CH_4$ separations.

Separations Involving Other π-Acidic Gases.

The impressive selectivity and its temperature dependence of the disclosed compounds was applied to other separations involving π-acidic gases. Olefin separations from mixtures in paraffins is required on enormous scales that currently utilize 0.3% of the world's energy use. See, Sholl and Lively, 2016, "Seven chemical separations to change the world," Nature 532, 435-438. Similar to $N_2$ removal from natural gas, this separation currently exploits small volatility differences, resulting in an expensive and energy-demanding process. Metal-organic frameworks containing open metal sites have been investigated as possible adsorption-based alternatives. See, Bloch et al., 2012, "Hydrocarbon separations in a metal-organic framework with open iron(II) sites," Science 335, 1606-1610; Bachman et al., 2017, "$M_2$(m-dobdc) (M=Mn, Fe, Co, Ni) metal-organic frameworks as highly selective, high-capacity adsorbents for olefin/paraffin separations," J. Am. Chem. Soc. 139, 15363-15370; and Li et al., 2014, "Introduction of pi-complexation into porous aromatic framework for highly selective adsorption of ethylene over ethane," J. Am. Chem. Soc. 136, 8654-8660. However, while these materials are able to effectively perform these separations at room temperature, increasing the separation temperature to align with olefin-paraffin production processes, Eldridge, 1993, "Olefin/Paraffin separation technology: a review," Ind. Eng. Chem. Res. 32, 2208-2212; and Ren et al, 2006 "Olefins from conventional and heavy feedstocks: energy use in steam cracking and alternative processes," Energy 31, 425-451, results in significant decreases in selectivity.

The present disclosure leverages the backbonding capabilities of vanadium(II) towards selective capture of ethylene and propylene at elevated temperatures. For instance, the ability of the vanadium centers to form a backbonding interaction with the olefin π* orbital was assessed through infrared spectroscopy. An infrared spectrum for propylene-dosed $V_2Cl_{2.8}$(btdd) collected at room temperature shows a redshifted C=C stretch at 1620 cm$^{-1}$, the first example of a redshifted propylene stretch collected in a metal-organic framework (FIG. 14). Ethylene and propylene adsorption isotherms collected at a variety of temperatures show strong binding enthalpies of −68 and −67 kJ/mol, respectively (FIGS. 15 and 16. Fitting parameters for FIG. 15 are set forth in Table 1.

TABLE 1

Fitting parameters to the dual-site Langmuir-Freundlich equation for ethylene adsorption at 60-80° C.

| Parameter | Value |
| --- | --- |
| $n_{sat,\ 1}$ (mmol/g) | 1.26 |
| $E_1$ (−kJ/mol) | 58.0 |
| $S_1$ (−R) | 16.4 |
| $v_1$ | 0.839 |
| $n_{sat,\ 2}$ (mmol/g) | 4.72 |
| $E_2$ (−kJ/mol) | 32.5 |
| $S_2$ (−R) | 12.3 |
| $v_2$ | 1.06 |

Fitting parameters for FIG. 16 are set forth in Table 2.

TABLE 2

Fitting parameters to the dual-site Langmuir-Freundlich equation for propylene adsorption at 60-80° C.

| Parameter | Value |
| --- | --- |
| $n_{sat,\ 1}$ (mmol/g) | 1.04 |
| $E_1$ (−kJ/mol) | 51.12 |
| $S_1$ (−R) | 13.15 |
| $v_1$ | 0.75 |
| $n_{sat,\ 2}$ (mmol/g) | 9.69 |
| $E_2$ (−kJ/mol) | 27.20 |
| $S_2$ (−R) | 10.11 |
| $v_2$ | 0.98 |

Notably, these values correlate with backbonding interactions, in contrast to traditional Lewis acidic adsorbents which trend with polarizability and bind propylene substantially more strongly than ethylene. See, Bloch et al., 2012, "Hydrocarbon separations in a metal-organic framework with open iron(II) sites," Science 335, 1606-1610; and Bachman et al., 2017, "M$_2$(m-dobdc) (M=Mn, Fe, Co, Ni) metal-organic frameworks as highly selective, high-capacity adsorbents for olefin/paraffin separations," J. Am. Chem. Soc. 139, 15363-15370.

Due to this mechanism, the disclosed framework binds these olefins with high affinity at high temperatures. Indeed, the ethylene adsorption isotherm collected at 80° C. shows a steep and substantial uptake, while notably remaining highly reversible (FIGS. 17 and 18). Ethane adsorption isotherms, in contrast, are more shallow at all temperatures measured. IAST selectivity values for a 50:50 ethylene:ethane mixture at various temperatures were examined, and as predicted the selectivity rises as a function of temperature, reaching 6.9 at 80° C. (FIG. 19), representing the first example of increasing selectivity with increasing temperature for this industrially relevant mixture. Importantly, $V_2Cl_{2.8}$(btdd) also retains high capacities at these temperatures. As the temperature dependence of this selectivity could allow for much more energetically favorable separation conditions, this backbonding mechanism is thus applicable to realistic separation conditions for a variety of industrial processes. In addition, the impressive performance for selectivity at low concentrations of ethylene at these elevated temperatures, where this material shows record selectivity values, suggests that this material should be quite effective for ethylene selectivity in ethane-rich feeds.

The present disclosure provides the synthesis of a material with a high-density of reducing and coordinatively unsaturated metal sites capable of strong yet reversible orbital-mediated interactions with adsorbates. This property enables unprecedented performance for separations of π-acidic gases, and serves as a design principle for next generation adsorbents capable of exploiting differences in the frontier orbitals of adsorbates to impart selectivity. Additionally, this type of small molecule binding provides further insight for a wide variety of adsorbent-based applications, including activation, sensing, and catalysis.

Exchanging Bridging —Cl for Bridging —SCH$_3$.

Under an inert (N$_2$) atmosphere, excess trimethyl(methylthio)silane is added to a stirring tetrahydrofuran (THF) solution containing V$_2$Cl$_2$(btdd). The reaction solution is left to stir at 30° C. for 24 hours under an inert (N$_2$) atmosphere. The reaction is filtered and washed with THF under an inert (N$_2$) atmosphere. From powder X-ray diffraction, it was determined that the material remains crystalline and that relative intensities of low angle reflections change substantially. Judging from CHNS elemental analysis, SCH$_3$ incorporation following this procedure has been observed for M$_2$Cl$_2$(btdd) frameworks (M=Cr, Fe, and Ni). It is expected that similar analysis on V-MOF will show the same incorporation of SCH$_3$. For V, higher temperatures and longer reaction conditions may be able to realize full conversion (full substitution of the the Cl by SCH$_3$) in the V-MOF, to yield V$_2$(SCH$_3$)$_2$(btdd).

General Considerations.

All synthetic procedures were performed under an argon atmosphere using standard Schlenk techniques or in an N$_2$-filled VAC Atmospheres glove box. Methanol was purchased from EMD Millipore Corporation as DriSolv grade, dried over 3 Å molecular sieves, and sparged with argon before use. N,N-dimethylformamide (DMF) was purchased from EMD Millipore Corporation as OmniSolv grade, sparged with argon, and dried with an alumina column before use. The materials VCl$_2$(tmeda)$_2$, H$_2$(btdd), and VCl$_3$(THF)$_3$ were prepared according to previously reported procedures. See, Edema et al., 1990, "Novel vanadium (II) amine complexes: a facile entry in the chemistry of divalent vanadium, Synthesis and characterization of mononuclear L$_4$VCl$_2$ [L=amine, pyridine]: X-ray structures of trans-(TMEDA)$_2$VCl$_2$ [TMEDA=N, N, N, N-tetramethylethylenediamine] and trans-Mz2V(py)$_2$ [Mz=o-C$_6$H$_4$CH$_2$N(CH$_3$)$_2$, py=pyridine]," Inorg. Chem. 29, 1302-1306; Denysenko et al., 2011, "Elucidating gating effects for hydrogen sorption in MFU-4-type triazolate-based metal-organic frameworks featuring different pore sizes," Chem. Eur. J. 17, 1837-1848; and Manzer et al., 1982, "Tetrahydrofuran complexes of selected early transition metals," Inorg. Synth., 21, 135-140. Dimethylformamidium trifluoromethanesulfonate was purchased from Sigma-Aldrich and dried under vacuum prior to use.

Synthesis of V$_2$Cl$_{2.8}$(btdd)

A solution of VCl$_2$(tmeda)$_2$ (90 mg, 0.254 mmol) and dimethylformamidium trifluoromethanesulfonate (266 mg, 1.20 mmol) in DMF (10 mL) was added to a 20 mL borosilicate vial containing H$_2$(btdd) (20.0 mg, 0.0752 mmol). The solution was heated at 120° C. for 10 days. The resulting dark purple powder was collected by filtration, and soaked in 10 mL of DMF at 120° C. for 24 hour. The solid was then collected by filtration, and soaked in another 10 mL of DMF (washing agent) at 120° C. for 24 hours. This process was repeated five times so that the total time washing with DMF was nine days. The solid was then collected by filtration, and soaked in 10 mL of methanol (washing agent) at 60° C. for 12 hours. The solid was collected by filtration, and soaked in another 10 mL of methanol at 60° C. for 12 hours. This process was repeated five times so that the total time washing with methanol was three days. The resulting solid was collected by filtration, and heated at a rate of 0.2° C./min and held at 180° C. under dynamic vacuum for 36 hours, affording 20 mg of product as a dark purple powder. Elemental analysis of $[V_2Cl_{2.8}(btdd)](MeOH)_2$. found: C, 32.76; H, 2.44; N, 15.88. calculated: C, 31.76; H, 2.28; N, 15.87.

Gas Adsorption Measurements.

Gas adsorption isotherms for pressures in the range 0-1 bar were measured by a volumetric method using a Micromeritics ASAP2020 or Micromeretics 3Flex gas sorption analyzer. A typical sample of approximately 50 mg was transferred in an $N_2$ filled glovebox to a pre-weighed analysis tube, which was capped with a Micromeretics TranSeal and evacuated by heating at 180° C. with a ramp rate of 0.2° C./min under dynamic vacuum until an outgas rate of less than 3 μbar/min was achieved. The evacuated analysis tube containing the degassed sample was then carefully transferred to an electronic balance and weighed again to determine the mass of sample. The tube was then transferred back to the analysis port of the gas adsorption instrument. The outgas rate was again confirmed to be less than 3 μbar/min. For all isotherms, warm and cold free space correction measurements were performed using ultra-high purity He gas (UHP grade 5.0, 99.999% purity); $N_2$, $CH_4$, $C_2H_4$, $C_2H_6$, and $C_3H_6$ isotherms at 298 to 358 K were measured in water baths equipped with a Julabo F32 circulator using UHP-grade gas sources. $N_2$ isotherms collected at 77 K were measured in liquid nitrogen baths. Oil-free vacuum pumps and oil-free pressure regulators were used for all measurements to prevent contamination of the samples during the evacuation process or of the feed gases during the isotherm measurements. Langmuir surface areas were determined from $N_2$ adsorption data at 77 K using Micromeritics software.

Adsorption Isotherm Fitting.

Adsorption isotherms were fit with a dual-site Langmuir-Freundlich equation (eq. 1), where n is the total amount adsorbed in mmol/g, P is the pressure in bar, $n_{sat,i}$ is the saturation capacity in mmol/g, $b_i$ is the Langmuir parameter in $bar^{-1}$ defined in eq. 2, and v is the Freundlich parameter for two sites 1 and 2.

$$n = \frac{n_{sat,1} b_1 P^{v_1}}{1 + b_1 P^{v_1}} + \frac{n_{sat,2} b_2 P^{v_2}}{1 + b_2 P^{v_2}} \quad (1)$$

$$b = e^{-S_1} e^{\frac{H_1}{RT}} \quad (2)$$

For eq. 2, S is the entropy of adsorption at saturation in units of R, H is the enthalpy of adsorption in kJ/mol, for site 1. The fitted parameters for all gases for can be found in Tables 3-7.

TABLE 3

Fitting parameters to the dual-site Langmuir-Freundlich equation for $CH_4$ adsorption at 25-45° C.

| Parameter | Value |
| --- | --- |
| $n_{sat,1}$ (mmol/g) | 3.64 |
| $E_1$ (−kJ/mol) | 34.2 |
| $S_1$ (−R) | 14.8 |
| $v_1$ | 0.967 |
| $n_{sat,2}$ (mmol/g) | 0.401 |
| $E_2$ (−kJ/mol) | 38.7 |
| $S_2$ (−R) | 40.1 |
| $v_2$ | 1 |

TABLE 4

Fitting parameters to the dual-site Langmuir-Freundlich equation for ethylene adsorption at 60-80° C.

| Parameter | Value |
| --- | --- |
| $n_{sat,1}$ (mmol/g) | 1.26 |
| $E_1$ (−kJ/mol) | 58.0 |
| $S_1$ (−R) | 16.4 |
| $v_1$ | 0.839 |
| $n_{sat,2}$ (mmol/g) | 4.72 |
| $E_2$ (−kJ/mol) | 32.5 |
| $S_2$ (−R) | 12.3 |
| $v_2$ | 1.06 |

TABLE 5

Fitting parameters to the dual-site Langmuir-Freundlich equation for propylene adsorption at 60-80° C.

| Parameter | Value |
| --- | --- |
| $n_{sat,1}$ (mmol/g) | 1.04 |
| $E_1$ (−kJ/mol) | 51.12 |
| $S_1$ (−R) | 13.15 |
| $v_1$ | 0.75 |
| $n_{sat,2}$ (mmol/g) | 9.69 |
| $E_2$ (−kJ/mol) | 27.20 |
| $S_2$ (−R) | 10.11 |
| $v_2$ | 0.98 |

TABLE 6

Fitting parameters to the dual-site Langmuir-Freundlich equation for ethane adsorption at 60-80° C.

| Parameter | Value |
| --- | --- |
| $n_{sat,1}$ (mmol/g) | 2.89 |
| $E_1$ (−kJ/mol) | 29.2 |
| $S_1$ (−R) | 12.5 |
| $v_1$ | 1.00 |
| $n_{sat,2}$ (mmol/g) | 8.10 |
| $E_2$ (−kJ/mol) | 32.3 |
| $S_2$ (−R) | 12.7 |
| $v_2$ | 1.01 |

TABLE 7

Vanadium K-edge X-ray absorption edge energies for $V_2Cl_{2.8}$(btdd), $VCl_2$(tmeda)$_2$, and $VCl_3$(THF)$_3$, collected in this study, as well as reference values for VO (47), $VCl_2$ (13), $V_{0.44}Zn_{4.56}Cl_4$(BTDD)$_3$ (13),$VCl_3$(13), and $V_2O_3$ (47). The edge energies were identified by utilizing the first-derivative of the rising edge absorption data. As $V_2Cl_{2.8}$(btdd) shows substantial features in its rising edge, its edge energy was additionally identified by considering half-max of the rising edge, the second value provided.

|  | Compound | Edge energy (kEv) |
|---|---|---|
| V(II) | $V_2Cl_2$(tmeda) | 5.4725 |
|  | $VCl_2$ | 5.4725 |
|  | VO | 5.4730 |
|  | $V_{0.44}Zn_{4.56}Cl_4$(BTDD)$_3$ | 5.4730 |
| — | $V_2Cl_{2.8}$(btdd) | 5.4732, 5.4739 |
|  | $VCl_3$ | 5.4748 |
| V(III) | $VCl_3$(THF)$_3$ | 5.4749 |
|  | $V_2O_3$ | 5.4757 |

Isosteric Heat of Adsorption Calculations.

Using the dual-site Langmuir-Freundlich fits, the isosteric heat of adsorption, $-Q_{st}$, was calculated for each compound as a function of the amount of gas adsorbed using the Clausius-Clapeyron relation (eq. 3), where R is the ideal gas constant, P is the pressure, and T is the temperature.

$$-Q_{st} = RT^2 \left(\frac{\partial \ln P}{\partial T}\right)_n \quad (3)$$

For multi-site Langmuir-Freundlich models, the loading dependence of the isosteric heat of adsorption was calculated. As written, multi-site Langmuir-Freundlich equations specify the amount adsorbed as a function of pressure, while the pressure as a function of the amount adsorbed is needed to use the Clausius-Clapeyron relation. To calculate the isosteric heat of adsorption for evenly spaced loadings, each multi-site Langmuir equation was solved for the pressures that correspond to specific loadings of a given gas at 25-45° C. for $N_2$ and $CH_4$, and 60-80° C. for $C_2H_4$, $C_2H_6$, and $C_3H_8$ and these calculated pressures were then used in eq. 3 to determine the heat of adsorption as a function of the total amount of gas adsorbed.

Ideal Adsorbed Solution Theory Calculations.

Since binary gas adsorption isotherms cannot be measured in a straightforward manner, it is often necessary to use an adsorption model, such as ideal adsorbed solution theory (IAST), to predict mixed gas behavior from experimentally measured single-component isotherms. See, Myers and Prausnitz, 1965, "Thermodynamics of mixed gas adsorption," AIChE J. 11, 121-127. The accuracy of the IAST procedure has already been established for adsorption of a wide variety of different gases in zeolites and metal-organic frameworks. See, Krishna and van Baten, 2011, "In silico screening of metal-organic frameworks in separation applications," Phys. Chem. Chem. Phys. 13, 10593-10616. Here, IAST is used to estimate the selectivity of $V_2Cl_{2.8}$ (btdd) for mixtures of $N_2$ and $CH_4$ at 25-45° C., and $C_2H_4$ and $C_2H_6$ at 60-80° C., with a total pressure of 1 bar for all calculations. The selectivity factor, S, is defined according to equation 4, where n, is the amount adsorbed of each component as determined from IAST and $x_i$ is the mole fraction of each component in the gas phase at equilibrium.

$$S = \frac{n_{N_2}/n_{CH_4}}{x_{N_2}/x_{CH_4}} \quad (4)$$

Powder X-Ray Diffraction.

Microcrystalline powder samples of $V_2Cl_{2.8}$(btdd) (~5 mg) were loaded into two 1.0 mm boron-rich glass capillaries inside a glovebox under an $N_2$ atmosphere. The capillaries were attached to a gas cell, which was connected to the analysis port of a Micromeritics ASAP 2020 gas adsorption instrument. Both capillaries were fully evacuated at 180° C. for 12 hours, one was then flame-sealed while the other capillary was dosed with $N_2$ to a pressure of 700 mbar, equilibrated for 2 hours, and then flame-sealed. Each capillary was placed inside a Kapton tube that was sealed on both ends with epoxy.

High-resolution synchrotron X-ray powder diffraction data were collected at beamline 17-BM at the Advanced Photon Source at Argonne National Laboratory. The temperature of measurement of the capillary samples were kept at 298 K using an Oxford Cryosystems Cryostream 800. Scattered intensity was measured by a PerkinElmer a-Si flat panel detector. The average wavelength of all measurements was 0.45236 Å.

Structure Solution and Rietveld Refinements.

Precise unit cell parameters of evacuated $V_2Cl_{2.8}$(btdd) and $N_2$-dosed $V_2Cl_{2.8}$(btdd) were obtained by Pawley refinement as implemented in TOPAS-Academic 4.1, and were found to be consistent with $Fe_2Cl_2$(btdd) and other $M_2Cl_2$(btdd) frameworks. The determination of the background, correct unit cell parameters, sample displacement and profile parameters to be used in the construction of the structural model, was done on the basis of these structureless Le Bail refinements.

The structural model was first prepared on the diffraction data for evacuated $V_2Cl_{2.8}$(btdd). The BTDD linker was modeled as a rigid body by means of the z-matrix syntax, adopting ¼ of a ligand with its center of mass (a dummy atom with zero occupancy) in ½, ½, ½; Wyckoff site d. Vanadium atom was refined in x, 0, ½; Wyckoff site g, and $Cl_1$ in x,0,0; Wyckoff site f. A subsequent Rietveld refinement, adding another chlorine atom ($Cl_2$) at the apical position of the Vanadium site (with a refinable site occupancy factor) revealed the presence of the second coordinated Cl atom, with its occupancy factor refined to 41(1)%. During these Rietveld refinement steps, the bond lengths of the linker atoms was refined within min and max value within those observed in the CSD for the same linker.

The structural model for the evacuated sample was subsequently used as starting point for the determination of the structural model for $N_2$-dosed $V_2Cl_{2.8}$(btdd) sample. For the determination of $N_2$ position and its occupancy factor, all parameters already determined for evacuated $V_2Cl_{2.8}$(btdd) sample were initially kept fixed (V, Cl1, Cl2 and linker positions, as well as the Cl2 occupancy factor). During the refinements the $N_2$ molecule, modeled as a rigid molecule (with N≡N distance fixed to 1.12 Å), was refined on the x, 0, ½ position, with an occupancy factor that refined to 27(3)%. During the last Rietveld refinement, all parameters (except the Cl2 occupancy factor) were freely refined.

Peak shapes were described with the fundamental parameters approach (41). See Cheary and Coelho, 1992, J. Appl. Cryst., 25, 109. The background was modelled with a Chebyshev polynomial function. The thermal effect was simulated by using a single isotropic parameter for the metal ion, augmented by 2.0 Å$^2$ for lighter atoms.

The result of the Rietveld refinements for evacuated and $N_2$-dosed $V_2Cl_{2.8}$(btdd) are reported in FIGS. 5 and 6, respectively.

Infrared Spectroscopy.

Infrared spectra were collected using a Bruker Vertex 70 spectrometer equipped with a glowbar source, KBr beamsplitter, and a liquid nitrogen cooled mercury-cadmium-telluride detector. A custom-built diffuse reflectance system with a IR-accessible gas dosing cell was used for all measurements. Sample temperature was controlled by an Oxford Instruments OptistatDry TLEX cryostat, and sample atmosphere was controlled by a Micromeritics ASAP 2020Plus gas sorption analyzer. Prior to measurement, activated $V_2Cl_{2.8}$(btdd) (10 wt %) was dispersed in dry KBr in an argon-filled glovebox and evacuated at room temperature for 30 minutes. Spectra were collected in situ under UHP-grade $N_2$ and CO, and $^{15}N_2$ (98 atom % $^{15}N$, Sigma-Aldrich) at 4 $cm^{-1}$ resolution continually until equilibrium was observed.

Solid State Nuclear Magnetic Resonance Spectroscopy.

NMR spectra were collected for free gas-phase $^{15}N_2$ (98 atom % $^{15}N$, Sigma-Aldrich) and $^{15}N_2$-dosed $V_2Cl_{2.8}$(btdd). For gas-phase $^{15}N_2$, $^{15}N_2$ was dosed into an empty 4 mm outer diameter glass tube at 700 mbar, and then flame sealed. Gas dosing for $V_2Cl_{2.8}$(btdd) was performed on a custom gas dosing manifold described previously. See, Milner et al., 2017, "A diaminopropane-appended metal-organic framework enabling efficient $CO_2$ capture from coal flue gas via a mixed adsorption mechanism," J. Am. Chem. Soc. 139, 13541-13553. The rotor was packed with ~30 mg of $V_2Cl_{2.8}$ (btdd) inside an $N_2$-filled glovebox, evacuated at room temperature for 30 minutes, and then dosed with 773 mbar of $^{15}N_2$ at room temperature with 30 minutes allowed for equilibration. For the measurement collection, all NMR spectra were recorded at 16.4 T, with a Bruker 3.2 mm magic angle spinning probe used for $^{15}N_2$-dosed $V_2Cl_{2.8}$(btdd) and a DOTY 4 mm magic angle spinning probe used for the free gas-phase $^{15}N_2$ sample. For free $^{15}N_2$ the sample was static during measurement, while $^{15}N_2$-dosed $V_2Cl_{2.8}$(btdd) was collected under magic-angle spinning at a rate of 15 kHz. Single pulse excitation was used for all NMR experiments. All spectra were referenced to $^{15}N$ in glycine with a chemical shift of 33.4 ppm. See, Bertani et al., 2014, "$^{15}N$ chemical shift referencing in solid state NMR," Solid State Nucl. Magn. Reson., 61, 15-18.

Vanadium K-Edge X-Ray Absorption Spectroscopy.

Data were collected at the Advanced Light Source bending magnet microprobe beamline 10.3.2 (2.1-17 keV) with the storage ring operating at 500 mA and 1.9 GeV. $V_2Cl_{2.8}$(btdd), $VCl_2$(tmeda)$_2$, and $VCl_3$(THF)$_3$ were all individually mounted under inert atmosphere conditions in an argon glovebox onto Kapton tape, sealed in multiple hermetic bags, transferred to the ALS, and measured in fluorescence mode by continuously scanning the Si (111) monochromator (Quick XAS mode). Fluorescence emission counts were recorded with a seven-element Ge solid-state detector (Canberra) and XIA electronics. All spectra were collected from 100 eV below and up to 300 eV above the edge and calibrated using a vanadium foil, with first derivative set at 5465.1 eV. All data were processed using LabVIEW custom software available at the beamline and further processed with Athena. See, Ravel and Newville, 2005, "ATHENA, ARTEMIS, HEPHAESTUS: data analysis for X-ray absorption spectroscopy using IFEFFIT," Journal of Synchrotron Radiation 12, 537.

X-Ray Photoelectron Spectroscopy.

X-ray photoelectron spectroscopy (XPS) was taken using a Perkin Elmer PHI 5600 XPS. The XPS was equipped with a 180 double focusing hemispherical analyzer. To prevent oxygen contamination and concomitant redox activity with samples, preparation and mounting were performed in an argon glovebox. The sample was affixed to a silicon wafer using double sided carbon tape. After mounting the wafer on the stage the sample was sealed in an airtight jar under argon. To load into the XPS, a glovebag containing the jar was sealed onto the loading chamber and subsequently purged with a high flow of argon for one hour, after which the sample was loaded into the chamber under argon.

Samples were calibrated using the aromatic carbon peak as a standard. For proper peak fitting, a Shirley background was applied to regions of interest and subtracted after peak fitting. Energy splitting of spin-orbit decoupled peaks were constrained using values obtained from $VCl_2$ and $VCl_3$ standards. All data processing and peak fitting was performed using CasaXPS.

CONCLUSION

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

We claim:

1. An adsorption material, comprising:
a metal—organic framework comprising a plurality of vanadium sites interconnected by a plurality of organic linkers, wherein
each respective organic linker M in the plurality of organic linkers comprises:

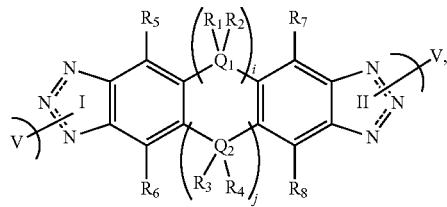

wherein,
$Q_1$ and $Q_2$ are each independently carbon, oxygen, or nitrogen,
i and j are each independently 0, 1, or 2, with the proviso that at least one $Q_1$ is carbon when i is 2 and at least one $Q_2$ is carbon when j is 2,
each instance of each $R_1$, $R_2$, $R_3$, $R_4$, and $R_5$, $R_6$, $R_7$, and $R_8$ is independently H, halogen, substituted or unsubstituted alkyl, substituted or unsubstituted heteroalkyl, substituted or unsubstituted aryl, substituted or unsubstituted heteroaryl, substituted or unsubstituted heterocycloalkyl, substituted or unsubstituted alkoxy, substituted or unsubstituted arlyoxy, or substituted or unsubstituted heteroaryloxy, with the provisos that:
$R_1$ and $R_2$ are not present when a $Q_1$ is oxygen,
$R_3$ and $R_4$ are not present when a $Q_2$ is oxygen,
one of $R_1$ and $R_2$ is not present when $Q_1$ is nitrogen, and one of $R_3$ and $R_4$ is not present when $Q_2$ is nitrogen; and wherein a vanadium site in the plurality of vanadium sites has a coordination of:

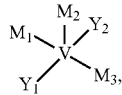

wherein, $M_1$, $M_2$, $M_3$ are each a respective organic linker M in the plurality of organic linkers that binds to the vanadium site through a free nitrogen in the I or II ring of the respective organic linker, and $Y_1$ and $Y_2$ are each independently, chlorine, bromine, —$SCH_3$, —SCN, or —NR'R", wherein R' and R" are substituted or unsubstituted alkyl, or substituted or unsubstituted heteroalkyl.

2. The adsorption material of claim 1, wherein at least twenty percent of the vanadium sites in the plurality of vanadium sites have a coordination of:

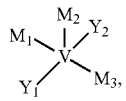

wherein, $M_1$, $M_2$, and $M_3$ are each a respective organic linker M in the plurality of organic linkers that binds to the vanadium site through a free nitrogen in the I or II ring of the respective organic linker M, and $Y_1$ and $Y_2$ are each independently, chlorine, bromine, —$SCH_3$, —SCN, or —NR'R", wherein R' and R" are substituted or unsubstituted alkyl, or substituted or unsubstituted heteroalkyl.

3. The adsorption material of claim 1, wherein at least ninety-eight percent of the vanadium sites in the plurality of vanadium sites have a coordination of:

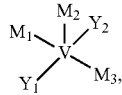

wherein, $M_1$, $M_2$, and $M_3$ are each a respective organic linker M in the plurality of organic linkers that binds to the vanadium site through a free nitrogen in the I or II ring of the respective organic linker M, and $Y_1$ and $Y_2$ are each independently, chlorine, bromine, —$SCH_3$, —SCN, or —NR'R", wherein R' and R" are substituted or unsubstituted alkyl, or substituted or unsubstituted heteroalkyl.

4. The adsorption material of claim 1, wherein $Q_1$ and $Q_2$ are each oxygen, i is one and j is one so that each respective organic linker M in the plurality of organic linkers comprises:

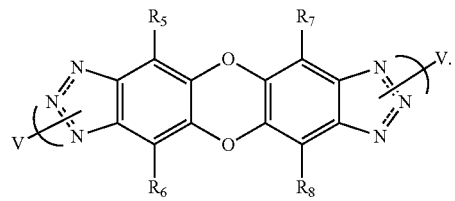

5. The adsorption material of claim 1, wherein i is zero and j is zero so that each respective organic linker M in the plurality of organic linkers comprises:

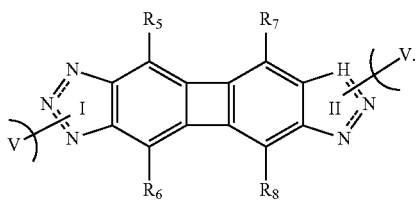

6. The adsorption material of claim 1, wherein $Q_1$ and $Q_2$ are each oxygen, i is 1, j is 1, and each instance of each $R_5$, $R_6$, $R_7$, and $R_8$ is independently H, halogen, substituted or unsubstituted n-alkyl or a substituted or unsubstituted branched-chain alkyl.

7. The adsorption material of claim 1, wherein $Q_1$ and $Q_2$ are each oxygen, i is 1, j is 1, and each instance of each $R_5$, $R_6$, $R_7$, and $R_8$ is independently H.

8. A method of synthesizing an adsorption material, the method comprising:

(A) reacting a vanadium source and a ligand source in a solvent that includes an acid at a temperature of between 105° C. and 135° C. to form an intermediate product, wherein the vanadium source comprises $VY_2$, $VY_2(tmeda)_2$, $VY_2(pyridine)_4$, or $VY_2(CH_3OH)_4$, the ligand source is $H_2$(ligand), wherein the ligand has the structure M:

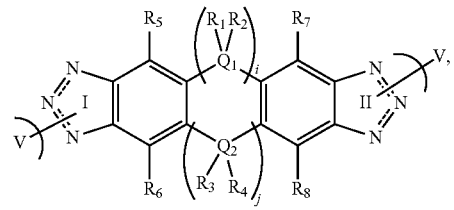

wherein, tmeda is N,N,N',N"-tetramethylethane-1,2-diamine,

Y is chlorine, bromine, —$SCH_3$, —SCN, or —NR'R", wherein R' and R" are substituted or unsubstituted alkyl, or substituted or unsubstituted heteroalkyl, $Q_1$ and $Q_2$ are each independently carbon, oxygen, or nitrogen, i and j are each independently 0, 1, or 2, with the proviso that at least one $Q_1$ is carbon when i is 2 and at least one $Q_2$ is carbon when j is 2, the free nitrogen in the I ring and the II ring each bind a hydrogen prior to the reacting, each instance of each $R_1$, $R_2$, $R_3$, $R_4$, and $R_5$, $R_6$, $R_7$, and $R_8$ is independently H, halogen, substituted or unsubstituted alkyl, substituted or unsubstituted heteroalkyl, substituted or unsubstituted aryl, substituted or unsubstituted heteroaryl, substituted or unsubstituted heterocycloalkyl, substituted or unsubstituted alkoxy, substituted or unsubstituted arlyoxy, or substituted or unsubstituted heteroaryloxy, with the provisos that:
$R_1$ and $R_2$ are not present when a $Q_1$ is oxygen,
$R_3$ and $R_4$ are not present when a $Q_2$ is oxygen,
one of $R_1$ and $R_2$ is not present when $Q_1$ is nitrogen, and
one of $R_3$ and $R_4$ is not present when $Q_2$ is nitrogen;
(B) collecting the intermediate product and washing the intermediate product with a washing agent; and
(C) activating the intermediate product to thereby form the adsorption material by heating the washed intermediate product to at least 160° C. under a vacuum; wherein the adsorption material includes a vanadium site having a coordination of:

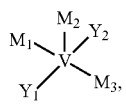

wherein,
$M_1$, $M_2$, and $M_3$ are each a respective organic linker M in the plurality of organic linkers that binds to the vanadium site through the free nitrogen in the I or II ring of the respective organic linker M, and
$Y_1$ and $Y_2$ are each independently Y.

9. The method of claim 8, wherein the temperature in the activating (C) is at least 170° C.

10. The method of claim 8, wherein the reacting (A) occurs for six days or more.

11. The method of claim 8, wherein the reacting (A) occurs for between six days and twelve days.

12. The method of claim 8, wherein the activating (C) occurs for between 40 hours and 70 hours.

13. The method of claim 8, wherein the reacting (A) is done at between 115° C. and 125° C. to form the intermediate product.

14. The method of claim 8, wherein $Q_1$ and $Q_2$ are each oxygen, i is one and j is one such that the ligand has the structure:

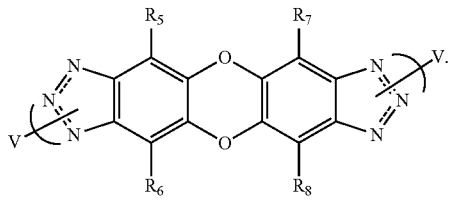

15. The method of claim 8, wherein $Q_1$ and $Q_2$ are each oxygen, i is 1, j is 1, and each instance of each $R_5$, $R_6$, $R_7$, and $R_8$ is independently H, halogen, substituted or unsubstituted n-alkyl or a substituted or unsubstituted branched-chain alkyl.

16. The method of claim 8, wherein $Q_1$ and $Q_2$ are each oxygen, i is 1, j is 1, and each instance of each $R_5$, $R_6$, $R_7$, and $R_8$ is independently H.

17. The method of claim 8, wherein the acid is triflic (trifluoromethanesulfonic) acid, tosylic (p-Toluenesulfonic) acid, mesylic (methanesulfonic) acid, besylic (benzenesulfonic) acid, polystyrene sulfonic acid, ethanesulfonic acid, hydrochloric acid (HCl), hydrobromic acid (HBr), or chromic acid ($H_2CrO_4$), or a combination thereof.

18. The method of claim 8, wherein the solvent comprises dimethylformamide (DMF), N,N'-dimethylactamide (DMA), N,N'-diethylformamide (DEF), N,N-dimethylmethoxyacetamide, dimethylsulfoxide, hexamethylphosphoramide, N-methyl-2-pyrrolidone, dimethyl sulfone, tetramethylsulfone, or a combination thereof.

19. A method for removing $N_2$ from a biogas, natural gas, or landfill gas, the method comprising contacting the biogas, natural gas, or landfill gas with the adsorption material of claim 1 to reversibly adsorb $N_2$ from the biogas thereby generating an adsorption material enriched for $N_2$ and a residual gas that is greater than ninety-eight percent pure methane.

20. The method of claim 19, the method further comprising stripping at least fifty percent of the $N_2$ from the adsorption material enriched for $N_2$ using a regeneration method.

21. The method of claim 20, wherein the regeneration method is a temperature swing adsorption method, a vacuum swing adsorption method, a pressure swing adsorption method, a concentration swing adsorption method, or a combination thereof.

22. A method of separating a π-acid from a gas produced by a source, comprising exposing the π-acid within the gas to the adsorption material of claim 1 whereby the π-acid is reversibly separated into the adsorption material.

23. The method of claim 22, wherein the π-acid is reversibly separated from the adsorption material by a regeneration process.

24. A method of separating an olefin (alkene) from a paraffin (alkane) counterpart of the olfefin in a gas, comprising exposing the olefin within the gas to the adsorption material of claim 1 whereby the olefin is reversibly separated into the adsorption material.

25. The method of claim 24, wherein the olefin is reversibly separated from the adsorption material by a regeneration process.

* * * * *